(12) United States Patent
Jayol

(10) Patent No.: US 11,247,031 B2
(45) Date of Patent: *Feb. 15, 2022

(54) GIRTH ADJUSTABLE DEVICE

(71) Applicant: Benjamin Ernest Hélois Jayol, Los Angeles, CA (US)

(72) Inventor: Benjamin Ernest Hélois Jayol, Los Angeles, CA (US)

( * ) Notice: Subject to any disclaimer, the term of this patent is extended or adjusted under 35 U.S.C. 154(b) by 889 days.

This patent is subject to a terminal disclaimer.

(21) Appl. No.: 16/005,679

(22) Filed: Jun. 12, 2018

(65) Prior Publication Data
US 2019/0262591 A1    Aug. 29, 2019

Related U.S. Application Data

(60) Provisional application No. 62/636,240, filed on Feb. 28, 2018.

(51) Int. Cl.
*A61M 29/00* (2006.01)
*A61B 1/32* (2006.01)

(52) U.S. Cl.
CPC ............... *A61M 29/00* (2013.01); *A61B 1/32* (2013.01)

(58) Field of Classification Search
CPC .................................. A61M 29/00; A61B 1/32
See application file for complete search history.

(56) References Cited

U.S. PATENT DOCUMENTS

| | | | |
|---|---|---|---|
| 5,785,648 A * | 7/1998 | Min | A61B 1/32 600/206 |
| 5,795,289 A * | 8/1998 | Wyttenbach | A61B 1/32 600/207 |
| 9,533,080 B1 * | 1/2017 | Carrier | A61M 1/86 |
| 2018/0193619 A1* | 7/2018 | Juravic | A61D 1/10 |
| 2019/0262591 A1* | 8/2019 | Jayol | A61B 1/32 |
| 2021/0008357 A1* | 1/2021 | Jayol | A61H 23/0263 |

* cited by examiner

*Primary Examiner* — Steven O Douglas

(57) ABSTRACT

A girth adjustable device for physical therapy such as the dilation and stretch of body orifices that can repeatedly, gradually increase a uniform and sustainable pressure over the entire lateral surface area and over the entire length of a body orifice at the same time, and gradually decrease the pressure uniformly from the entire lateral surface area and the entire length of a body orifice at the same time. The girth adjustable device comprises at least one controller, a housing, at least one threaded shaft, at least one module, a plurality of shaft member and at least one sheath. The part of the device inserted into a body orifice is the shaft. In a body orifice, the user via the controller rotates clockwise the threaded shaft to increase the girth of the shaft. Then, the user via the controller rotates counter-clockwise the threaded shaft to decrease the girth of the shaft.

33 Claims, 50 Drawing Sheets

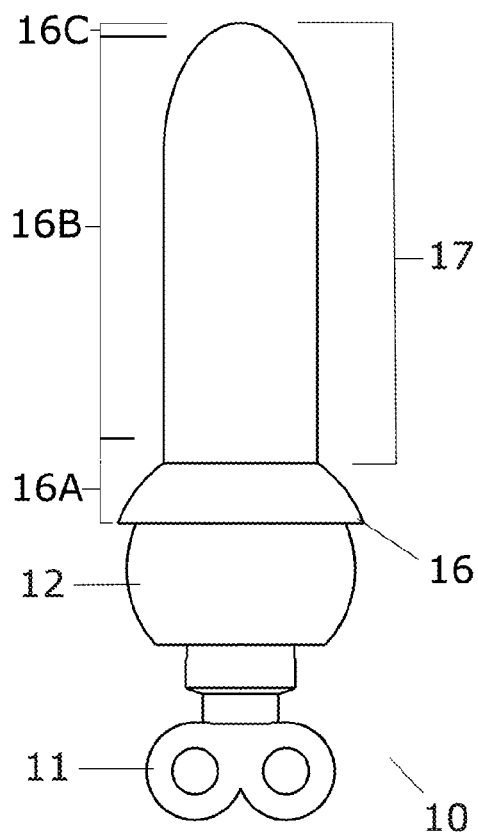
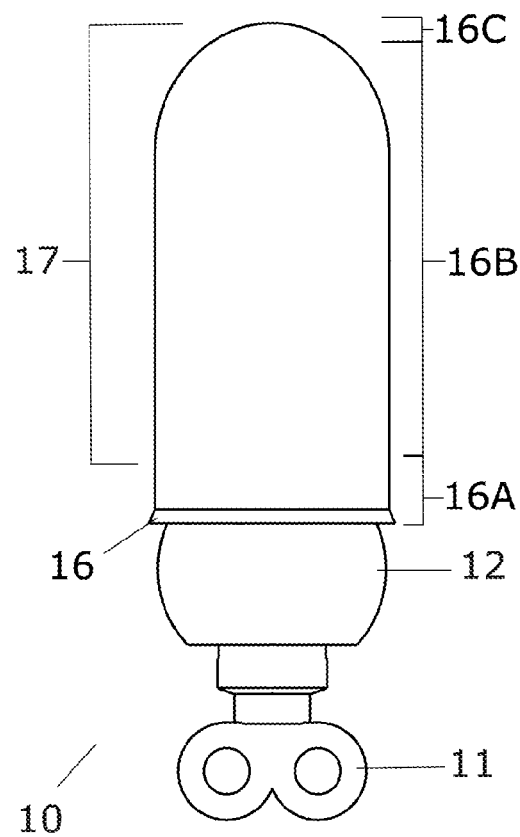
FIG. 1A
FIG. 1B
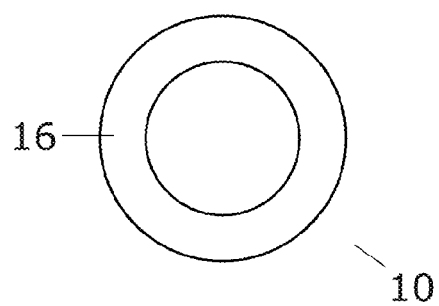
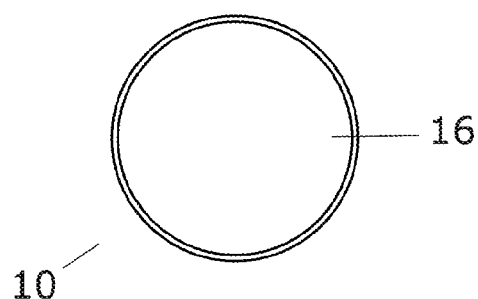
FIG. 1C
FIG. 1D

FIG. 18
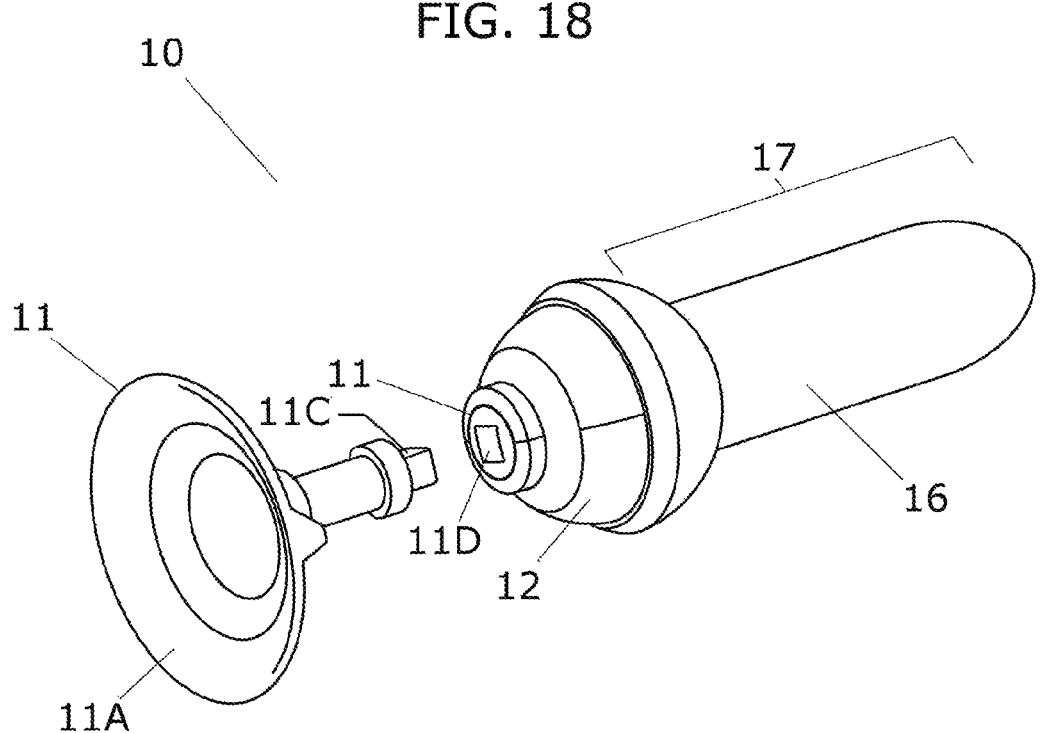
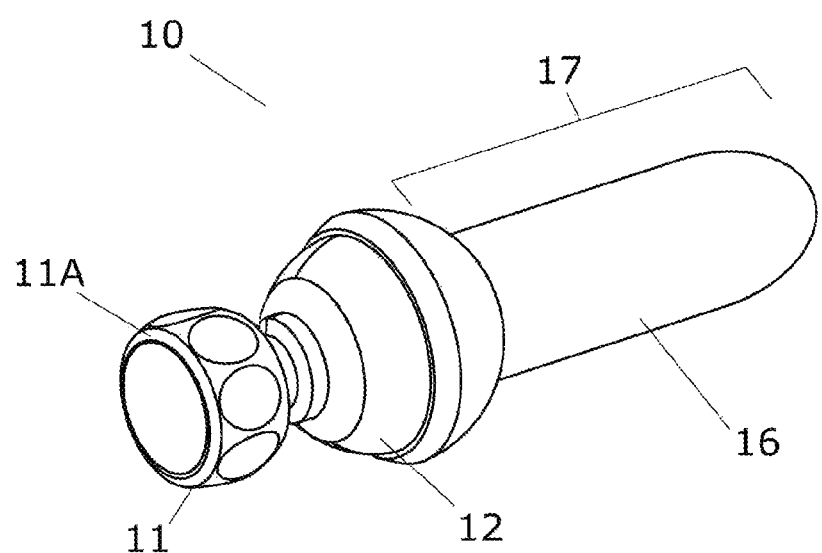
FIG. 19A

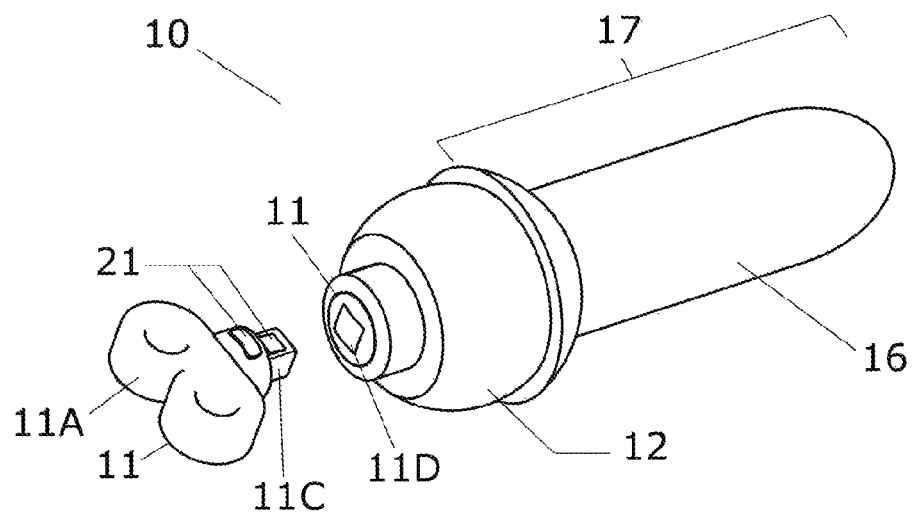
FIG. 20A
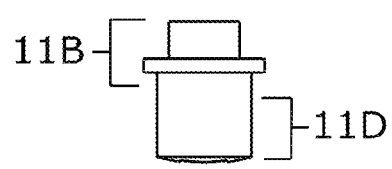 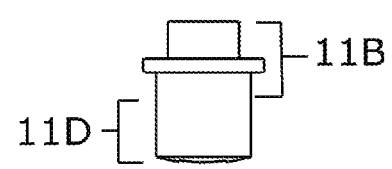
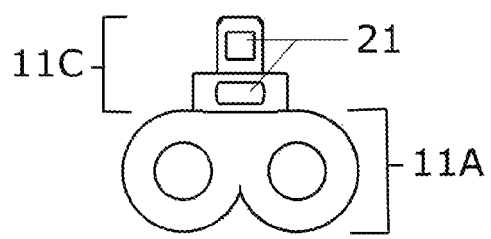 
FIG. 20B  FIG. 20C

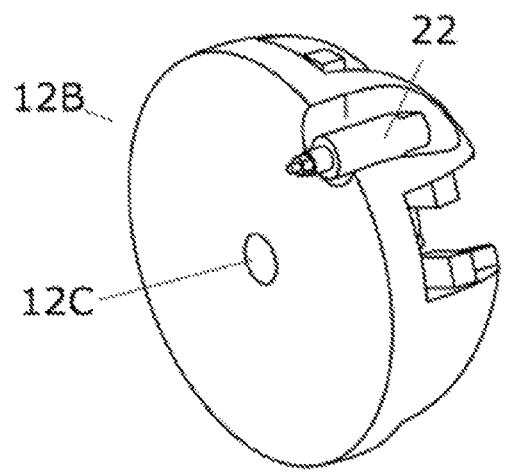
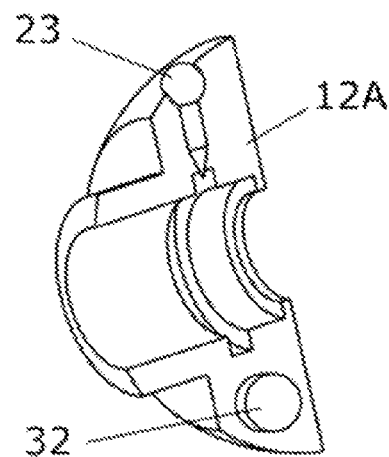
FIG. 29A  FIG. 29B
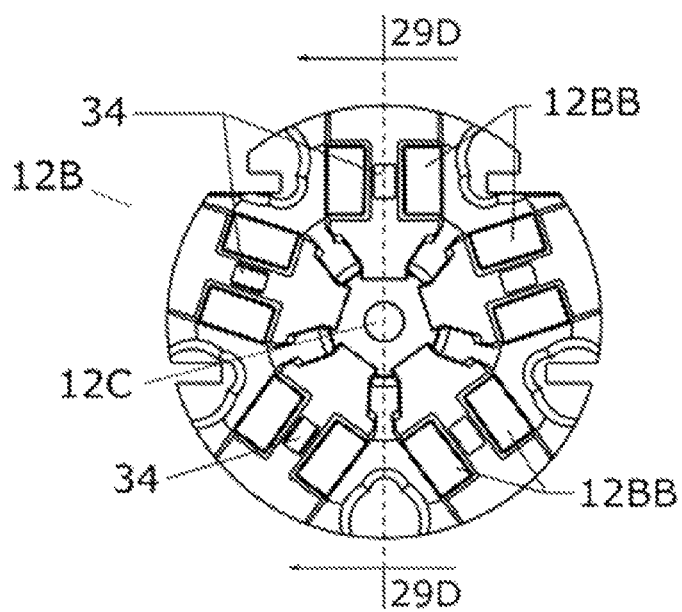
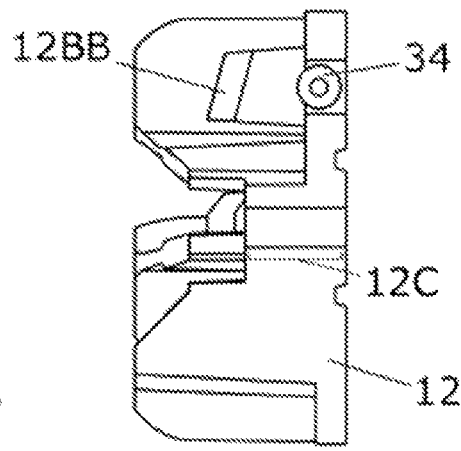
FIG. 29C  FIG. 29D

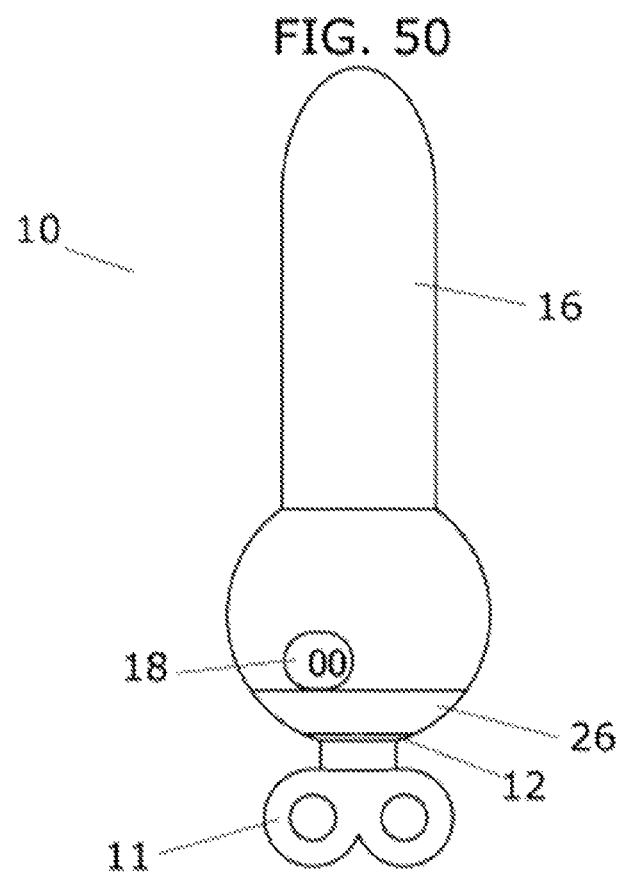
FIG. 50
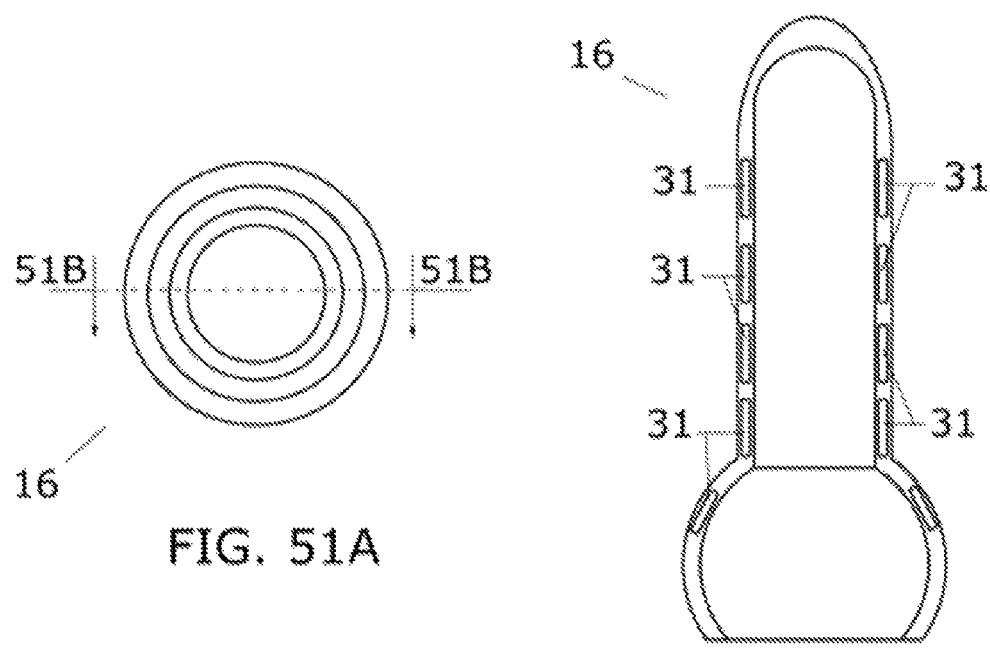
FIG. 51A
FIG. 51B

GIRTH ADJUSTABLE DEVICE

CROSS REFERENCE TO RELATED APPLICATION

This application claims the benefit of Provisional application No. 62/636,240, filed on Feb. 28, 2018.

BACKGROUND OF THE INVENTION

Field of Invention

The present invention relates to a physical therapy apparatus and more specifically it relates to a girth adjustable device for the dilation and stretch of body orifices.

Description of Related Art

Devices for body orifice dilation and stretch have been a fast growing area of interest for many applications such as oncology, radiotherapy, gynecology and sex therapy. It concerns male and female.

A body orifice such as a vagina or an anus is a tubular body part. The body orifice shape can be considered as a hollow cylinder which means that a body orifice has a center, a diameter, a lateral surface area and a length. An efficient way to dilate and stretch a body orifice is to use a device that can repeatedly, gradually increase a uniform and sustainable pressure over the entire lateral surface area, and over the entire length of the body orifice at the same time. The pressure should go from the center toward the lateral surface area of the body orifice.

As the body orifice can be considered as a sensitive body part, such devices should provide a safe and gradual control of the pressure.

As the dilation and stretch of body orifices is a procedure that requires time, the user may prefer to keep such device in their body orifice and be able to freely do other activities, therefore such devices should be lightweight (which can be considered to indicate non-motorized) and also be as compact as possible.

Currently, none of the devices on the market provide a girth adjustable device with a non-motorized version, a version with a removable controller or a version providing other features related to physical therapy and/or body orifice stimulation, wherein the user can repeatedly, safely, gradually, precisely and comfortably, generate a uniform and sustainable pressure over the entire lateral surface area and over the entire length of the body orifice at the same time.

Some of devices propose a set of fixed girth devices. For example, the document US 2007/0043388 discloses a set of a series of colored dilator devices to indicate the difference in girth size. The usage of such dilator set is confusing as the user has to manage several devices. The pressure generated over the lateral surface area of the body orifice is not gradual as each device has a fixed girth.

Other devices commonly referred to as inflatable devices have several drawbacks. Their design is commonly made with a fixed pump and a pipe that can be considered bulky by the user. The air-chamber used in those devices cannot provide a sustainable and precise pressure over the lateral surface area of the body orifice and have the risk of over-filling the device and rupturing in the body orifice.

BRIEF SUMMARY OF THE INVENTION

The present invention is a girth adjustable device, hereinafter referred to as "the device", for the dilation and stretch of body orifices, wherein the same can be utilized such as, but not limited to: massage, sexual stimulation and therapeutical treatment.

The device preferably comprises a controller, a housing, a threaded shaft, at least one module having at least two conical sections with a slant height or at least two modules having at least one conical section with a slant height, a plurality of shaft members and one sheath.

The part of the device that can be inserted into a body orifice and whose girth can be repeatedly adjusted safely, gradually, precisely and comfortably to generate a uniform and sustainable pressure over the entire lateral surface area and the entire length of a body orifice at the same time, is referred to hereinafter as "the shaft".

The user via the controller can increase or decrease the girth of the shaft of the device. The action performed by the user via the controller to increase or decrease the girth of the shaft is referred hereinafter to as "the adjustment". The adjustment is repeatable, safe, gradual, precise, and comfortable for the user. Those characteristics of the adjustment are referred hereinafter to "the specific characteristics".

Therefore, attention being called to the fact that the device is such that when the user via the controller increases the girth of the shaft in a body orifice, the device generates a safe, gradual, sustainable, and substantially uniform pressure over the entire lateral surface area and over the entire length of the body orifice at the same time. When the user via the controller decreases the girth of the shaft, the pressure over the entire lateral surface area and over the entire length of the body orifice is reduced safely, gradually and uniformly from the entire lateral surface area and the entire length of the body orifice at the same time.

This specific performance is feasible partially due to the longitudinal and uniform configuration of a plurality of shaft members included into the device (five or six shaft members in the preferred embodiment of the device). The specific characteristics of the adjustment of the device allow the user to effectively perform the dilation and stretch of a body orifice.

Attention being called to the fact that the device in its preferred embodiment is non-motorized and therefore it ensures a lightweight, compact and substantially noiseless device for an optimum utilization by the user.

There has thus been outlined, rather broadly, the more important features of the invention in order that the detailed description thereof may be better understood. There are additional features of the invention that will be described hereinafter and that will form the subject matter of the claims appended hereto.

It is to be understood that the device is not limited in its application to the details of construction and to the arrangements of the components set forth in the following description or illustrated in the drawings. The invention is capable of other embodiments and of being practiced and carried out in various ways. Also, it is to be understood that the phraseology and terminology employed hereinafter are for the purpose of the description and should not be regarded as limiting.

To the accomplishment of the above and related objects, this invention may be embodied in the form illustrated in the accompanying drawings, attention being called to the fact, however, that the drawings are illustrative only, and that changes may be made in the specific construction illustrated and described within the scope of the appended claims.

BRIEF DESCRIPTION OF THE DRAWINGS

FIG. 1A illustrates a front view of the device 10 with the shaft 17 at its minimum girth according to an embodiment of the device 10. FIG. 1B illustrates a front view of the device 10 with the shaft 17 at its maximum girth according to an embodiment of the device 10. FIG. 1G illustrates a top view of the device 10 with the shaft 17 at its minimum girth according to an embodiment of the device 10. FIG. 1D illustrates a front view of the device 10 with the shaft 17 at its maximum girth according to an embodiment of the device 10.

FIG. 18 illustrates a perspective view of the device 10 with the shaft 17 at its minimum girth according to an embodiment of the device 10.

FIG. 19A illustrates a perspective view of the device 10 with the shaft 17 at its minimum girth according to an embodiment of the device 10.

FIG. 20A illustrates a perspective view of the device 10 with the shaft 17 at its minimum girth according to an embodiment of the device 10. FIG. 20B illustrates a front view of the controller 11 according to an embodiment of the device 10. FIG. 20C illustrates a side view of the controller 11 according to an embodiment of the device 10.

FIG. 29A illustrates a perspective view of a part or the housing 12 according to an embodiment of the device 10, FIG. 29B illustrates a perspective view of a part of the housing 12 according to an embodiment of the device 10. FIG. 29C illustrates a top view of a part of the housing 12 according to an embodiment. FIG. 29D illustrates a section view of FIG. 29C.

FIG. 50 illustrates a front view of the device 10 with the shaft 17 at its minimum girth according to an embodiment of the device 10.

FIG. 51A illustrates a bottom view of the sheath 16 according to an embodiment. FIG. 51B illustrates a section view of FIG. 51A.

DETAILED DESCRIPTION OF THE INVENTION

Figure 2A:
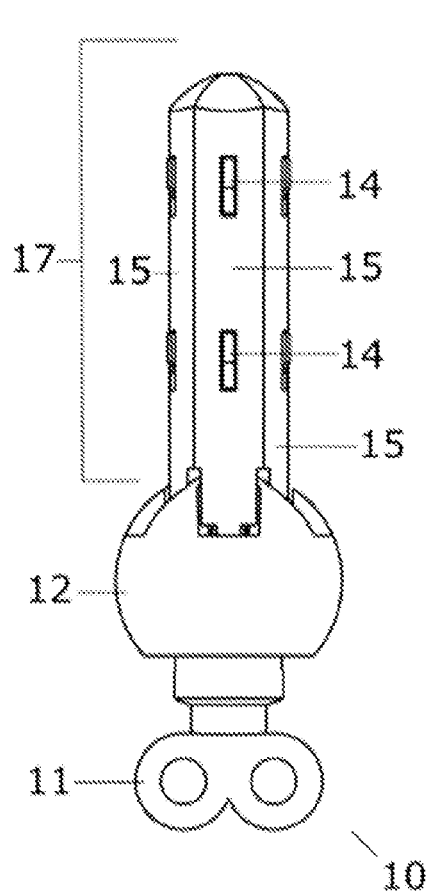
FIG. 2A illustrates a front view of the device 10 with the shaft 17 at its minimum girth according to an embodiment of the device 10 (sheath 16 not illustrated in FIG. 2A).
Figure 2B:
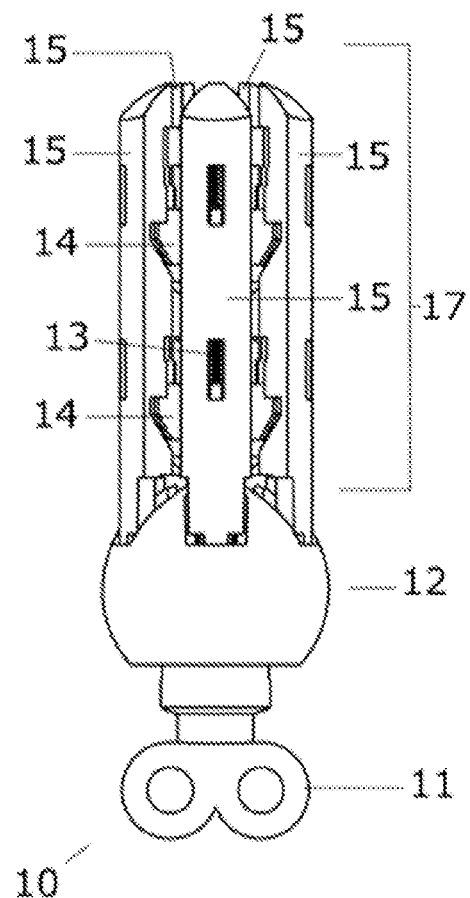
FIG. 2B illustrates a front view of the device 10 with the shaft 17 at its maximum girth according to an embodiment of the device 10 (sheath 16 not illustrated in FIG. 2B).
Figure 2C:
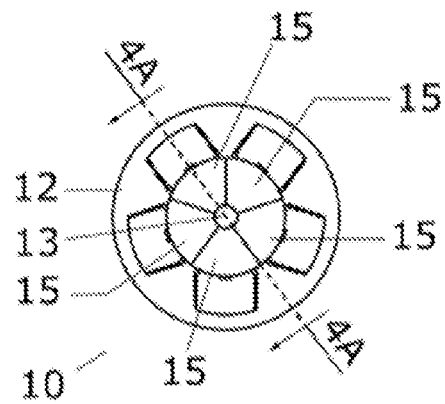
FIG. 2C illustrates a top view of the device 10 with the shaft 17 at its minimum girth according to an embodiment of the device 10 (sheath 16 not illustrated in FIG. 2C).
Figure 2D:
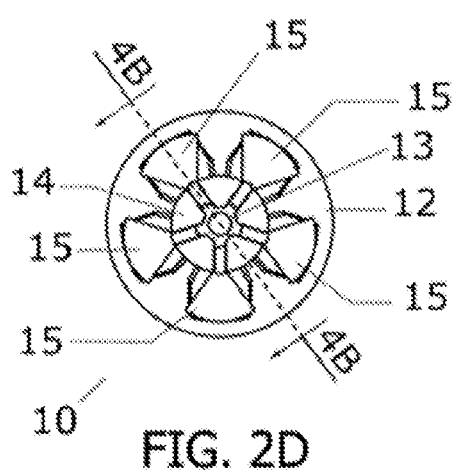
FIG. 2D illustrates a top view of the device 10 with the shaft 17 at its maximum girth according to an embodiment of the device 10 (sheath 16 not illustrated in FIG. 2D).
Figure 3A:
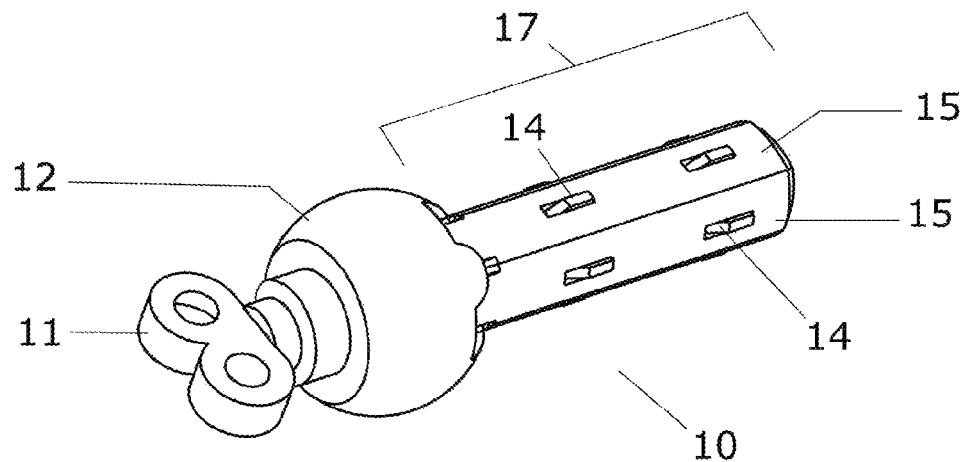
FIG. 3A illustrates a perspective view of the device 10 with the shaft 17 at its minimum girth according to an embodiment of the device 10 (sheath 16 not illustrated in FIG. 3A).
Figure 3B:
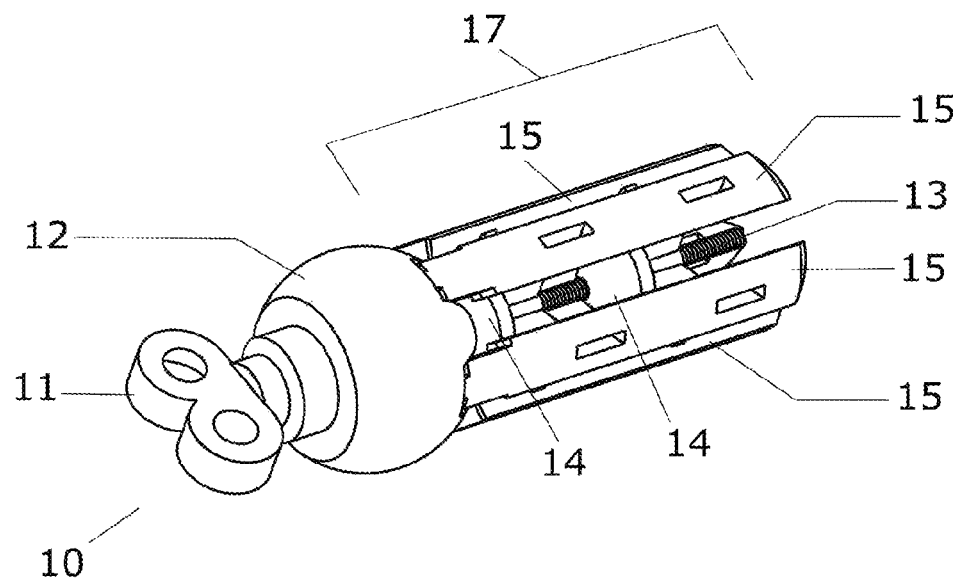
FIG. 3B illustrates a perspective view of the device 10 with the shaft 17 at its maximum girth according to an embodiment of the device 10 (sheath 16 not illustrated in FIG. 3B).
Figure 4A:
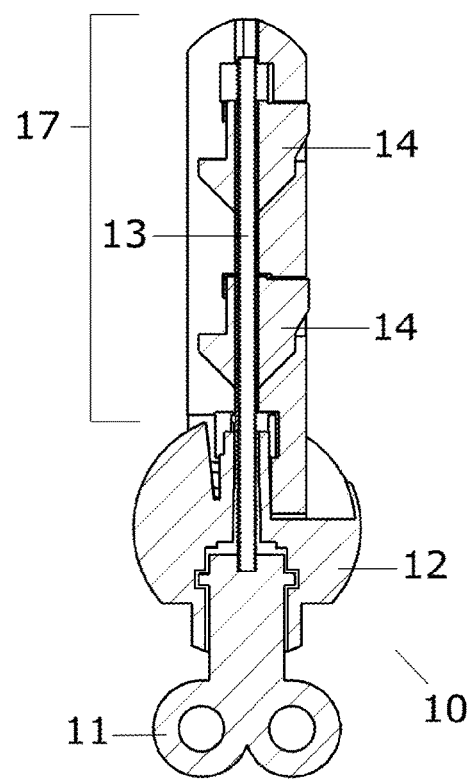
FIG. 4A illustrates a section view of FIG. 2C.
Figure 4B:
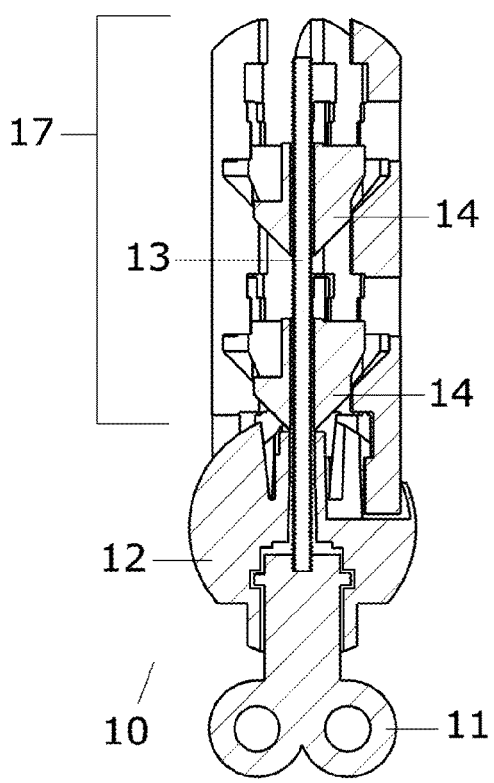
FIG. 4B illustrates a section view of FIG. 2D.
Figure 4C:
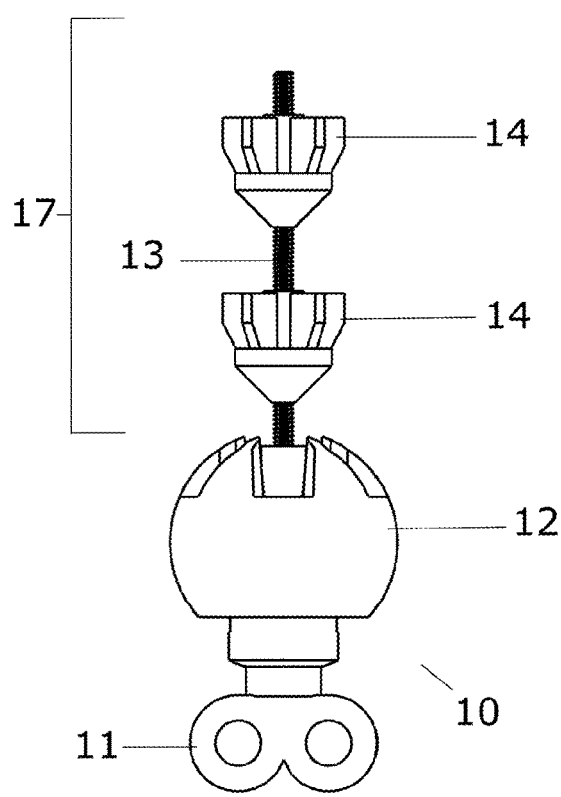
FIG. 4C illustrates a front view of the device 10 with the shaft 17 at its minimum girth according to an embodiment of the device 10 (sheath 16 and plurality of shaft members 15 not illustrated in FIG. 4A).
Figure 4D:
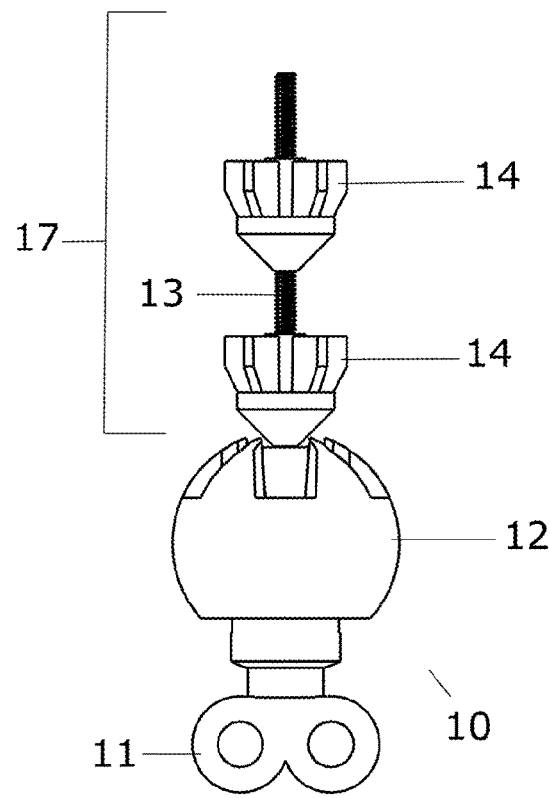
FIG. 4D illustrates a front view of the device 10 with the shalt 17 at its maximum girth according to an embodiment of the device 10 (sheath 16 and plurality of shaft members 15 not illustrated in FIG. 4B).

As used herein, the term «and/or» includes any and all combinations of one or more of the associated listed items. As used herein, the singular forms «a», «an», «and» and «the» are intended to include the plural forms as well as the singular forms, unless the context clearly indicates otherwise. It will be further understood that the terms, «has», «having», «configured», «is (or are) configured», «may be configured», «comprise», «comprises» and/or «comprising», when used in this specification, specify the presence of stated features, members, parts, elements, and/or components, but do not preclude the presence or addition of one or more other features, members, parts, elements, component, and/or groups thereof.

Turning now descriptively to the drawings, in which similar reference characters denote similar elements through the several views.

Overview

The part of the device 10 that can be inserted into a body orifice whose girth can be repeatedly adjusted safely, gradually, precisely and comfortably, and generate a uniform and sustainable pressure over the entire lateral surface area and over the entire length of a body orifice is referred hereinafter to "the shaft".

The action performed by the user via the controller 11 to increase or decrease the girth of the shaft 17 is referred hereinafter to as "the adjustment". The adjustment is safe, gradual, precise, repeatable and comfortable for the user. Those characteristics of the adjustment are referred hereinafter to as "the specific characteristics".

Figure 5B:
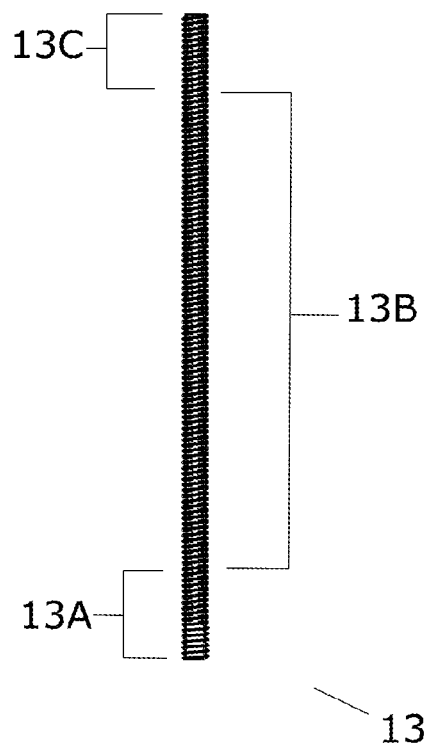
FIG. 5B illustrates a front view of the threaded shaft 13 according to an embodiment of the device 10.

The threaded shaft 13 (as illustrated in FIG. 5B) has a first end 13A, a middle section 13B and a second end 13C. The direction of orientation going from the first end 13A to the second end 13C of the threaded shaft 13 is referred hereinafter to as "the longitudinal axis".

FIG. 1, FIG. 2, FIG. 3, and FIG. 4 illustrate the device 10, which preferably comprises a controller 11, a housing 12, a threaded shaft 13, at least one module 14 having at least two conical sections with a slant height (not illustrated in FIG. 1, FIG. 2, FIG. 3, and FIG. 4) or at least two modules 14 having at least one conical section with a slant height (illustrated in FIG. 1, FIG. 2, FIG. 3, and FIG. 4), five shaft members 15 and a sheath 16. As illustrated in FIG. 1A and FIG. 1B, the shaft 17 of the device 10 is going from the tip end 16C of the sheath 16 to the closest edge at the perimeter of the housing 12. FIG. 1A illustrates a front view of the device 10 with the shaft 17 at its minimum girth according to a preferred embodiment of the device 10, and FIG. 1B illustrates a front view of the device 10 with the shaft 17 at its maximum girth according to a preferred embodiment of the device 10. FIG. 1C illustrates a top view of the device 10 with the shaft 17 at its minimum girth according to a preferred embodiment of the device 10, and FIG. 1D illustrates a top view of the device 10 with the shaft 17 at its maximum girth according to a preferred embodiment of the device 10. The girth of the shaft 17 is adjustable to any size from its minimum girth to its maximum girth, which means that the adjustment results to any size of the girth of the shaft 17, from its minimum girth to its maximum girth. For a better understanding of the mechanism of the device 10, the sheath 16 is not illustrated in FIG. 2 and FIG. 3. FIG. 2A illustrates a front view of the device 10 with the shaft 17 at its minimum girth according to a preferred embodiment of the device 10, and FIG. 2B illustrates a front view of the device 10 with the shaft 17 at its maximum girth according to a preferred embodiment of the device 10. FIG. 2C illustrates a top view of the device 10 with the shaft 17 at its minimum girth according to a preferred embodiment of the device 10, and FIG. 2D illustrates a top view of the device 10 with the shaft 17 at its maximum girth according to a preferred embodiment of the device 10. FIG. 3A illustrates a perspective view of the device 10 with the shaft 17 at its minimum girth according to a preferred embodiment of the device 10, and FIG. 3B illustrates a perspective view of the device 10 with the shaft 17 at its maximum girth according to a preferred embodiment of the device 10. For a better understanding of the mechanism of the device 10, the sheath 16 and the plurality of shaft members 15 are not illustrated in FIG. 4. FIG. 4A illustrates a front view of the device 10 with the shaft 17 at its minimum girth according to a preferred embodiment of the device 10, and FIG. 4B illustrates a front view of the device 10 with the shaft 17 at its maximum girth according to a preferred embodiment of the device 10.

As illustrated in FIG. 1, FIG. 2, FIG. 3, and FIG. 4, the controller 11 is connected to the threaded shaft 13 inside the housing 12, the module 14 (or a plurality of modules 14) receives the threaded shaft 13, the module 14 (or a plurality of modules 14) is connected with the plurality of shaft members 15, the plurality of shaft members 15 is connected to the housing 12, the plurality of shaft members 15 surrounds the module 14 (or a plurality of modules 14), the sheath 16 is connected to the plurality of shaft members or to the plurality of shaft members and the housing 12, the sheath 16 surrounds the plurality of shaft members 15. The assembly of the controller 11, the housing 12, the threaded shaft 13, the module 14 (or a plurality of modules 14), the plurality of shaft members 15 and the sheath 16 characterized the device 10 in its preferred embodiment, such that when the user rotates the controller 11 clockwise, the threaded shaft 13 rotates clockwise, making the module 14 (or a plurality of modules 14) prevented from rotating, travel along the threaded shaft 13 in the direction of the housing 12, making each shaft member 15 travel perpendicularly to the longitudinal axis of the threaded shaft 13 in the opposite direction of the longitudinal axis of the threaded shaft 13, the sheath 16 made of a resilient material, deforms elastically from its original shape, the girth of the shaft 17 increases, until the controller 11 is no longer rotated clockwise by the user, meaning that the user has reached the desired girth of the shaft 17, meaning that the threaded shaft 13 is no longer rotated, stopping the module 14 from traveling along the threaded shaft 13, stopping each shaft member 15 from traveling perpendicularly to the longitudinal axis of the threaded shaft 13 in the opposite direction of the longitudinal axis of the threaded shaft 13, stopping the sheath 16 from deforming elastically, stopping the girth of the shaft 17 from increasing. The girth of the shaft 17 is sustained at this size. Then, when the user rotates counter-clockwise the controller 11, the threaded shaft 13 rotates counter-clockwise, making the module 14 (or a plurality of modules 14) prevented from rotating, travel along the threaded shaft 13 in the opposite direction of the housing 12, making the sheath 16 retrieve its original shape, making each shaft member 15 travel perpendicularly to the longitudinal axis of the threaded shaft 13 in the direction of the longitudinal axis of the threaded shaft 13, the girth of the shaft 17 decreases, until the controller 11 is no longer rotated counter-clockwise by the user, meaning that the user has reached the desired girth of the shaft 17, meaning that the threaded shaft 13 is no longer rotated, stopping the module 14 (or a plurality of modules 14) from traveling along the threaded shaft 13, stopping each shaft member 15 from traveling perpendicularly to the longitudinal axis of the threaded shaft 13 in the direction of the longitudinal axis of the threaded shaft 13, stopping the sheath 16 from retrieving its original shape, stopping the girth of the shaft 17 from decreasing. The girth of the shaft 17 is sustained at this size, until the user rotates again the controller 11 clockwise or counter-clockwise.

The controller 11 can no longer be rotated when the user has reached the maximum girth offered by the device 10, meaning that the threaded shaft 13 can no longer be rotated due to the fact that at least one module 14 is stopped from traveling along the threaded shaft 13 by pressing against at least one edge of the housing 12, and/or (in another preferred embodiment illustrated in FIG. 22A, by pressing against at least one clockwise translation stopper 13E), and/or by pressing against at least one edge of the module connector groove 15D (module connector groove 15D illustrated in FIG. 31) of at least one shaft member 15, and/or that at least one shaft member 15 is stopped from traveling perpendicularly to the longitudinal axis of the threaded shaft 13 in the opposite direction of the longitudinal axis of the threaded shaft 13 by pressing against at least one edge of the housing 12.

Figures 22A, 22B:
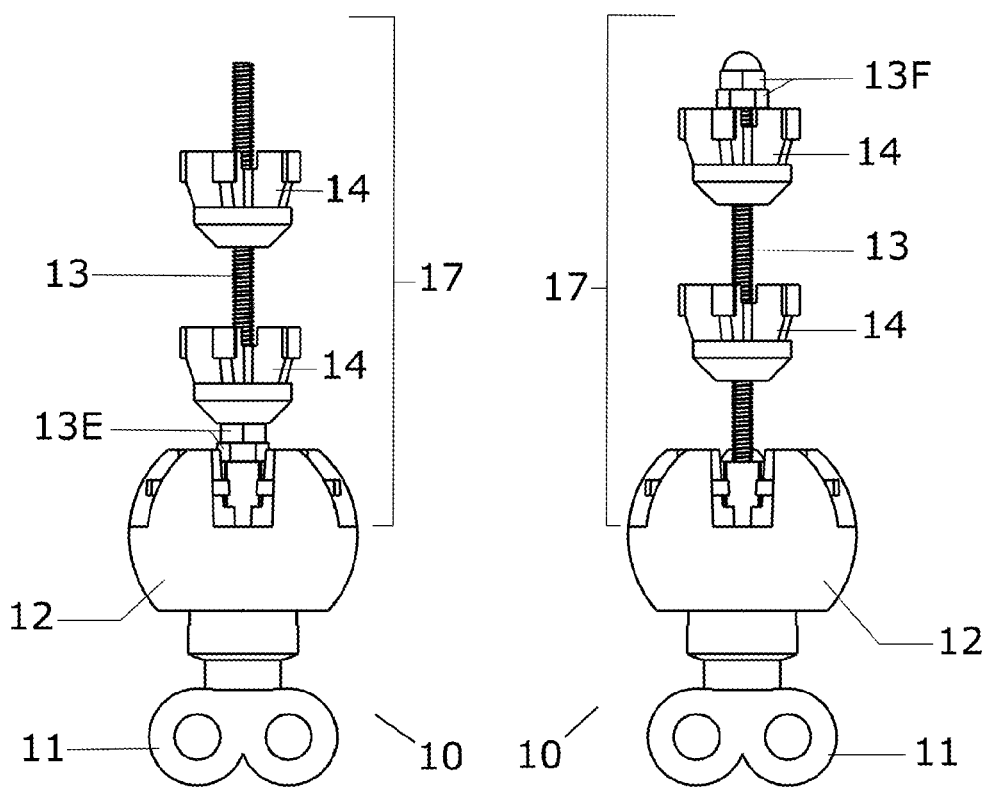
FIG. 22A illustrates a front view of the device 10 with the shaft 17 at its maximum girth according to an embodiment of the device 10 (sheath 16 and plurality of shaft members 15 not illustrated in FIG. 22A).
FIG. 22B illustrates a front view of the device 10 with the shaft 17 at its minimum girth according to an embodiment of the device 10 (sheath 16 and plurality of shaft members 15 not illustrated in FIG. 22B).

The controller 11 can no longer be rotated when the user has reached the minimum girth offered by the device 10, meaning that the threaded shaft 13 can no longer be rotated due to the fact that at least one module 14 is stopped from traveling along the threaded shaft 13 by pressing against at least one edge of the module cavity 15C (module cavity 15C illustrated in FIG. 31) and/or in another preferred embodiment illustrated in FIG. 22B, by pressing against at least one counter-clockwise translation stopper 13F.

Controller

The controller 11 is defined by its function to control the clockwise and counter-clockwise rotation of the threaded shaft 13. In a preferred embodiment the device 10 comprises one controller 11. In the preferred embodiment of the device 10, the controller 11 is directly operated by the user, meaning that the user with at least one hand, rotates clockwise or counter-clockwise the controller 11, however, in another embodiment, the controller 11 may be operated by the user via an electronic part 18 (electronic part 18 described in the Electronic part section), when the controller 11 is connected to an enclosed electric motor 19 (enclosed electric motor 19 described in Enclosed electric motor section).

Figure 5C:
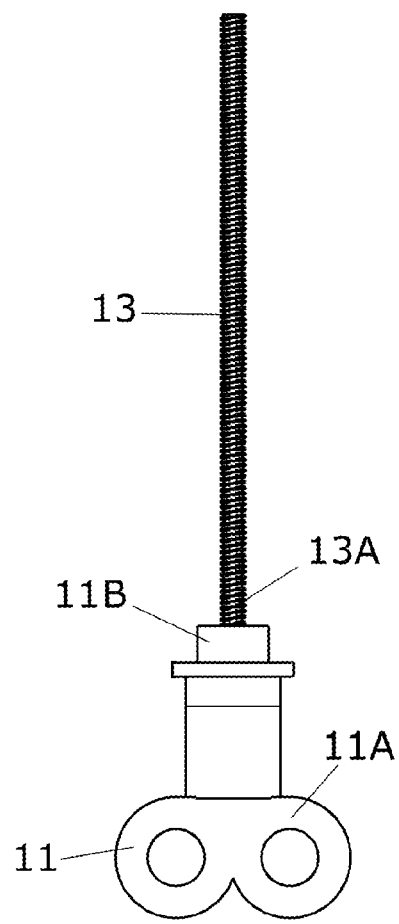
FIG. 5C illustrates a front view of the controller 11 connected to the threaded shaft 13 according to an embodiment of the device 10.
Figure 5A:
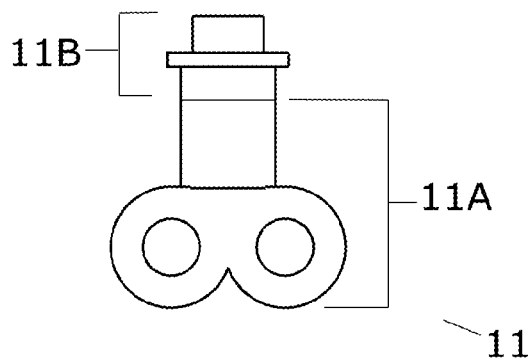
FIG. 5A illustrates a front view of the controller 11 according to an embodiment of the device 10.
Figure 5D:
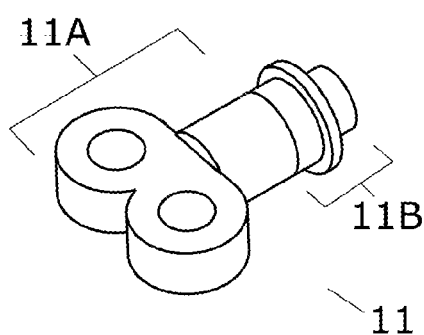
FIG. 5D illustrates a perspective view of the connector 11 according to an embodiment of the device 10.
Figure 6A:
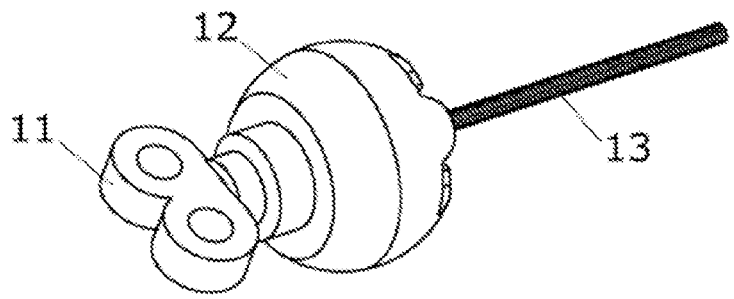
FIG. 6A illustrates a perspective view of the controller 11 connected to the threaded shaft 13 inside the housing 12 according to an embodiment of the device 10.
Figure 6B:
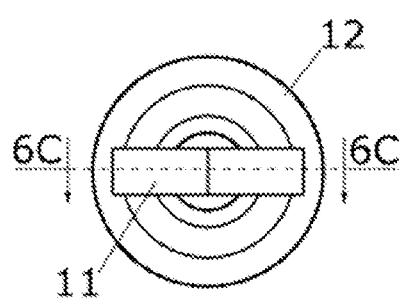
FIG. 6B illustrates a bottom view of the controller 11 connected to the threaded shaft 13 inside the housing 12 according to an embodiment of the device 10.
Figure 6C:
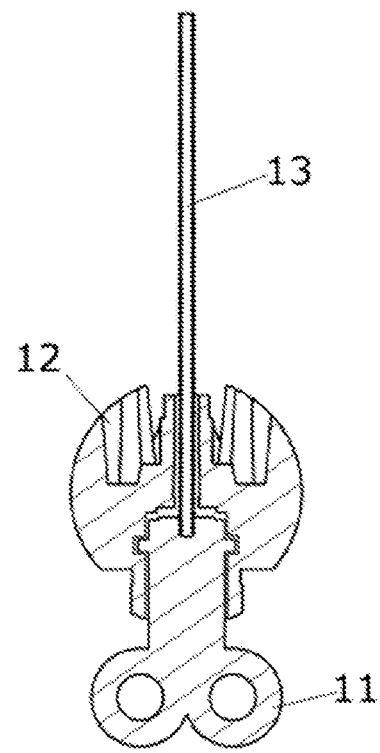
FIG. 6C illustrates a section view of FIG. 6B.

In its preferred embodiment illustrated in FIG. 5A and FIG. 5D, the controller 11 has a first end 11A and a second end 11B. Preferably, the controller first end 11A is connected to the second end 11B, such that when the first end 11A is rotated by the user, the second end 11B rotates following the rotation of the first end 11A. As illustrated in FIG. 5C, the second end 11B preferably connects the first end 13A of the threaded shaft 13 (illustrated in FIG. 5B), such that when the second end 11B rotates, the threaded shaft 13 rotates following the rotation of the second end 11B. Preferably, the second end 11B of the controller 11 and the first end 13A of the threaded shaft 13 are configured to fit inside the housing 12, wherein the second end 11B of the controller 11 and the first end 13A of the threaded shaft 13 can only rotate clockwise or counter-clockwise around the longitudinal axis of the threaded shaft 13, as illustrated in FIG. 6. FIG. 6A illustrates a perspective view of the connection between the controller 11 and the threaded shaft 13 inside the housing 12 in a preferred embodiment. FIG. 6B illustrates a bottom view of the connection between the controller 11 and the threaded shaft 13 inside the housing 12 in a preferred embodiment. FIG. 6C illustrates a section view of FIG. 6B.

Figure 7A:
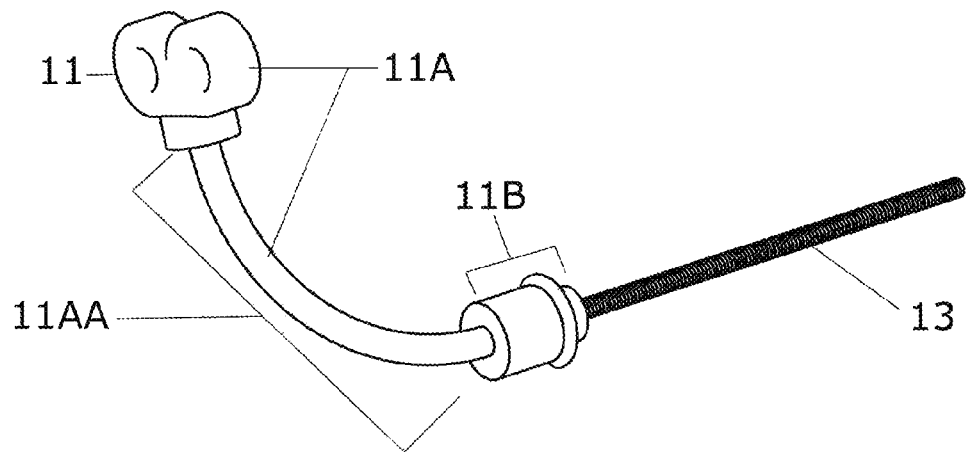
FIG. 7A illustrates a perspective view of the controller 11 connected to the threaded shaft 13 according to an embodiment of the device 10.
Figure 7B:
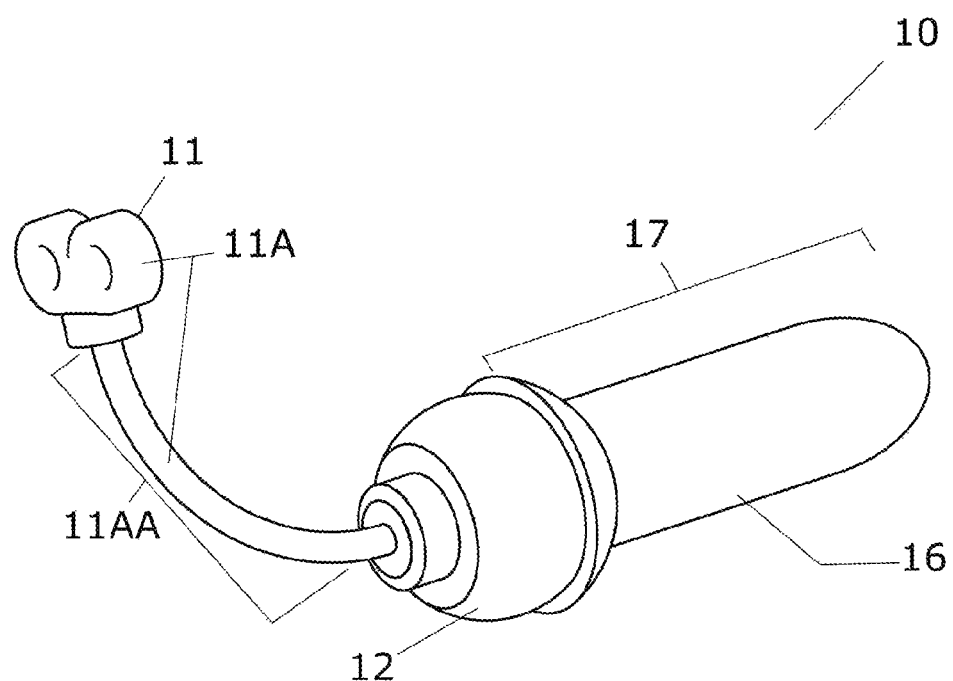
FIG. 7B illustrates a perspective view of the device 10 with the shaft 17 at its minimum girth according to an embodiment of the device 10.
Figure 41:
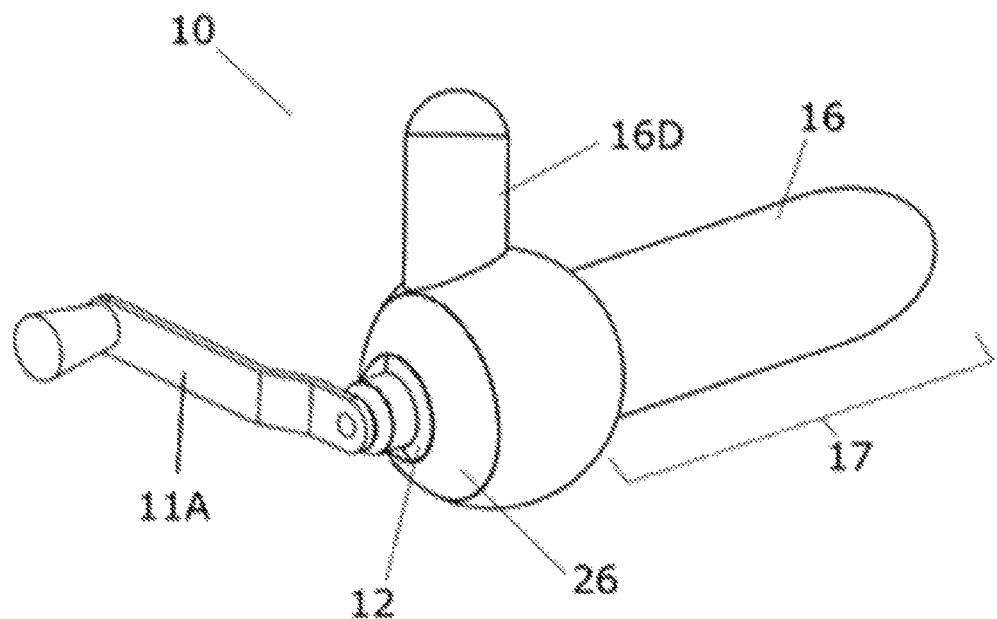
FIG. 41 illustrates a perspective view of the device 10 with the shaft 17 at its minimum girth according to an embodiment of the device 10.

Preferably, the first end 11A of the controller 11 is configured with an ergonomic shape that facilitates its control by the user with one or both hands. Preferably, the controller 11 is made with at least one coloration additive, however, the controller 11 may be made with no coloration additive. Preferably, the first end 11A of the controller 11 is configured in a geometric shape approximately or precisely, such as, but not limited to: a key shape, a suction cup shape (as illustrated in FIG. 18), a knob shape (as illustrated in FIG. 19A), a cylinder shape, a heart shape, an animal tail shape, a knuckle punch shape, a polyhedron shape, a gemstone shape, a human face shape, an animal face shape, and/or a potatoid shape. The first end 11A of the controller 11 may be configured as a flexible shaft, a coupling nut, a motor shaft coupler, a crank handle (as illustrated in FIG. 41), a foldable crank handle, and a wrench. Preferably, the controller 11 is made with a rigid material such as, but not limited to: plastic, plastic-based, hard silicone, iron-based metal, metal, magnet 31, glass and/or wood material, however, the controller 11 may be made in combination with a soft material such as, but not limited to: silicone, silicone-based, leather, and/or rubber material. The first end 11A may be configured with a flexible section 11AA as illustrated in FIG. 7, such that when the first end 11A configured with a flexible section 11AA is rotated clockwise or counter-clockwise by the user, the second end 11B and the threaded shaft 13 rotate following the rotation of the first end 11A configured with a flexible section 11AA. The controller 11 may be configured with a color code and/or a serial number to distinguish a device 10 with one configuration, one girth adjustment performance and/or one size from another device 10 having another configuration, girth adjustment performance and/or size, to facilitate the utilization for the user of several devices 10. The controller 11 may be configured with at least one visual and/or tactile indication to indicate to the user how to use the device 10.

Figure 8:
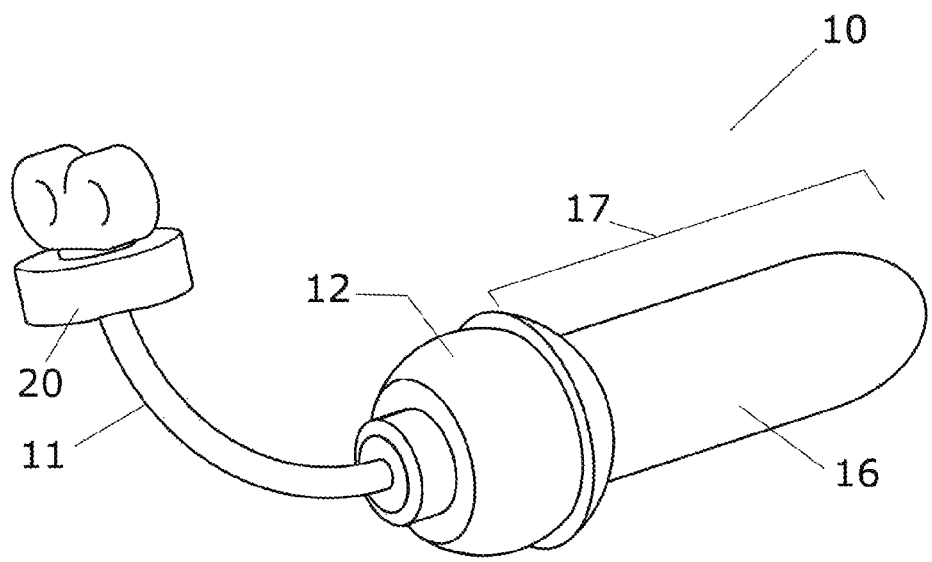
FIG. 8 illustrates a perspective view of the device 10 with the shaft 17 at its minimum girth according to an embodiment of the device 10.

In another embodiment, as illustrated in FIG. 8, the controller 11 may comprise at least one handle having a bearing 20. Preferably, the handle having a bearing 20 comprises at least one such as, but not limited to: a plain bearing and/or a rolling-element bearing. This embodiment is an alternative for the utilization of the controller 11, as the user with one hand can hold the controller 11 and with the other hand can rotate the first end 11A of the controller 11 to perform the adjustment of the device 10. FIG. 8 illustrates a perspective view of the device 10 with the shaft 17 at its minimum girth in this embodiment.

Figure 9:
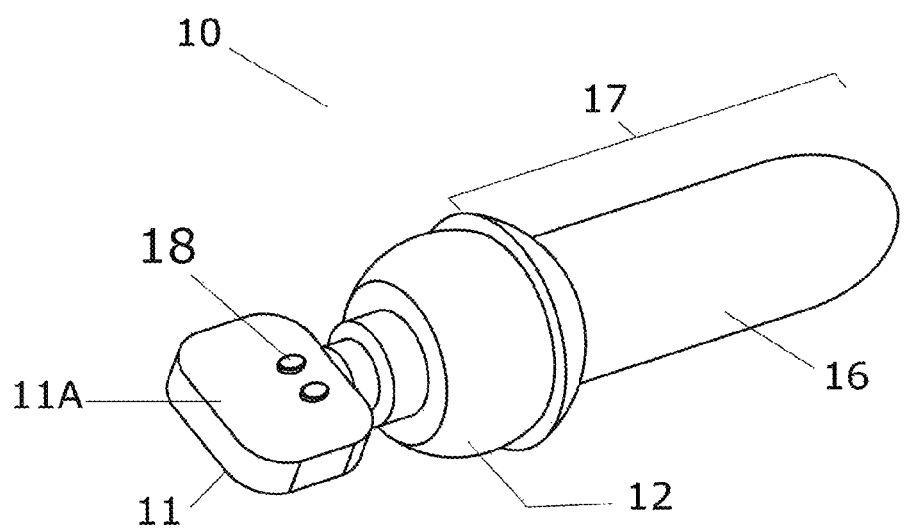
FIG. 9 illustrates a perspective view of the device 10 with the shaft 17 at its minimum girth according to an embodiment of the device 10.

In another embodiment as illustrated in FIG. 9, the controller 11 may comprise at least one electronic part 18. Preferably in this embodiment, the user operates the electronic part 18 via the controller 11. FIG. 9 illustrates a perspective view of the device 10 with the shaft 17 at its minimum girth in this embodiment.

Figure 10A:
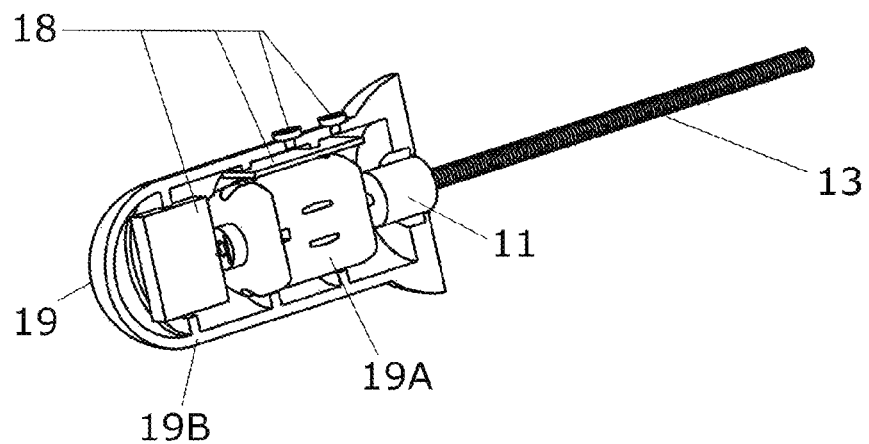
FIG. 10A illustrates a perspective view of the enclosed electric motor 19 (only one part of the motor housing 19B is illustrated in FIG. 10A) connected to the controller 11, which is connected to the threaded shaft 13 according to an embodiment of the device 10.
Figure 10B:
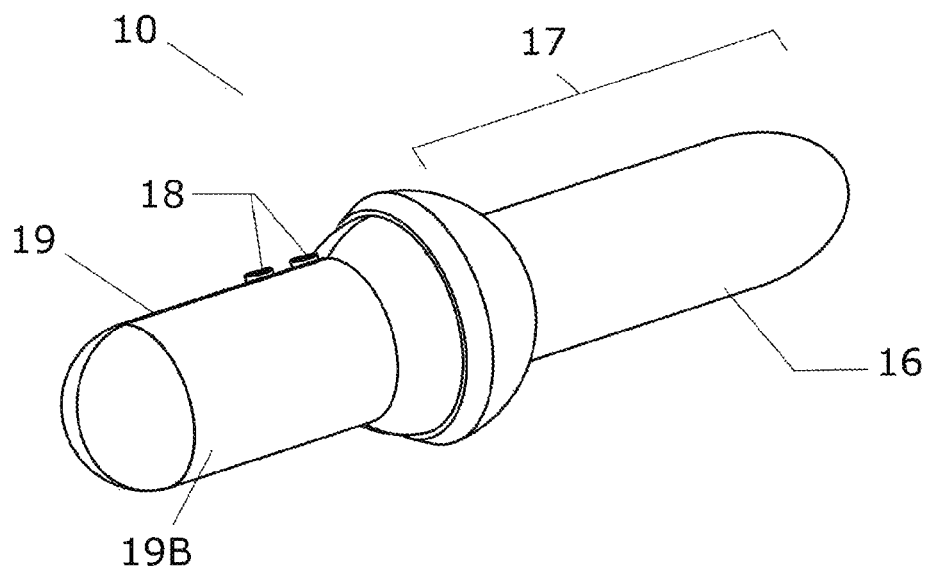
FIG. 10B illustrates a perspective view of the device 10 with the shaft 17 at its minimum girth according to an embodiment of the device 10.
Figure 11:
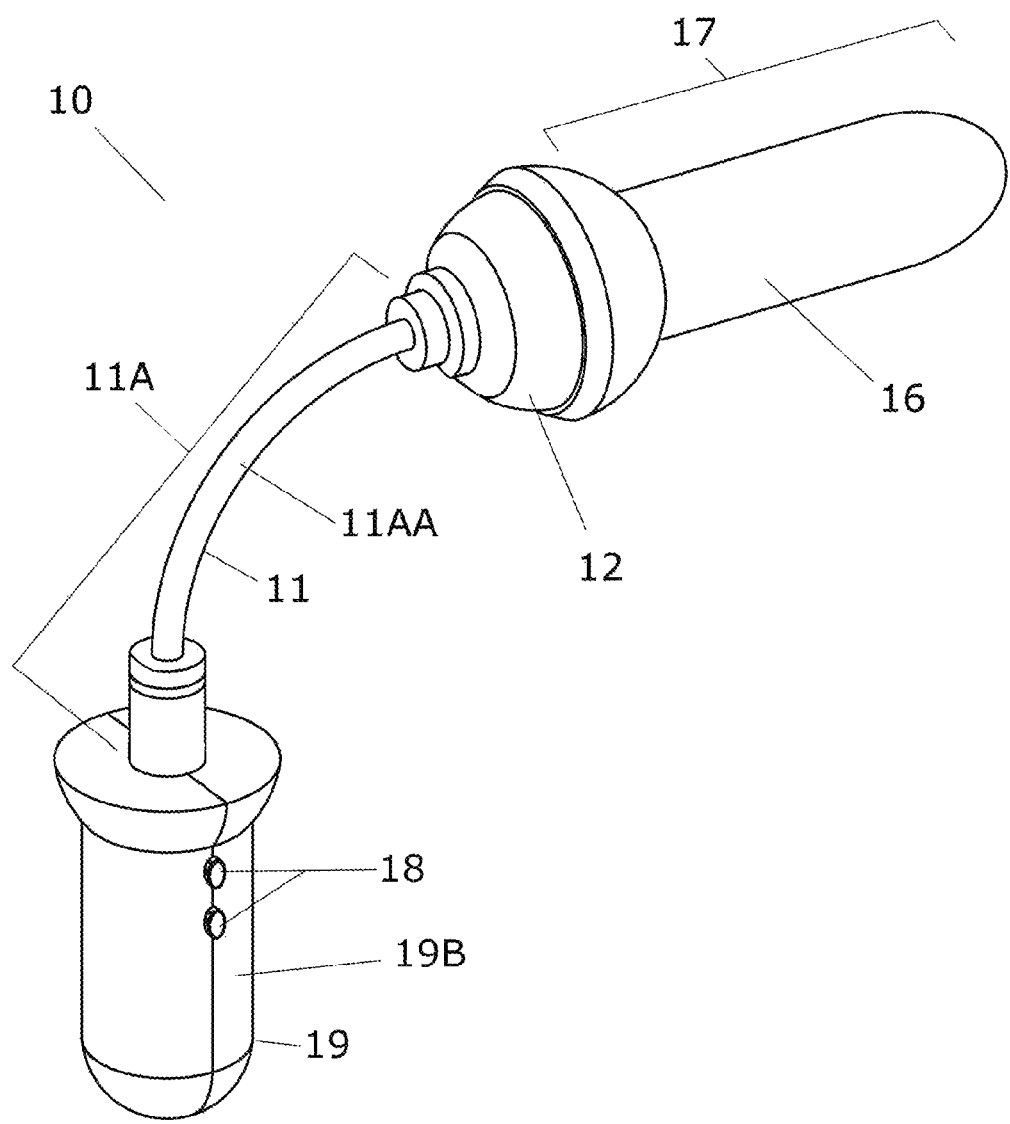
FIG. 11 illustrates a perspective view of the device 10 with the shaft 17 at its minimum girth according to an embodiment of the device 10.

In another embodiment, as illustrated in FIG. 10 and FIG. 11, the device 10 may comprise an enclosed electric motor 19. In the embodiment illustrated in FIG. 10, the motor housing 19B of the enclosed electric motor 19 is connected to the housing 12, the motor shaft of the motor having a motor shaft 19A of the enclosed electric motor 19 is connected to the first end 11A of the controller 11, such that when the motor shaft of the motor having a motor shaft 19A is rotated clockwise or counter-clockwise by the user via the electronic part 18 of the enclosed electric motor 19, the first end 11A and the second end 11B of the controller 11, rotate following the rotation of the motor shaft of the motor having a motor shaft 19A of the enclosed electric motor 19. The second end 11B of the controller 11 is connected to threaded shaft 13, such that when the second 11B of the controller 11 rotates, the threaded shaft 13 rotates following the rotation of the second 11B of the controller 11. In the embodiment illustrated in FIG. 11, the enclosed electric motor 19 is connected to the first end 11A configured with a flexible section 11AA of the controller 11, such that when the motor shaft of the motor having a motor shaft 19A of the enclosed electric motor 19 is rotated clockwise or counter-clockwise by the user via the electronic part 18 of the enclosed electric motor 19, the first end 11A configured with a flexible section 11AA, and the second end 11B of the controller 11 rotate following the rotation of the motor shaft of the motor having a motor shaft 19A of the enclosed electric motor 19. The second end 11B of the controller 11 is connected to threaded shaft 13, such that when the second 11B of the controller 11 rotates, the threaded shaft 13 rotates following the rotation of the second 11B of the controller 11. FIG. 10A illustrates the enclosed electric motor 19 (only one part of the motor housing 19B is illustrated in FIG. 10A) connected to the controller 11, which is connected to the threaded shaft 13 in this embodiment. FIG. 10B illustrates the device 10 with the shaft 17 at its minimum girth in this embodiment. FIG. 11 illustrates the device 10 with the shaft 17 at its minimum girth in this embodiment.

Figure 12A:
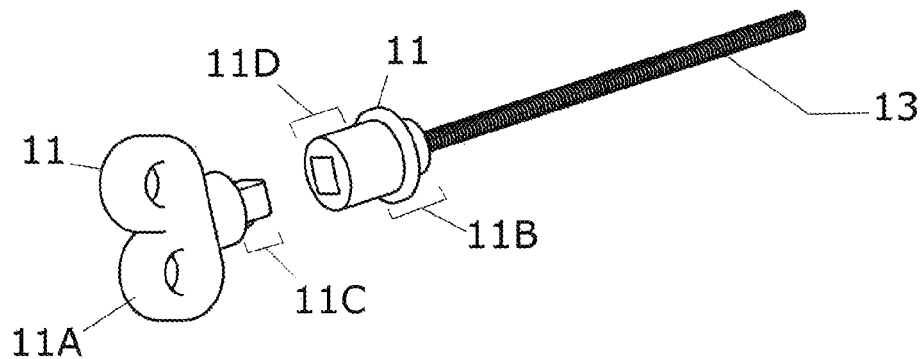
FIG. 12A illustrates a perspective view of the controller 11 connected to the threaded shaft 13 according to an embodiment of the device 10.
Figure 12B:
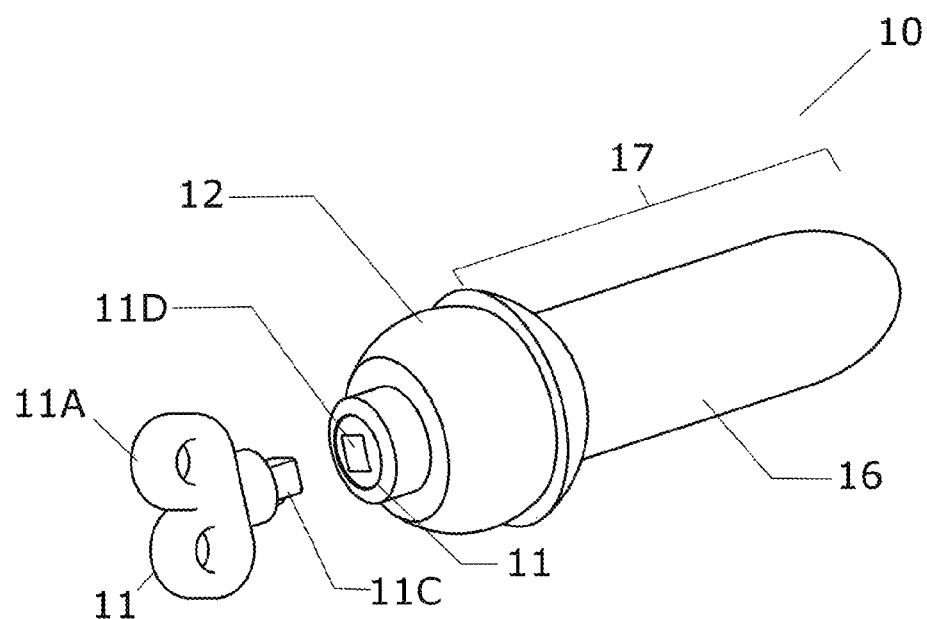
FIG. 12B illustrates a perspective view of the device 10 with the shaft 17 at its minimum girth iso according to an embodiment of the device 10.
Figure 19B:
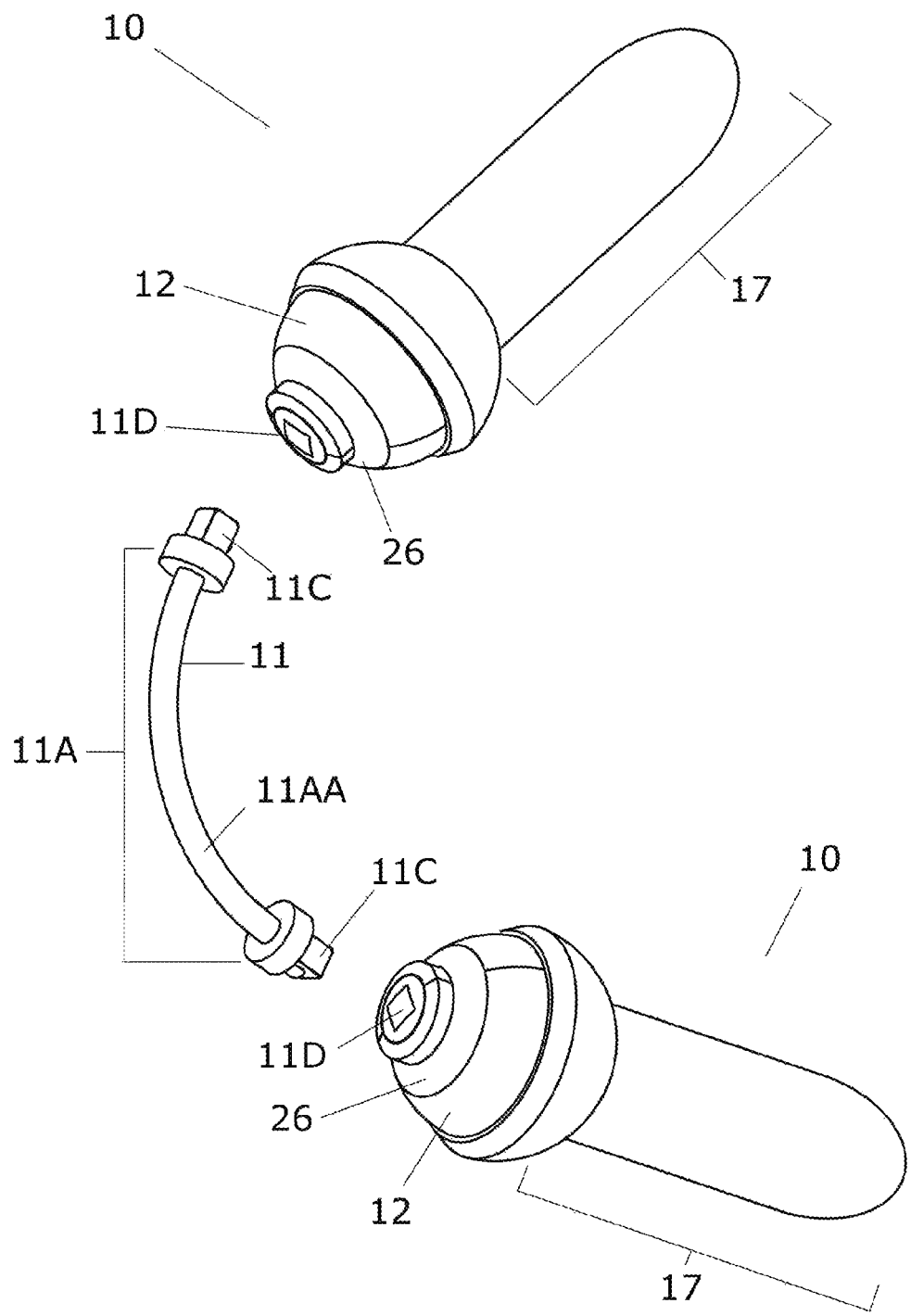
FIG. 19B illustrates a perspective view of two devices 10 with the shaft 17 at its minimum girth according to an embodiment of the device 10.

In another embodiment as illustrated from FIG. 12 to FIG. 18 and in FIG. 19B, the controller 11 may comprise at least one male connection 11C and at least one female connection 11D. Preferably, the female connection 11D is configured such as, but not limited to: a socket wrench type, a keyhole type or a screw drive type such as, but not limited to: slotted type, cruciform type, polygon type, hexablobular type, three-pointed type, clutch, one-way type, bristol type, quadrex type, pentalobe type and/or spanner head screw drive type. Preferably, the male connection 11C and the female connection 11D are made of such as, but not limited to: plastic, plastic-based, iron-based metal, metal, magnetic, and/or ferromagnetic material. Attention being called to the fact that, when the male connection 11C and the female connection 11D are made with a magnetic and/or ferromagnetic material, it facilitates by magnetic attraction, the connection between the male connection 11C and the female connection 11D. Preferably, the male connection 11C is configured to removably fit into the female connection 11D, which means that the male connection 11C may be repeatedly connected to the female connection 11D, then removed from the female connection 11D, and then connected again to the female connection 11D, and such that when the male connection 11C is connected to the female connection 11F and when the male connection 11C rotates clockwise or counter-clockwise, the female connection 11F rotates following the rotation of the male connection 11C. As illustrated in FIG. 12, the first end 11A is preferably connected to the male connection 11C, and the female connection 11D is preferably connected to the second end 11B, such that when the male connection 11C is connected to the female connection 11D, and when the first end 11A is rotated clockwise or counter-clockwise by the user, the second end 11B rotates following the rotation of the first end 11A. The second end 11B of the controller 11 is connected to the threaded shaft 13, such that when the second 11B of the controller 11 rotates, the threaded shaft 13 rotates following the rotation of the second 11B of the controller 11. FIG. 12A illustrates the controller 11 connected to the threaded shaft 13 in this embodiment. FIG. 12B illustrates the device 10 with the shaft 17 at its minimum girth according to this embodiment.

Figure 13A:
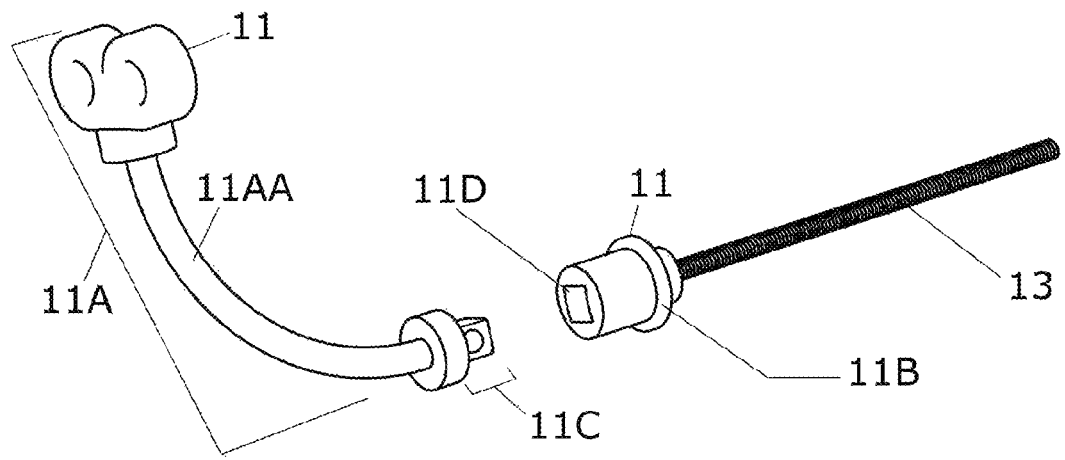
FIG. 13A illustrates a perspective view of the controller 11 connected to the threaded shalt 13 according to an embodiment or the device 10.
Figure 13B:
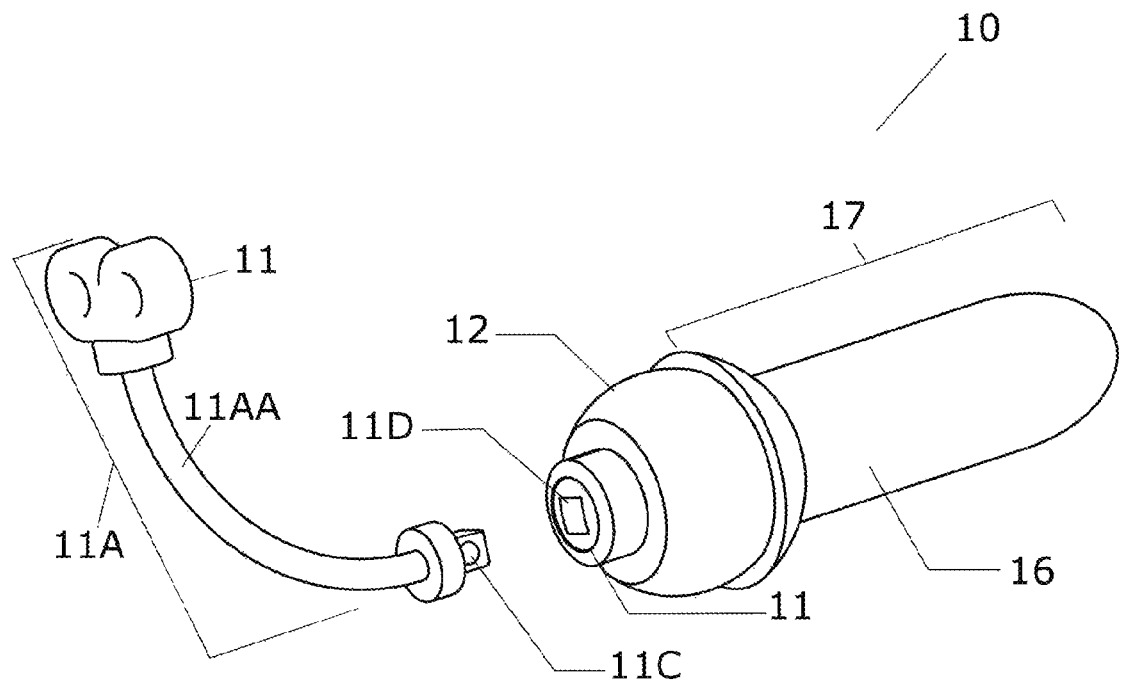
FIG. 13B illustrates a perspective view of the device 10 with the shaft 17 at its minimum girth according to an embodiment of the device 10.

As illustrated in FIG. 13, the first end 11A configured with the flexible section 11AA may be connected to the male connection 11C, such that when the first end 11A configured with the flexible section 11AA is rotated clockwise or counter-clockwise by the user, and when the male connection 11C is connected to the female connection 11D, the second end 11B rotates following the rotation of the first end 11A configured with the flexible section 11AA. The second end 11B of the controller 11 is connected to threaded shaft 13, such that when the second 11B of the controller 11 rotates, the threaded shaft 13 rotates following the rotation of the second 11B of the controller 11. FIG. 13A illustrates the controller 11 connected to the threaded shaft 13 in this embodiment. FIG. 13B illustrates the device 10 with the shaft 17 at its minimum girth according to this embodiment.

Figure 14A:
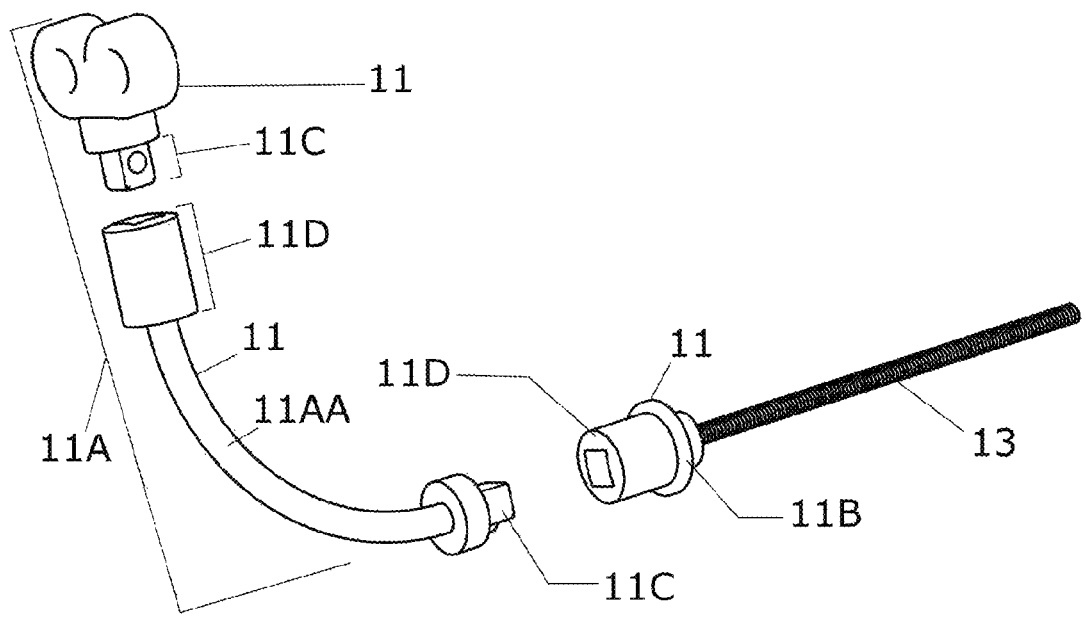
FIG. 14A illustrates a perspective view of the controller 11 connected to the threaded shaft 13 according to an embodiment of the device 10.
Figure 14B:
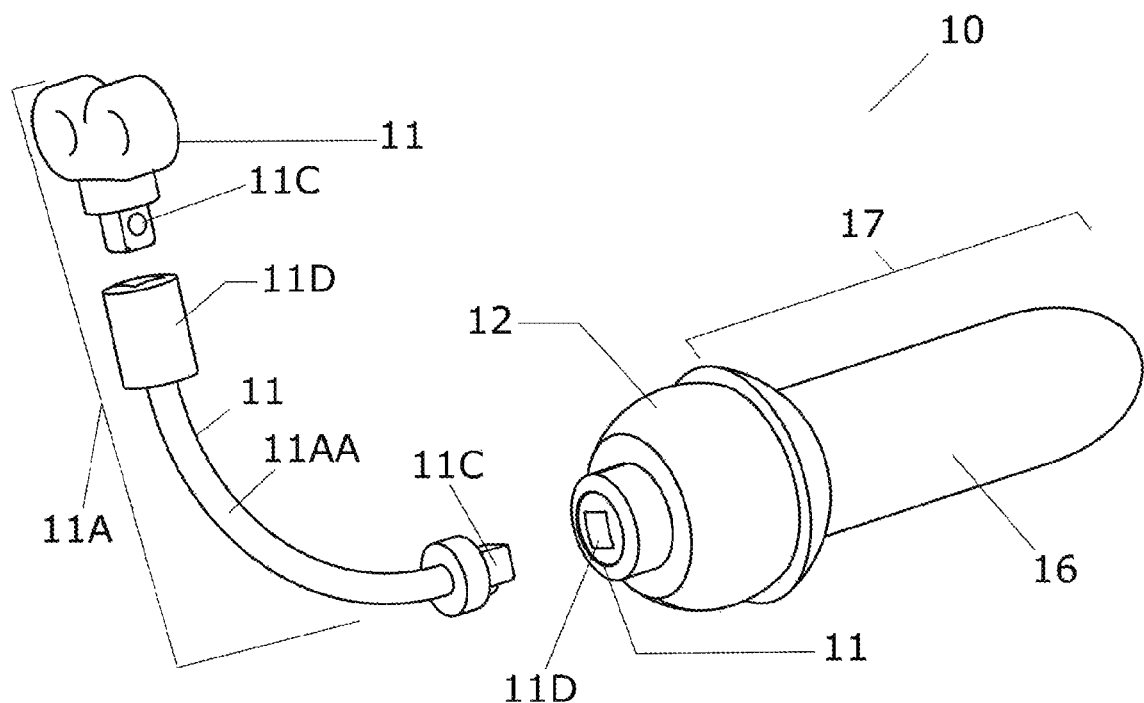
FIG. 14B illustrates a perspective view of the device 10 with the shaft 17 at its minimum girth according to an embodiment of the device 10.

As illustrated in FIG. 14, the first end 11A configured with the flexible section 11AA may comprise two male connections 11C and two female connections 11D, such that when a first male connection 11C is connected to a first female connection 11D, and a second male connection 11C is connected to a second female connection 11D, and when the first end 11A configured with the flexible section 11AA is rotated clockwise or counter-clockwise by the user, the second end 11B rotates following the rotation of the first end 11A configured with the flexible section 11AA. The second end 11B of the controller 11 is connected to threaded shaft 13, such that when the second 11B of the controller 11 rotates, the threaded shaft 13 rotates following the rotation of the second 11B of the controller 11. FIG. 14A illustrates the controller 11 connected to the threaded shaft 13 in this embodiment. FIG. 14B illustrates the device with the shaft 17 at its minimum girth according to this embodiment.

Figure 15A:
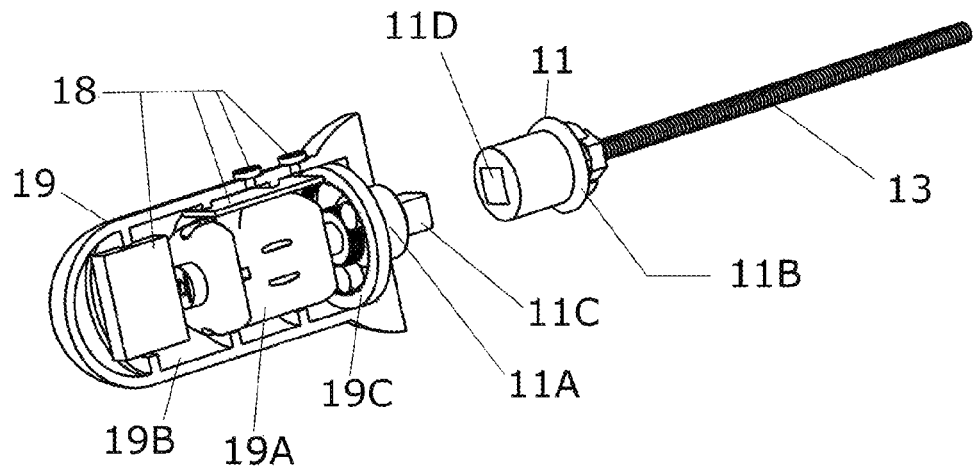
FIG. 15A illustrates a perspective view of the enclosed electric motor 19 (only one part of the motor housing 19B is illustrated in FIG. 15A) connected the controller 11, which is connected to the threaded shaft 13 according to an embodiment of the device 10.
Figure 15B:
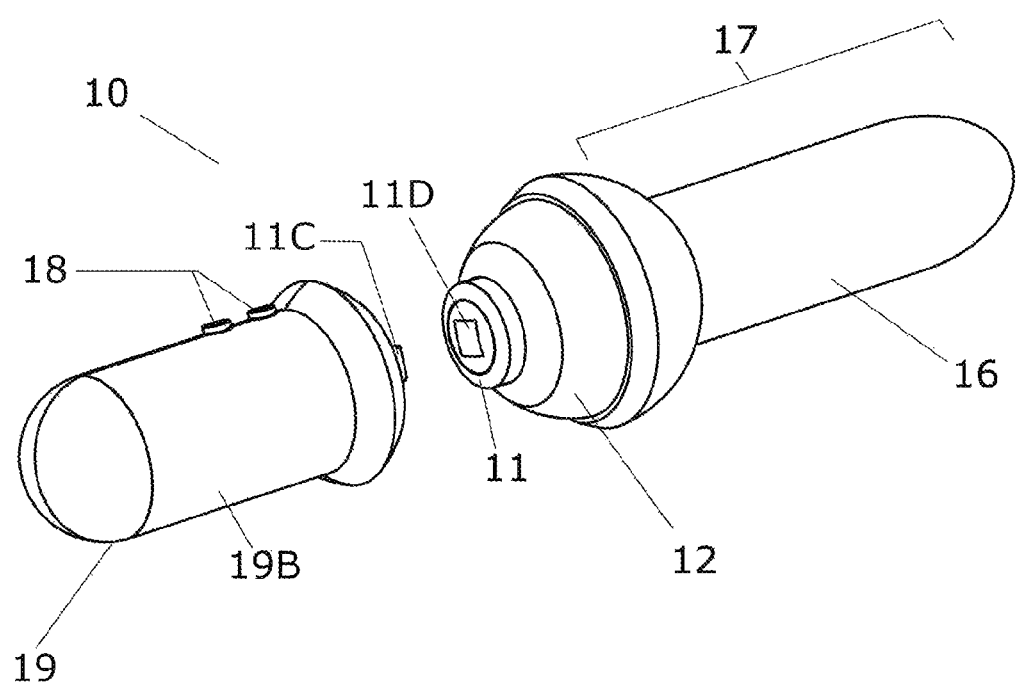
FIG. 15B illustrates a perspective view of the device 10 with the shaft 17 at its minimum girth according to an embodiment of the device 10.

As illustrated in FIG. 15, in the embodiment of the device 10 comprising an enclosed electric motor 19, the motor shaft of the motor having a motor shaft 19A of the enclosed electric motor 19 may be connected to the first end 11A of the controller 11, the first end 11A may be connected to the male connection 11C, the female connection 11D may be connected to the second end 11B, such that when the male connection 11C is connected to the female connection 11D, and when the motor shaft of the motor having a motor shaft 19A of the enclosed electric motor 19 is rotated by the user via the electronic part 18 of the enclosed electric motor 19, the first end 11A and the second end 11B of the controller 11 rotate following the rotation of the motor shaft of the motor having a motor shaft 19A of the enclosed electric motor 19. The second end 11B of the controller 11 is connected to threaded shaft 13, such that when the second 11B of the controller 11 rotates, the threaded shaft 13 rotates following the rotation of the second 11B of the controller 11. FIG. 15A illustrates the enclosed electric motor 19 (only one part of the motor housing 19B is illustrated in FIG. 15A) connected to the controller 11, which is connected to the threaded shaft 13 in this embodiment. FIG. 15B illustrates the device 10 with the shaft 17 at its minimum girth according to this embodiment.

Figure 16:
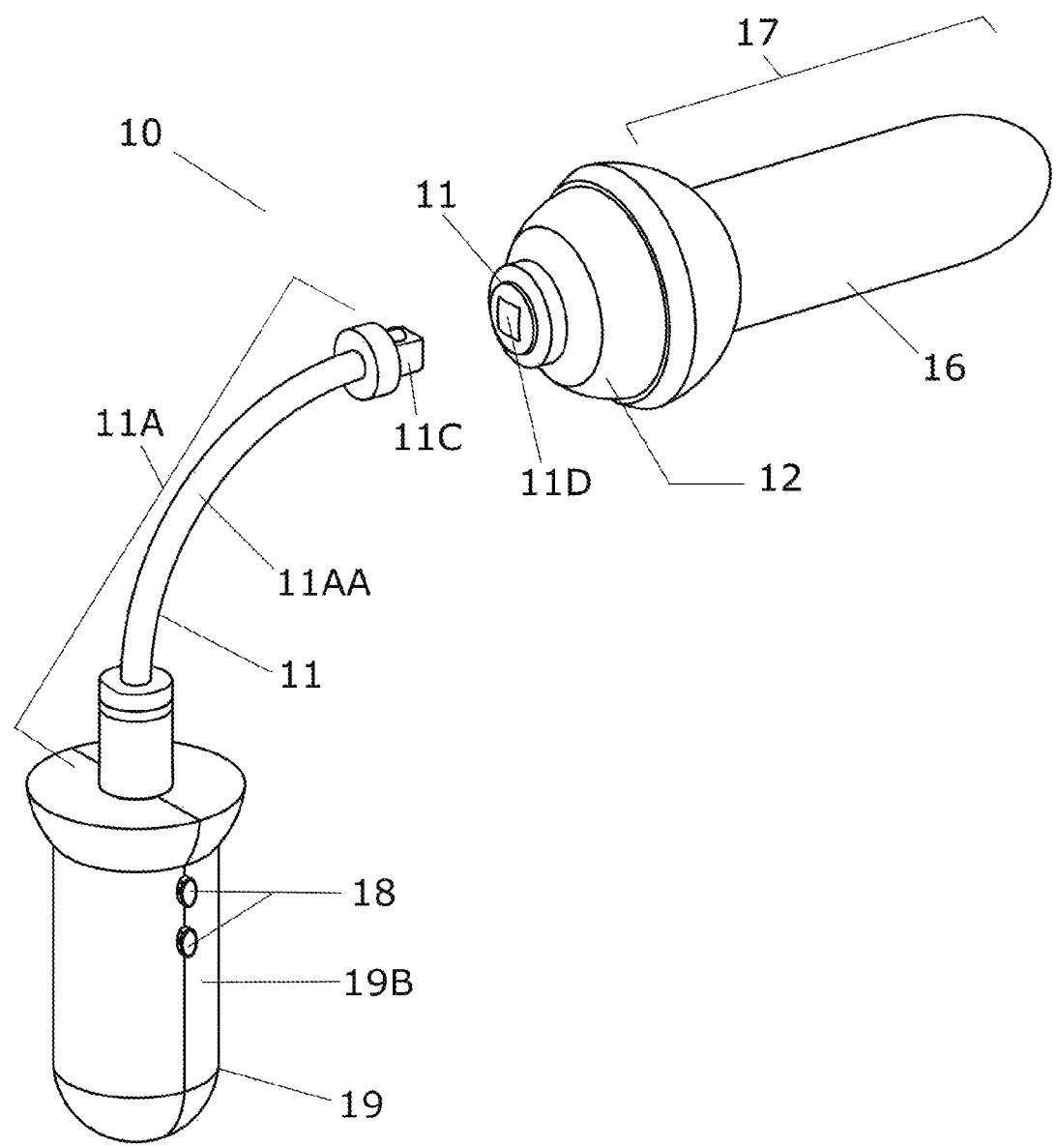
FIG. 16 illustrates a perspective view of the device 10 with the shaft 17 at its minimum girth according to an embodiment of the device 10.

As illustrated in FIG. 16, in the embodiment of the device 10 comprising an enclosed electric motor 19, the motor shaft of the motor having a motor shaft 19A of the enclosed electric motor 19 may be connected to the first end 11A configured with the flexible section 11AA of the controller 11, the first end 11A configured with the flexible section 11AA may be connected to the male connection 11C, the female connection 11D may be connected to the second end 11B, such that when the male connection 11C is connected to the female connection 11D, and when the motor shaft of the motor having a motor shaft 19A (not illustrated in FIG. 16) of the enclosed electric motor 19 is rotated clockwise or counter-clockwise by the user via the electronic part 18 of the enclosed electric motor 19, the first end 11A configured with the flexible section 11AA and the second end 11B of the controller 11 rotate following the rotation of the motor shaft of the motor having a motor shaft 19A (not illustrated in FIG. 16) of the enclosed electric motor 19. The second end 11B of the controller 11 is connected to threaded shaft 13, such that when the second 11B of the controller 11 rotates, the threaded shaft 13 rotates following the rotation of the second 11B of the controller 11. FIG. 16 illustrates the device 10 with the shaft 17 at its minimum girth according to this embodiment.

Figure 17:
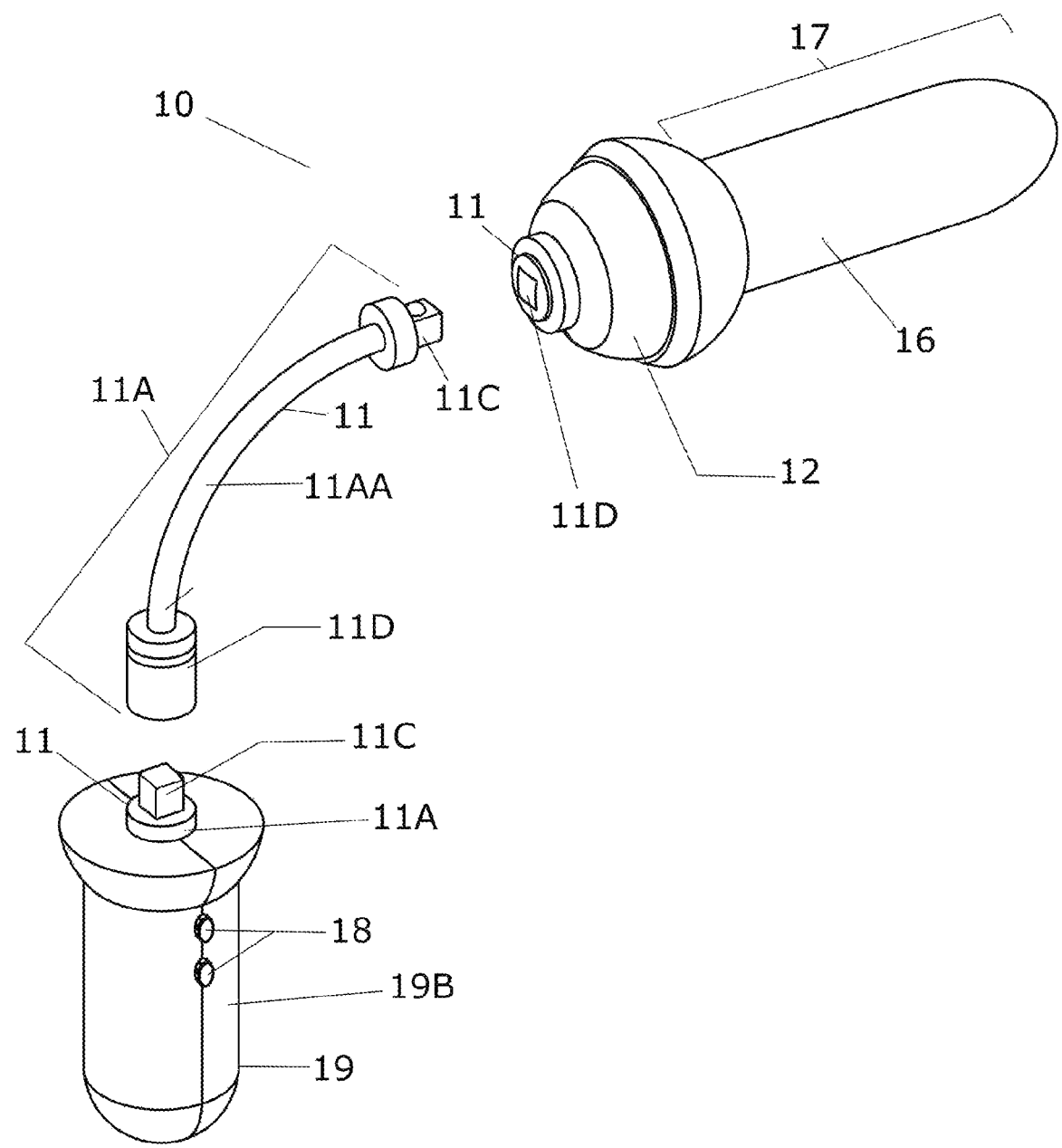
FIG. 17 illustrates a perspective view of the device 10 with the shaft 17 at its minimum girth according to an embodiment of the device 10.

As illustrated in FIG. 17, in the embodiment of the device 10 comprising an enclosed electric motor 19, the first end 11A configured with the flexible section 11AA may comprise two male connections 11C and two female connections 11D, such that when a first male connection 11C is connected to a first female connection 11D, and a second male connection 11C is connected to a second other female connection 11D, and when the when the motor shaft of the motor having a motor shaft 19A (not illustrated in FIG. 17) of the enclosed electric motor 19 is rotated clockwise or counter-clockwise by the user via the electronic part 18 of the enclosed electric motor 19, the first end 11A configured with the flexible section 11AA and the second end 11B of the controller 11 rotate following the rotation of the motor shaft of the motor having a motor shaft 19A (not illustrated in FIG. 17) of the enclosed electric motor 19. The second end 11B of the controller 11 is connected to threaded shaft 13, such that when the second 11B of the controller 11 rotates, the threaded shaft 13 rotates following the rotation of the second 11B of the controller 11, FIG. 17 illustrates the device 10 with the shaft 17 at its minimum girth according to this embodiment.

As illustrated in FIG. 19B, the first end 11A configured with the flexible section 11AA may comprise two male connections 11C and one female connections 11D, such that when a first male connection 11C is connected to the female connection 11D, and the second male connection 11C is connected to a female connection 11D of another device 10, (other device 10 in which its first end 11A having one male connection 11C of its controller 11 is not used and removed; other device 10 preferably comprising a threaded shaft 13 left-handed threaded; threaded shaft 13 left-handed threaded described in Threaded shaft section), and when the first end 11A configured with the flexible section 11AA of the device 10 is rotated clockwise or counter-clockwise by the user, the second end 11B of the device 10 and the second end 11B of the other device 10 rotate following the rotation of the first end 11A configured with the flexible section 11AA of the controller 11 of the device 10. FIG. 19B illustrates a perspective view of two devices 10 in this embodiment.

In another embodiment as illustrated in FIG. 20, the controller 11 having at least one male connection 11C and at least one female connection 11D may comprise at least one locking system 21. The locking system 21 removably secures the male connection 11C to the female connection 11D, which means that the male connection 11C may be repeatedly secured to the female connection 11D, then removed from the female connection 11D, and then secured again to the female connection 11D. The locking system 21 is preferably an easy release system such as, but not limited to: a spring-loaded system. This embodiment enhances the utilization of the device 10 for the user to prevent undesired disconnection of the controller 11 during the utilization of the device 10. The user operates the locking system 21 via the controller 11. FIG. 10 illustrates a perspective view of the device 10 with the shaft 17 at its minimum girth in this embodiment. FIG. 20A illustrates a perspective view of the device 10 with the shaft 17 at its minimum girth in this embodiment. FIG. 20B illustrates a front view of the controller 11 in this embodiment. FIG. 20C illustrates a side view of the controller 11 in this embodiment.

In another embodiment (not illustrated), the controller 11 or only the second end 11B of the controller 11 may be manufactured with the threaded shaft 13 as one part. This embodiment is an alternative for manufacturing optimization of the device 10.

Figure 21A:
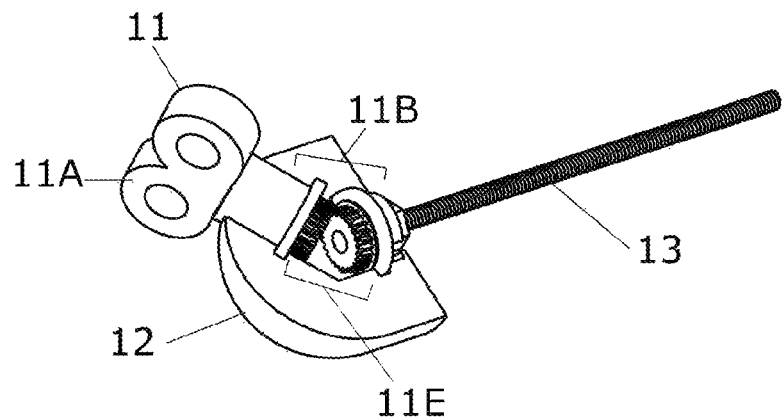
FIG. 21A illustrates a perspective view of the controller 11 connected to the threaded shaft 13 inside the housing 12 (only one part of the housing 12 is illustrated in FIG. 21A) according to an embodiment of the device 10.
Figure 21B:
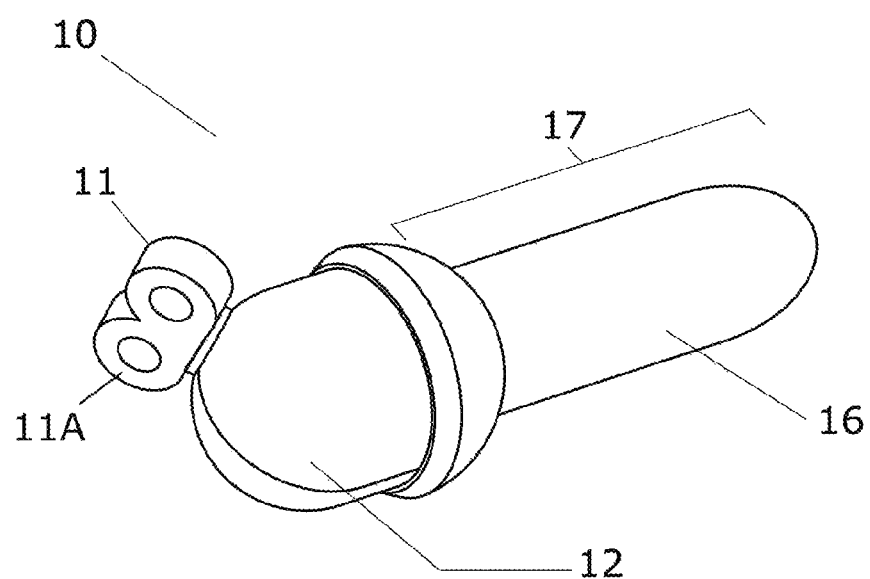
FIG. 21B illustrates a perspective view of the device 10 with the shaft 17 at its minimum girth according to an embodiment of the device 10.

In another embodiment, as illustrated in FIG. 21, the controller 11 may comprise at least one controller angular transmission 11E. The controller angular transmission 11E may be configured with a plurality of gears as illustrated in FIG. 21, or gearless (not illustrated). Preferably, the controller angular transmission 11E is configured to create an angle greater than or equal to 0.1° with the longitudinal axis of the threaded shaft 13, in the controller 11. Preferably, the controller 11 having at least one controller angular transmission 11E is connected to the threaded shaft 13, such that when the controller 11 having at least one controller angular transmission 11E rotates, the threaded shaft 13 rotates following the rotation of the second end 11B. The controller 11 having at least one controller angular transmission 11E reduces the distance to reach the controller 11 for the user and therefore facilitates the utilization of the device 10. FIG. 21A illustrates the connection between the controller 11 and the threaded shaft 13 inside the housing 12 (only one part of the housing 12 is illustrated in FIG. 21A) in this embodiment. FIG. 21B illustrates a perspective view of the device 10 with the shaft 17 at its minimum girth.

Threaded Shaft

In a preferred embodiment, the device 10 comprises one threaded shaft 13. The threaded shaft 13, as illustrated in FIG. 5B, has a first end 13A, a middle section 13B, a second end 13C, and a longitudinal axis. The direction of orientation going from the first end 13A to the second end 13C of the threaded shaft 13 is referred hereinafter to as "the longitudinal axis". Preferably, the first end 13A of the threaded shaft 13 is connected to the second end 11B of the controller 11 (as illustrated in FIG. 5C), such that when the second end 11B rotates clockwise or counter-clockwise, the threaded shaft 13 rotates following the rotation of the second end 11B of the controller 11. Preferably, the threaded shaft 13 is a threaded rod fastener configured with a length greater than 1 inch, a major diameter greater than 0.0730 inches, and with less than or equal to 160 threads per inch. The threads per inch of the threaded shaft 13 define partially the specific characteristics of the adjustment of the device 10. Preferably, the threaded shaft 13 is right-handed threaded, which means made with right-handed threads, however, the threaded shaft 13 may be left-handed threaded, which means made with left-handed threads, and therefore reversing the direction of rotation of the threaded shaft 13 to perform the adjustment of the device 10. Preferably, the threaded shaft 13 is made of such as, but not limited to: metal, iron-based metal, plastic, and/or plastic-based material.

In another embodiment, as illustrated in FIG. 22A, the threaded shaft 13 may comprise at least one clockwise translation stopper 13E made of such as, but not limited to: silicone, rubber, metal, iron-based metal, plastic and/or plastic-based material. The clockwise translation stopper 13E may be such as, but not limited to: a nut fastener, and/or a washer fastener. Preferably, the clockwise translation stopper 13E is secured on the threaded shaft 13. The clockwise translation stopper 13E is configured on the threaded shaft 13 to stop the module 14 from traveling along the threaded shaft 13 in the direction of the housing 12, and therefore to stop the clockwise rotation of the controller 11 when the adjustment reaches the maximum girth offered by the device 10. In this embodiment, the housing 12 and the shaft member 15 (not illustrated in this embodiment) are configured to receive the clockwise translation stopper 13E. The clockwise translation stopper 13E reduces friction and handling stress on the device 10 during the utilization by the user. FIG. 22A illustrates a front view of the device 10 (sheath 16 and the plurality of shaft member 15 not illustrated) with the shaft 17 at its maximum girth in this embodiment.

In another embodiment as illustrated in FIG. 22B, the threaded shaft 13 may comprise at least one counter-clockwise translation stopper 13F made of such as, but not limited to: silicone, rubber, metal, iron-based metal, plastic, and/or plastic-based material. The counter-clockwise translation stopper 13F may be such as, but not limited to: a nut fastener, and/or a washer fastener. Preferably, the counter-clockwise translation stopper 13F is secured on the threaded shaft 13. Preferably, the counter-clockwise translation stopper 13F is configured on the threaded shaft 13 to stop the module 14 from traveling along the threaded shaft 13 in the opposite direction of the housing 12, and therefore to stop the counter-clockwise rotation of the controller 11 when the adjustment reaches the minimum girth offered by the device 10. In this embodiment, the housing 12 and the shaft member 15 (not illustrated in this embodiment) are configured to receive the counter-clockwise translation stopper 13F. The counter-clockwise translation stopper 13F reduces friction and handling stress on the device 10 during the utilization by the user. The counter-clockwise translation stopper 13F may be configured such as, but not limited to: a cap nut fastener (illustrated in FIG. 22B), to protect the sheath 16 from the second end 13C. FIG. 22B illustrates a front view of the device 10 (sheath 16 and the plurality of shaft member 15 are not illustrated) with the shaft 17 at its minimum girth in this embodiment.

Figure 22C:
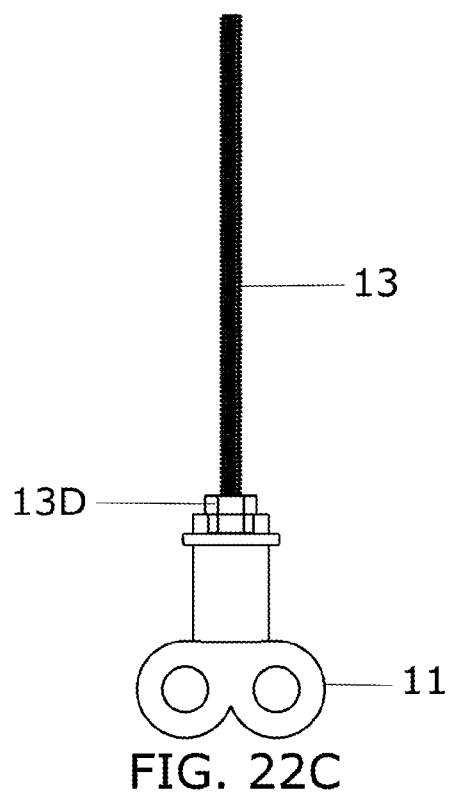
FIG. 22C illustrates the controller 11 connected to the threaded shaft 13 according to an embodiment of the device 10.

In another embodiment, as illustrated in FIG. 22C, the threaded shaft 13 may comprise at least one controller-connector 13D made of such as, but not limited to: metal, iron-based metal, magnet 31, plastic, and/or plastic-based material. The controller-connector 13D may be such as, but not limited to: a nut fastener, or a wing nut fastener. Preferably, the controller-connector 130 is configured at the first end 13A of the threaded shaft 13 and connects the second end 11B to the controller 11 to the threaded shaft 13. Preferably, the controller-connector 13D is secured on the threaded shaft 13. The controller-connector 13D reinforces the connection between the controller 11 and the threaded shaft 13, reduces friction and handling stress on the device 10 during the utilization. FIG. 22C illustrates a front view of the controller 11 connected to the threaded shaft 13 via the controller-connector 130 in this this embodiment.

Figure 23A:
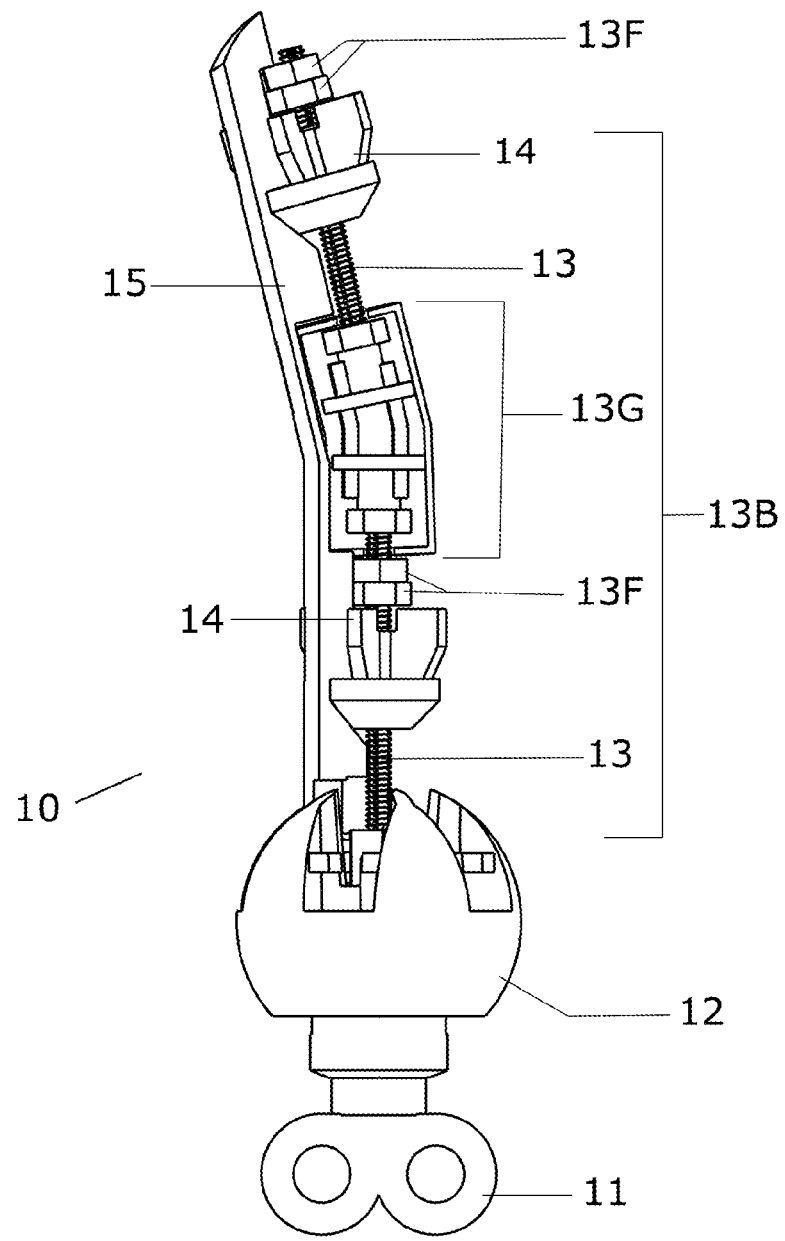
FIG. 23A illustrates a front view of the device 10 with the shaft 17 at its minimum girth according to an embodiment of the device 10 (sheath 16 not illustrated in FIG. 23A and only one shaft member 15 is illustrated in FIG. 23A).
Figure 23B:
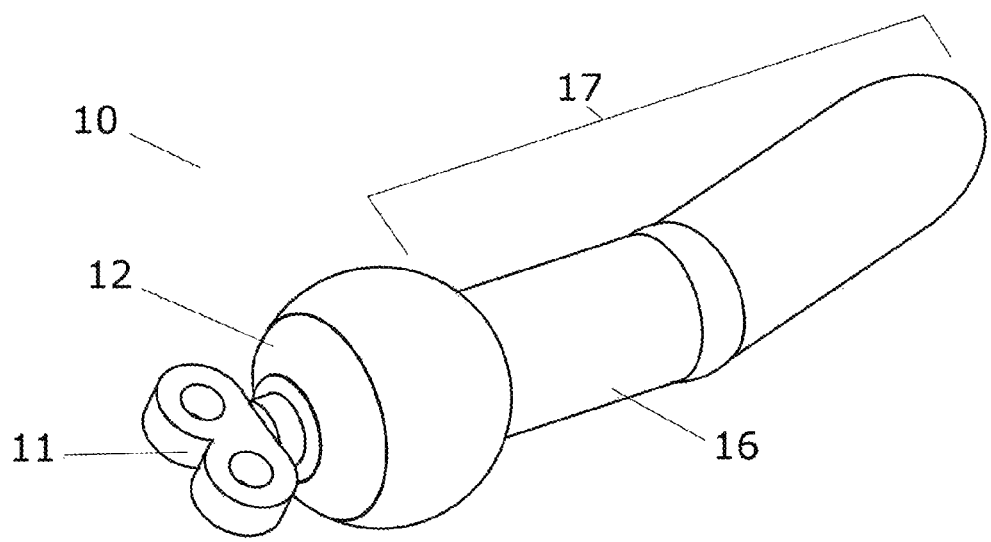
FIG. 23B illustrates a perspective view of the device 10 with the shaft 17 at its minimum girth according to an embodiment of the device 10.
Figure 23C:
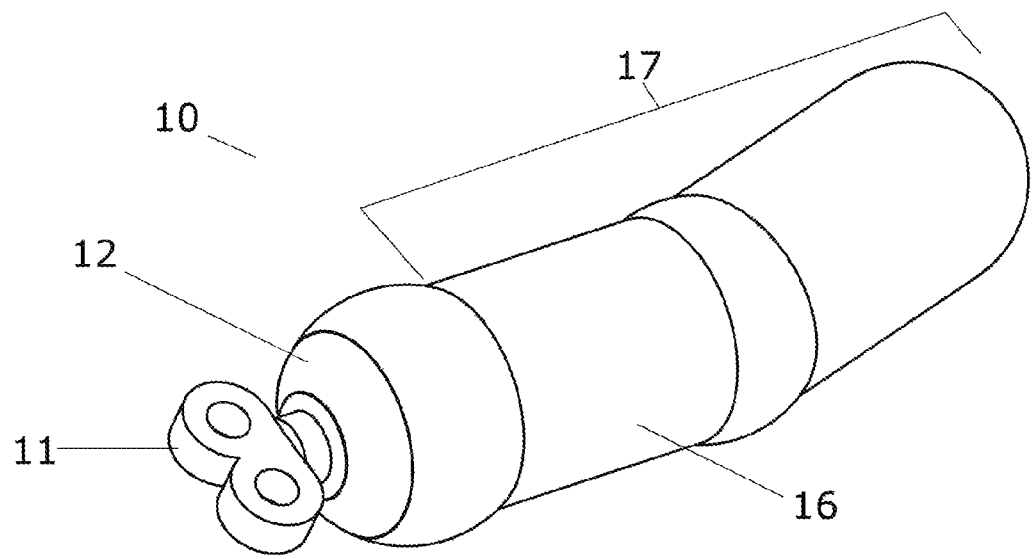
FIG. 23C illustrates a perspective view of the device 10 with the shaft 17 at its maximum girth according to an embodiment of the device 10.
Figure 24A:
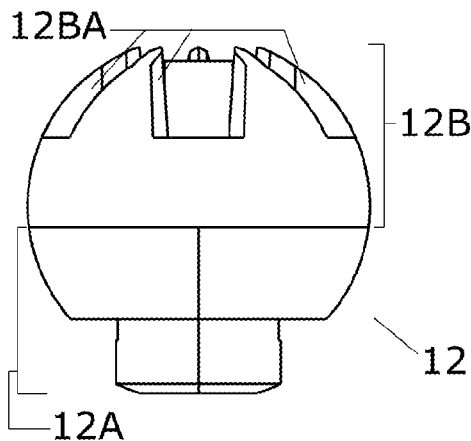
FIG. 24A illustrates a front view of the housing 12 according to an embodiment of the device 10.
Figure 24B:
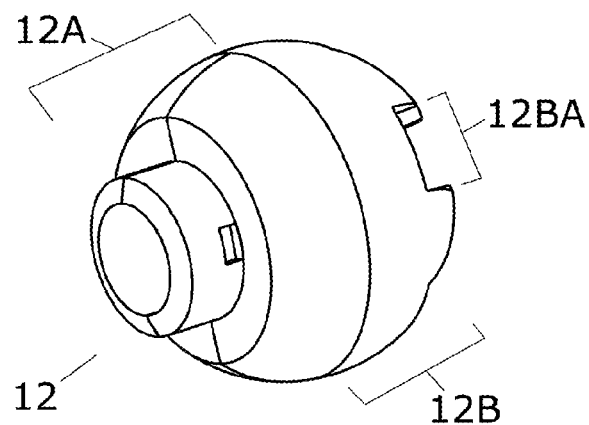
FIG. 24B illustrates a perspective view of the housing 12 according to an embodiment of the device 10.
Figure 24C:
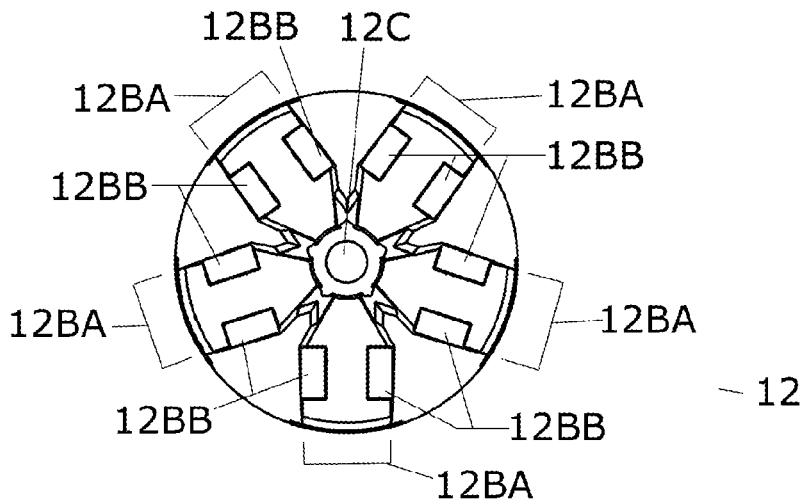
FIG. 24C illustrate a top view of the housing 12 according to an embodiment of the device 10.
Figure 24D:
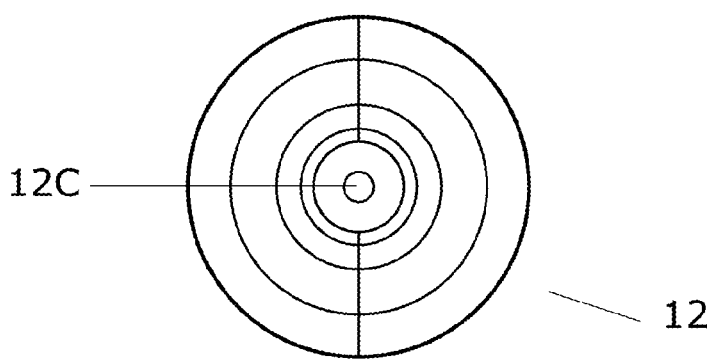
FIG. 24D illustrates a bottom view of the housing 12 according to an embodiment of the device 10.

In another embodiment, the threaded shaft 13 may comprise at least one threaded shaft angular transmission 13G. The threaded shaft angular transmission 13G may be configured with a plurality of gear (not illustrated), or gearless as illustrated in FIG. 23A. Preferably, the threaded shaft angular transmission 13G is configured to create an angle greater than or equal to 0.1° with the longitudinal axis of the threaded shaft 13, in the threaded shaft 13. The angular transmission 13G when located at the first end 13A of the threaded shaft 13 (not illustrated in this embodiment) reduces the distance to reach the controller 11 for the user and therefore facilitates the utilization of the device 10 and when the angular transmission 13G is located at the middle section 13B (as illustrated in FIG. 23), and/or the second end 13C (not illustrated in this embodiment) of the threaded shaft 13, provides other features to the user such as: prostate stimulation. In this embodiment, the shaft member 15 and the sheath 16 are configured to receive the threaded shaft 13 having at least one angular transmission 13G. FIG. 23A illustrates a front view of the device 10 with the shaft 17 at its minimum girth in this embodiment (sheath 16 not illustrated and only one shaft member 15 illustrated). FIG. 23B illustrates a perspective view of the device 10 with the shaft 17 at its minimum girth in this embodiment. FIG. 23C illustrates a perspective view of the device 10 with the shaft 17 at its maximum girth in this embodiment.

Housing

Figure 25A:
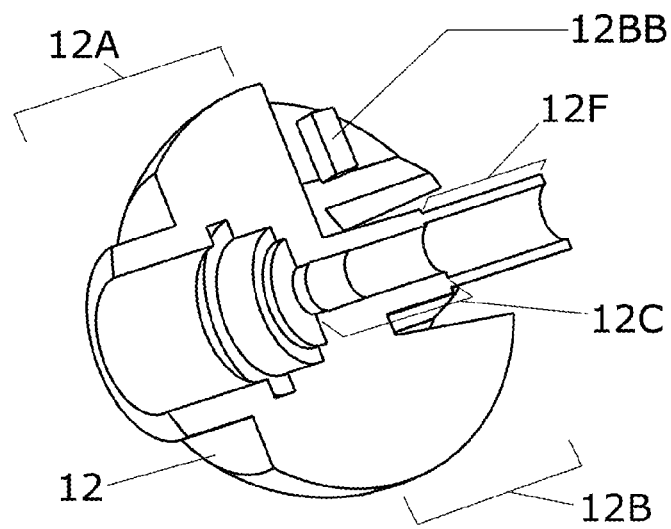
FIG. 25A illustrates a perspective view of a part of the housing 12 according to an embodiment of the device 10.
Figure 25B:
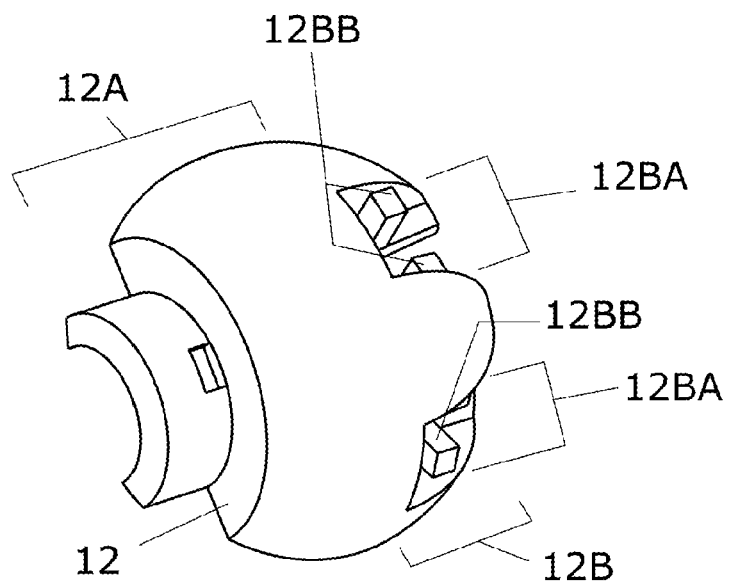
FIG. 25B illustrates a perspective view of a part of the housing 12 according to an embodiment of the device 10.
Figure 26A:
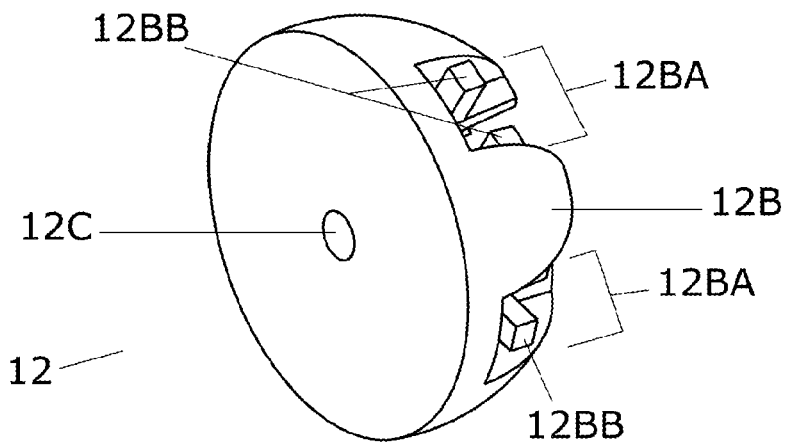
FIG. 26A illustrates a perspective view of a part of the housing 12 according to an embodiment of the device 10.
Figure 26B:
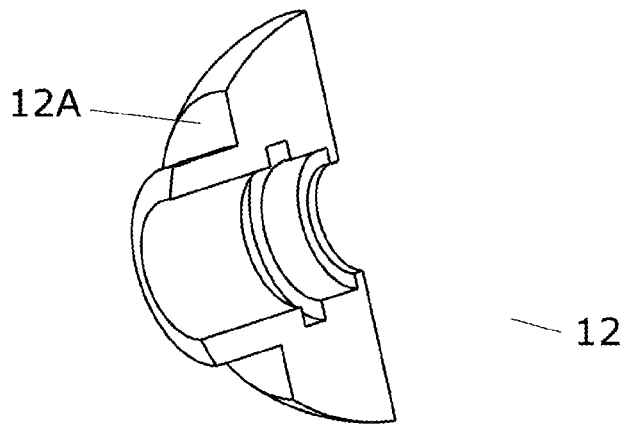
FIG. 26B illustrates a perspective view of a part of the housing 12 according to an embodiment of the device 10.
Figure 26C:
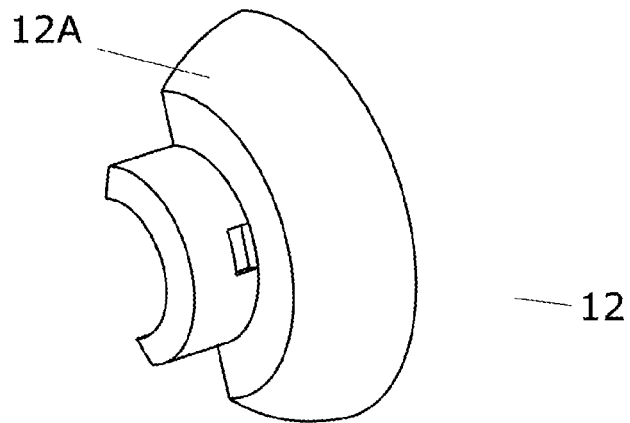
FIG. 26C illustrates a perspective view of a part of the housing 12 according to an embodiment of the device 10.
Figures 43A, 43B:
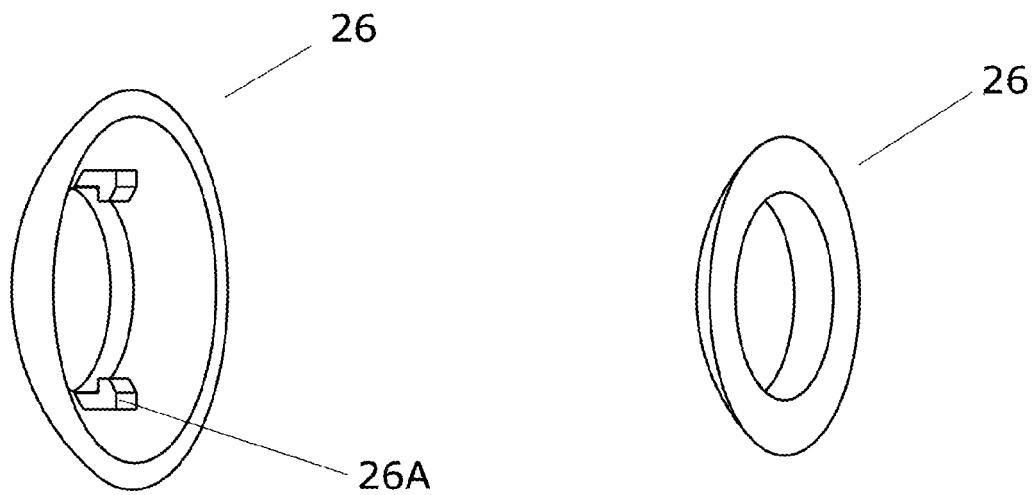
FIG. 43A illustrates a perspective view of the closure element 26 according to an embodiment.
FIG. 43B illustrates a perspective view of a closure element 26 according to an embodiment.
Figure 43C:
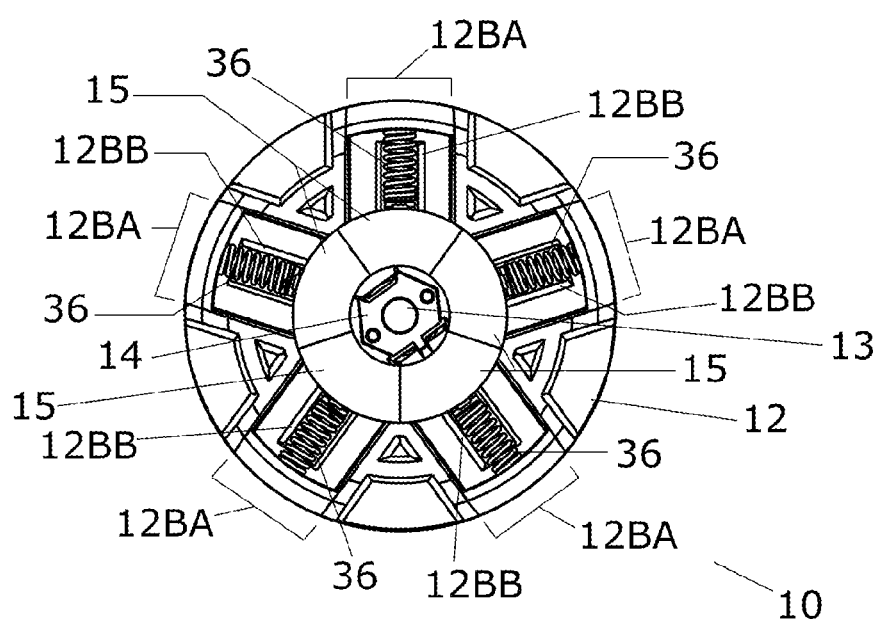
FIG. 43C illustrated a top view of the device 10 with the shaft 17 at its minimum girth according to an embodiment of the device 10 (sheath 16 not illustrated in FIG. 43C).

In a preferred embodiment, the device 10 comprises a housing 12 having a controller first end 12A, a shaft member second end 12B having a plurality of shaft member grooves 12BA and a plurality of shaft member protrusions 12BB, and a non-threaded canal 12C, as illustrated in FIG. 24, FIG. 25 and FIG. 26. Preferably, the non-threaded canal 12C is a non-threaded canal. Preferably, the non-threaded canal 12C receives the first end 13A of the threaded shaft 13, and the controller first end 12A receives the second end 11B of the controller 11 connected to the first end 13A, such that when the housing 12 encloses the second end 11B and the first end 13A, the second end 11B and the first end 13A can only rotate clockwise or counter-clockwise around the longitudinal axis of the threaded shaft 13. Preferably, the shaft member second end 12B via the plurality of shaft member grooves 12BA and the plurality of shaft member protrusions 12BB of the housing 12 is configured to slidably receive the plurality of first end 15A having at least one housing groove 15AA of the plurality shaft members 15 (shaft member 15 illustrated in FIG. 31) such that when the user performs the adjustment of the device 10, each shaft member 15 of the plurality of shaft members 15 can only travel perpendicularly to the longitudinal axis of the threaded shaft 13. Each shaft member groove 12BA receives its corresponding shaft member 15, and each shaft member protrusion 12BB receives its corresponding housing groove 15AA to prevent undesired translation and/or rotation of the corresponding shaft member 15 during the utilization of the device 10. Preferably, the longitudinal axis of each of the plurality of shaft member protrusions 12BB is approximately or precisely perpendicular to the longitudinal axis of the threaded shaft 13, however, to reduce friction and handling stress on the plurality of shaft members 15 during the utilization of the device 10, the longitudinal axis of each of the plurality of shaft member protrusions 12BB may be configured to make an angle greater or lower than 90° with the longitudinal axis of the threaded shaft 13, as illustrated in FIG. 29D. In that case the housing groove 15AA of the shaft member 15 is configured to receive the shaft member protrusion 12BB configured with a longitudinal axis making an angle greater or lower than 90° with the longitudinal axis of the threaded shaft 13. To reduce friction and handling stress on the plurality of shaft members 15 during the utilization of the device 10, the housing 12 may be configured with a plurality of friction reducers 34. The friction reducer 34 is such as, but not limited to: a wheel and its axle held by a socket (as illustrated in FIG. 29C and FIG. 29D) and/or a ball held by a socket (not illustrated). The friction reducer 34 is made of such as, but not limited to: plastic, plastic based and/or metal material. To reduce friction and handling stress on the controller 11 and the plurality of shaft members 15 during the utilization of the device 10, the housing 12 may be lubricated. The shaft member protrusion 12BB of the housing 12 may be configured as a cantilever snap-fit (illustrated in FIG. 27C and FIG. 27D). In that case, the first end 15A of the shaft member 15 is configured to receive the shaft member protrusion 12BB of the housing 12 configured as a cantilever snap-fit (illustrated in FIG. 32C). At least one shaft member groove 12BA may be configured to slidably receive (not illustrated) the closest apex (or the closest flat base) of the conical section with a slant height 14A of the closest module 14 of the housing 12, so as to prevent undesired rotations of the module 14 around the threaded shaft 13. The shaft member protrusion 12BB may be a fastener such as but not limited to: a screw, a nail, or a pin, secured to the housing 12. Preferably, the housing 12 is configured in a geometric shape approximately or precisely, such as, but not limited to: a spherical shape, a wedge shape, a cuboid shape, a rectangular shape, a potatoid shape, a conical shape, a cylinder shape, a pyramid shape, a prism shape, a tetrahedron shape, an icosahedron shape, an octahedron shape, a torus shape, a pentagonal shape, an ellipsoid shape, or a dodecahedron shape. Preferably, the housing 12 is configured to prevent over insertion of the device 10 inside the body orifice. Preferably, the housing 12 is made with a rigid material such as, but not limited to: plastic, plastic-based, hard silicone, iron-based metal, metal, magnet 31, glass and/or wood material. However, the housing 12 may be made in combination with a soft material such as, but not limited to: silicone, silicone-based, and/or rubber material. Preferably, the housing 12 is made with at least one coloration additive, however, the housing 12 may be made with no coloration additive. The housing 12 may be configured with a color code and/or a serial number to distinguish a device 10 with one configuration, one girth adjustment performance and/or one size from another device 10 having another configuration, girth adjustment performance and/or size, to facilitate the utilization for the user of several devices 10. The housing 12 may be configured with at least one visual and/or tactile indication to indicate to the user how to use the device 10. FIG. 24A illustrates a front view of the housing 12 in one embodiment. FIG. 24B illustrates a perspective view of the housing 12 in one embodiment. FIG. 24C illustrates a top view of the housing 12 in one embodiment. FIG. 24D illustrates a bottom view of the housing 12 in one embodiment. For manufacturing and/or assembly optimization purposes of the device 10, the housing 12 may be made in one, two (as illustrated in FIG. 25), three (as illustrated in FIG. 26) parts or more. When the housing 12 is made in several parts, the parts are connected to each other by such as but not limited to: interlocking, rubber banding 35 (as illustrated in FIG. 38), silicone banding, wrapping, gluing, and/or screwing. In another embodiment, at least one shaft member groove 12BA may comprise at least one spring. The spring connects the first end 15A of the shaft member 15 that fits inside the shaft member groove 12BA having at least one spring. Preferably, the spring is such as, but not limited to: a compression spring 36 (as illustrated in FIG. 43C) to facilitate the travel of the first end 15A of the shaft member 15 that fits inside the shaft member groove 12BA having at least one spring, perpendicularly to the longitudinal axis of the threaded shaft 13, in the direction of the longitudinal axis of the threaded shaft 13, when the girth of the shaft 17 is decreased by the user, or the spring is such as, but not limited to: a tension spring (not illustrated) to facilitate the travel of the first end 15A of the shaft member 15 that fits inside the shaft member groove 12BA having at least one spring, perpendicularly to the longitudinal axis of the threaded shaft 13, in the opposite direction of the longitudinal axis of the threaded shaft 13, when the girth of the shaft 17 is increased by the user. Preferably, the spring is made of such as, but not limited to: iron-based metal, metal, plastic, and/or plastic-based material. FIG. 43C illustrates a top view of the device 10 with the shaft 17 at its minimum girth according to an embodiment of the device 10 (sheath 16 not illustrated in FIG. 43C).

In another embodiment as illustrated in FIG. 25A, the housing 12 may comprise at least one module anti-rotation protrusion 12F. The module anti-rotation protrusion 12F is configured to fit inside the housing anti-rotation cavity 14D of the module 14 having at least one housing anti-rotation cavity 14D (illustrated in FIG. 30F), such that when the threaded shaft 13 is rotated clockwise, the module 14, prevented from rotating by the interaction between the module anti-rotation protrusion 12F and the anti-rotation protrusion cavity 14D, travels along the threaded shaft 13 in the direction of the housing 12, and when the threaded shaft 13 is rotated counter-clockwise, the module 14, prevented from rotating by the interaction between the module anti-rotation protrusion 12F and the anti-rotation protrusion cavity 14D, travels along the threaded shaft 13 in the opposite direction of the housing 12. Preferably, the module anti-rotation protrusion 12F is made with the housing 12, however, the module anti-rotation protrusion 12F may be made separately and then secured to the housing 12. In that case, the module anti-rotation protrusion 12F is preferably made of such as, but not limited to: plastic, plastic-based and/or metal material.

Figure 27A:
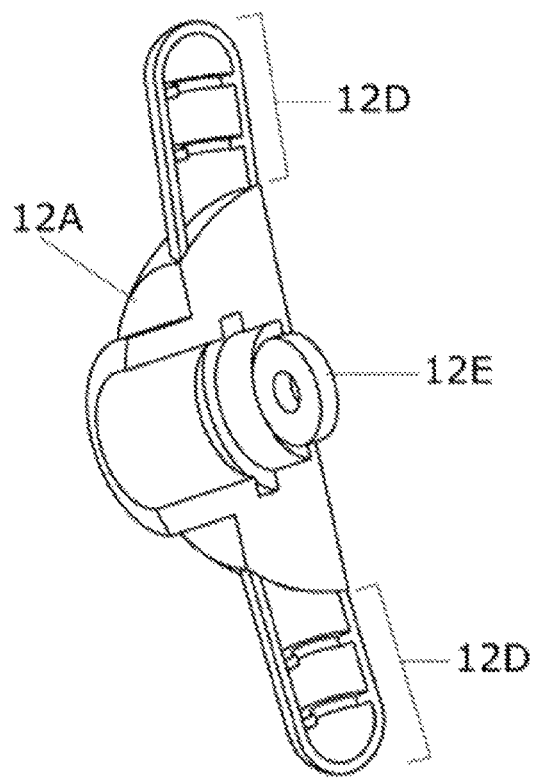
FIG. 27A illustrates a perspective view of a part of the housing 12 according to an embodiment of the device 10.
Figure 27B:
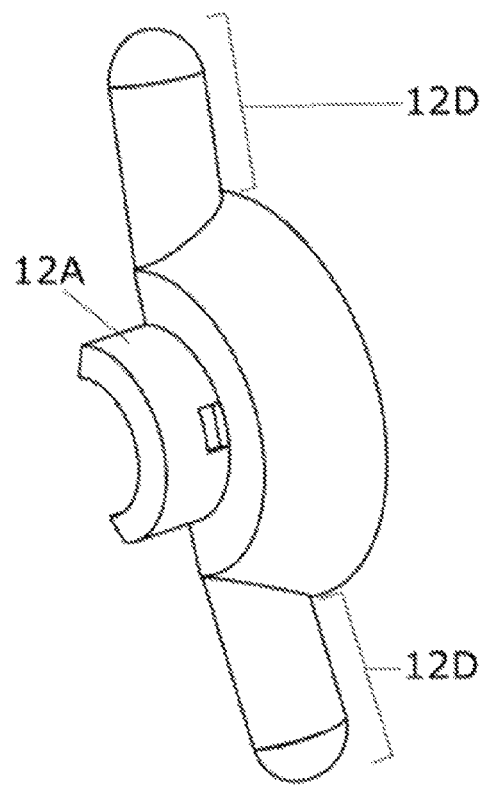
FIG. 27B illustrates a perspective view of a part of the housing 12 according to an embodiment of the device 10.
Figure 27C:
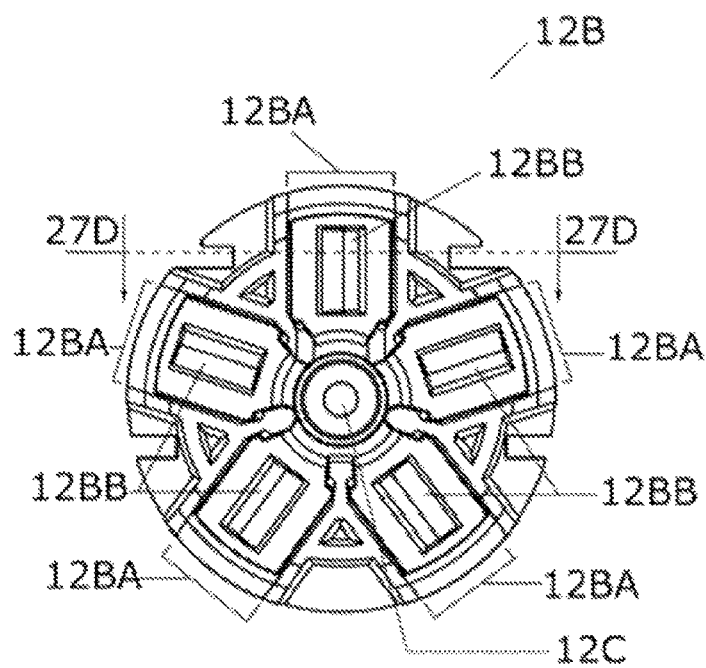
FIG. 27C illustrates a top view of a part of the housing 12 according to an embodiment of the device 10.
Figure 27D:
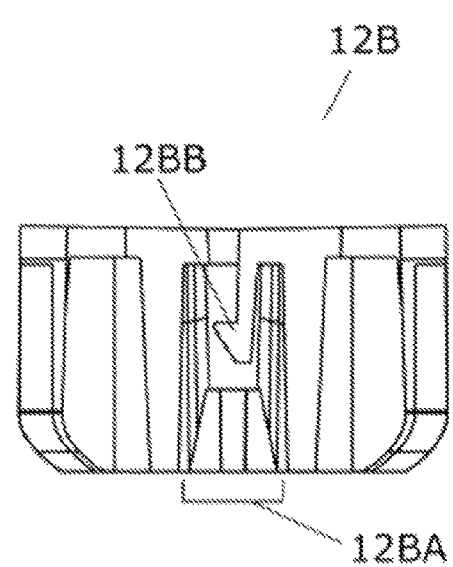
FIG. 27D illustrates a section view of FIG. 27C.

In another embodiment, as illustrated in FIG. 27A, the housing 12 may comprise at least one bearing 12E. Preferably, the bearing 12E is such as, but not limited to: a plain bearing, a washer fastener, and/or a rolling-element bearing, made of such as, but not limited to: metal, plastic and/or plastic based material. Preferably, the bearing 12E is configured to receive the first end 13A of the threaded shaft 13 and/or the second end 11B of the controller 11. The bearing 12E reduces friction and handling stress on the device 10 during the utilization of the device 10. FIG. 27A illustrates a perspective view of a part of the housing 12 in this embodiment.

Figure 28A:
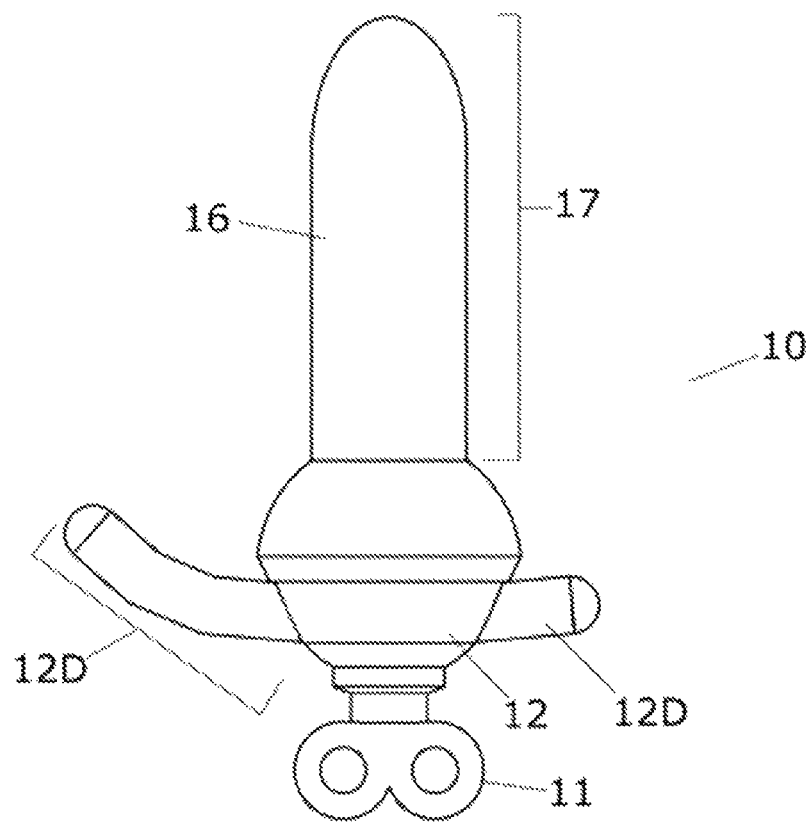
FIG. 28A illustrates a front view of the device 10 with the shaft 17 at its minimum girth according to an embodiment of the device 10.
Figure 28B:
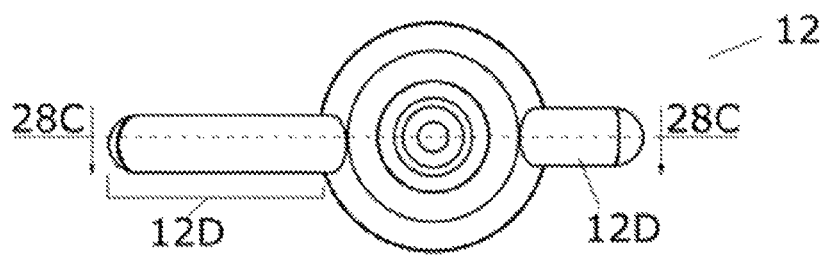
FIG. 28B illustrates a bottom view of the housing 12 according to an embodiment of the device 10.
Figure 28C:
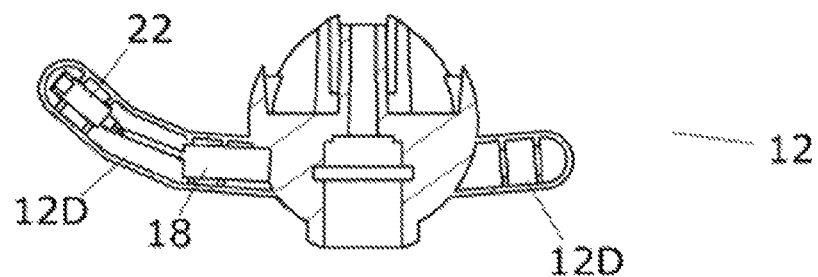
FIG. 28C illustrates a section view of FIG. 28B.

In another embodiment, as illustrated in FIG. 27 and FIG. 28, the housing 12 may comprise at least one housing multi-purpose protrusion 12D. The housing multi-purpose protrusion 12D prevents the device 10 to rotate inside the body orifice when the user performs the adjustment of the device 10, by pressing against the nearest body part of the body orifice where the shaft 17 of the device 10 is inserted. The housing multi-purpose protrusion 12D is also a handle to facilitate the utilization of the device 10. The housing multi-purpose protrusion 12D may comprise: an electronic part 18 (illustrated in FIG. 28C), a vibration motor 22 connected to an electronic part 18 (illustrated in FIG. 28C; vibration motor 22 described in Vibrator unit section), a heating element connected to an electronic part 18 (not illustrated in this embodiment; heating element described in Heating element section), a heart rate monitor connected to an electronic part 18 (not illustrated in this embodiment; heart rate monitor described in Heart rate monitor section), an electrical stimulation electrode connected to an electronic part 18 (not illustrated in this embodiment; electric stimulation electrode described in Electric stimulation electrode section), a penis ring (not illustrated in this embodiment; penis ring described in Penis ring section), a weight 32 (not illustrated in this embodiment; weight 32 described in Weight section), and/or a girth adjustment indicator 23 (not illustrated in this embodiment; girth adjustment indicator 23 described in Girth adjustment indicator section). The housing multi-purpose protrusion 12D also prevents over-insertion of the device 10 into the body orifice. The housing multi-purpose protrusion 12D may also be configured to stimulate another body part (such as a vagina when the device 10 is inserted into an anus) during the utilization of the device 10. The housing multi-purpose protrusion 12D may also be configured to be inserted into another body orifice (such as a vagina when the device 10 is inserted into an anus) during the utilization of the device 10. The housing multi-purpose protrusion 12D is preferably made with the housing 12, however, the housing multi-purpose protrusion 12D may be made separately and configured to be removably secured to the housing 12, which means that the housing multi-purpose protrusion 120 may be repeatedly secured to the housing 12, then removed from the housing 12, and then secured again to the housing 12. In that case, the housing multi-purpose protrusion 12D is preferably made of such as, but not limited to: plastic, plastic-based, silicone, silicone-based, rubber, glass, leather, metal and/or wood material. FIG. 27A illustrates a perspective view of a part of the housing 12 in this embodiment. FIG. 27B illustrates a perspective view of a part of the housing 12 in this embodiment. FIG. 28A illustrates a front view of the device 10 with the shaft 17 at its minimum girth in this embodiment. FIG. 28B is a bottom view of the housing 12 according to this embodiment. FIG. 28C illustrates a section view of FIG. 28B. This embodiment provides others features to the user during the utilization of the device 10.

Figure 45:
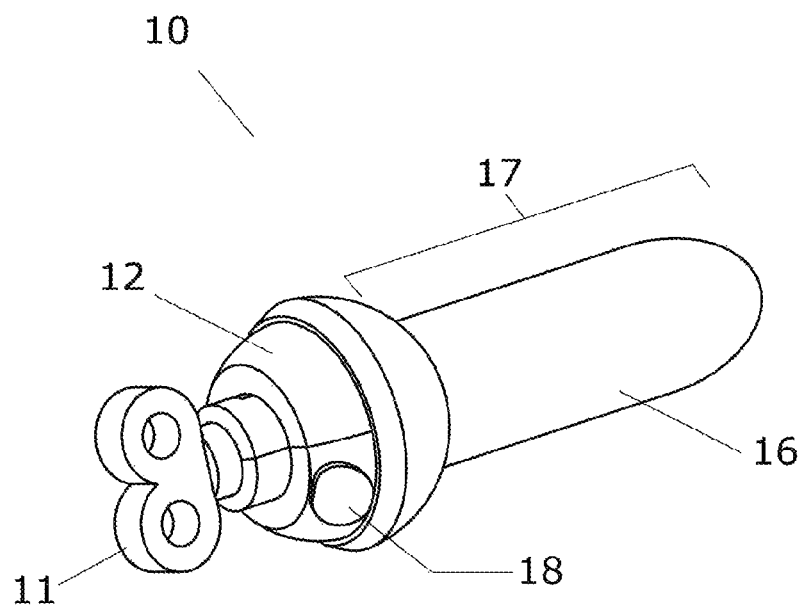
FIG. 45 illustrates a perspective view of the device 10 with the shaft 17 at its minimum girth according to an embodiment of the device 10.

In another embodiment, the housing 12 may comprise at least one: an electronic part 18 (as illustrates in FIG. 45), a vibration motor 22 as illustrated in FIG. 29A, connected to an electronic part 18 (not illustrated in FIG. 29A), a girth adjustment indicator 23 as illustrated in FIG. 29B, a heating element connected to an electronic part 18 (not illustrated), a heart rate monitor unit connected to an electronic part 18 (not illustrated), an electrical stimulation electrode connected to an electronic part 18 (not illustrated), a penis ring (not illustrated), and/or a weight 32 (illustrated in FIG. 29B). FIG. 29A illustrates a perspective view of a part of the housing 12 according to an embodiment of the device 10. FIG. 29B illustrates a perspective view of a part of the housing 12 according to an embodiment of the device 10. FIG. 45 illustrates a perspective view of the device 10 with the shaft 17 at its minimum girth according to an embodiment of the device 10. This embodiment provides others features to the user during the utilization of the device 10.

Module

The module 14 has at least one conical section with a slant height 14A, at least one anti-rotation connector, and a canal 140, as illustrated in FIG. 30. In a preferred embodiment as illustrated in FIG. 2, FIG. 3 and FIG. 4, the device 10 comprises at least two modules 14 having one conical section with a slant height 14A, at least one anti-rotation connector, and a canal 14C (module 14 in this embodiment illustrated in FIG. 30A, FIG. 30B, FIG. 30D, FIG. 30E, FIG. 30G, and FIG. 30H), or at least one module 14 having at least two conical sections with a slant height 14A, at least one anti-rotation connector, and a canal 14C (device 10 not illustrated in this embodiment; module 14 in this embodiment illustrated in FIG. 30C and FIG. 30F) per threaded shaft 13. However, it is feasible to configure the device 10 with one module 14 having one conical section with a slant height 14A, at least one anti-rotation connector, and a canal 140 (device 10 not illustrated in this embodiment) per threaded shaft 13.

Preferably, the conical section with a slant height 14A is configured in an approximately or precisely conical shape, and therefore configured with an apex, a slant height and a flat base. Preferably, the slant height of the conical section with a slant height 14A is greater than 0.1 inches. Preferably, the canal 14O passes through the conical section with a slant height 14A, from the apex to the center of the flat base. The canal 14C is such as: a threaded canal, a threaded canal having at least one fastener cavity, or a non-threaded canal having at least one fastener cavity 14CA (as illustrated in FIG. 30E, FIG. 30F and FIG. 30G). The function of the canal 14C is to interact mechanically with the threaded shaft 13 when the threaded shaft 13 rotates, to make the module 14 (prevented from rotating) travel on the threaded shaft 13. When the canal 14C is threaded, the mechanical interaction between the canal 14O and the threaded shaft 13 is direct, when the canal 14O is non-threaded having at least one fastener cavity, in which the fastener cavity includes at least one fastener such as, but not limited to: a nut fastener, and/or a wing nut fastener, the mechanical interaction between the canal 14C and the threaded shaft 13 is via the fastener inserted inside the fastener cavity, and when the canal 14O is threaded having a at least one fastener cavity, in which the fastener cavity includes at least one fastener such as, but not limited to: a nut fastener, and/or a wing nut fastener, the mechanical interaction between the canal 14C and the threaded shaft 13 is direct and via the fastener inserted inside the fastener cavity. Therefore, the canal 14C is configured to receive the threaded shaft 13, such that when the threaded shaft 13 is rotated clockwise, the module 14, prevented from rotating by the interaction between at least one anti-rotation connector and at least one module connector groove 15D of at least one shaft member 15, travels on the threaded shaft 13 in the direction of the housing 12, and when the threaded shaft 13 is rotated counter-clockwise, the module 14, prevented from rotating by the interaction between at least one anti-rotation connector and at least one module connector groove 15D of at least one shaft member 15, travels on the threaded shaft 13 in the opposite direction of the housing 12. The flat base of the conical section with a slant height 14A of at least one module 14 may be configured to slidably receive (not illustrated) the apex of the conical section with a slant height 14A of the following module 14, so as to prevent undesired rotations of the modules 14 around the threaded shaft 13. Preferably, the apex of the conical section with a slant height 14A is in the direction of the housing 12, however, the apex of the conical section with a slant height 14A may be in the opposite direction of the housing 12, reversing the direction of the rotation of the threaded shaft 13 for the user to perform the adjustment of the device 10. To reduce friction and handling stress on the plurality of shaft member 15 during the utilization of the device 10, the module 14 may be configured with at least one friction reducer 34. The friction reducer 34 is such as, but not limited to: a wheel and its axle held by a socket (as illustrated in FIG. 30F) and/or a ball held by a socket (not illustrated). To reduce friction and handling stress on the on the plurality of shaft member 15 during the utilization of the device 10, the module 14 may be lubricated. Preferably, the module 14 is made with a rigid material such as, but not limited to: plastic, plastic-based, hard silicone magnet 31, iron-based metal and/or metal material. Preferably, the conical section with a slant height 14A is configured in an approximately or precisely, conical shape, however, the conical section with a slant height 14A may be configured in a geometric shape approximately or precisely, such as but not limited to: a spherical shape, a triangle shape, a pyramid shape, a cuboid shape, a prism shape, a potatoid, a icosahedron shape, a octahedron shape, a pentagonal shape, an ellipsoid shape, a dodecahedron shape and/or a rectangular shape.

Figure 30A:
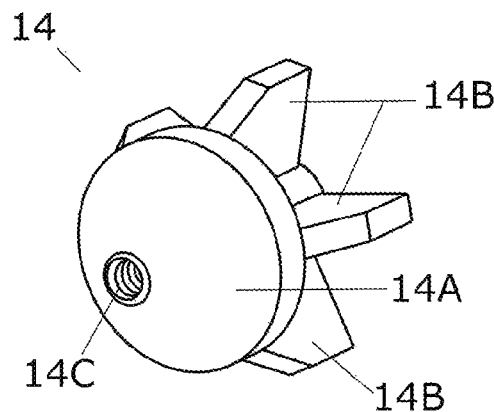
FIG. 30A illustrates a perspective view of a module 14 according to an embodiment.
Figure 30B:
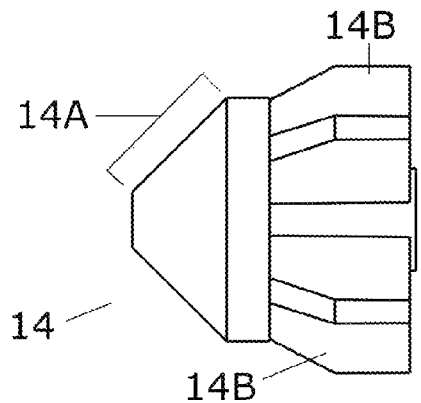
FIG. 30B illustrates a side view of a module 14 according to an embodiment.
Figure 30C:
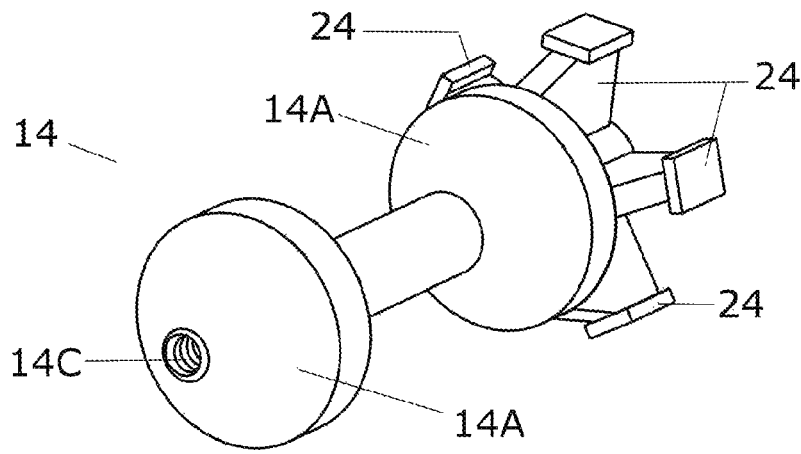
FIG. 30C illustrates a perspective view of a module 14 according to an embodiment.
Figure 30D:
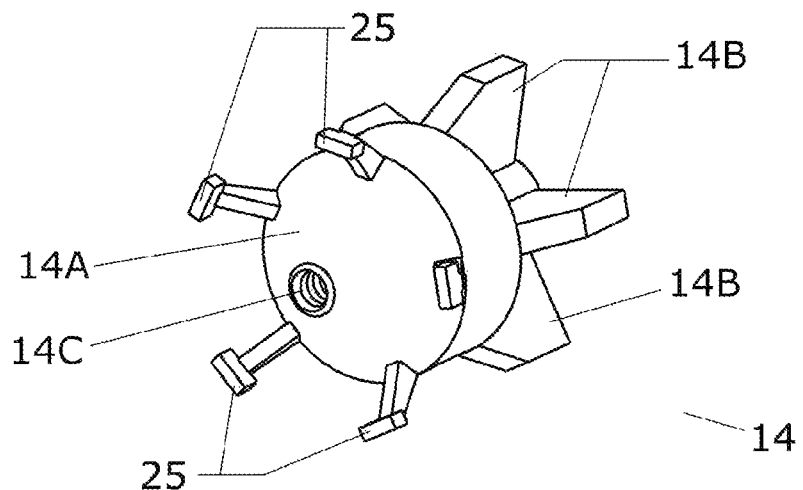
FIG. 30D illustrates a perspective view of a module 14 according to an embodiment.
Figure 30E:
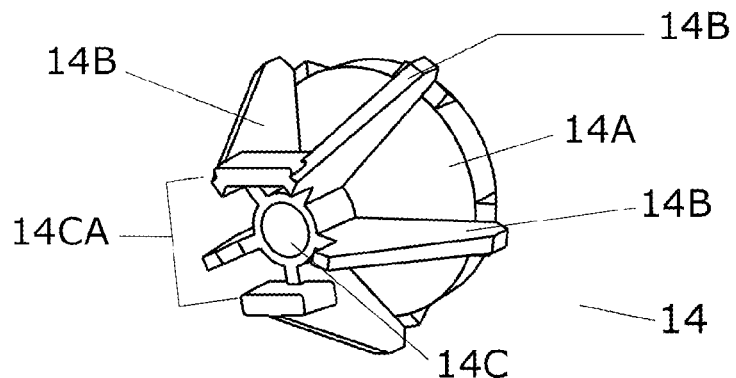
FIG. 30E illustrates a perspective view of a module 14 according to an embodiment.
Figure 30F:
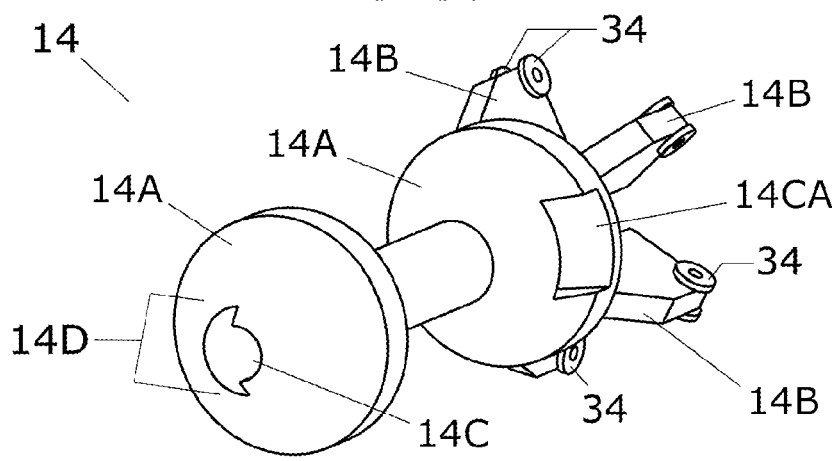
FIG. 30F illustrates a perspective view of a module 14 according to an embodiment.
Figure 30G:
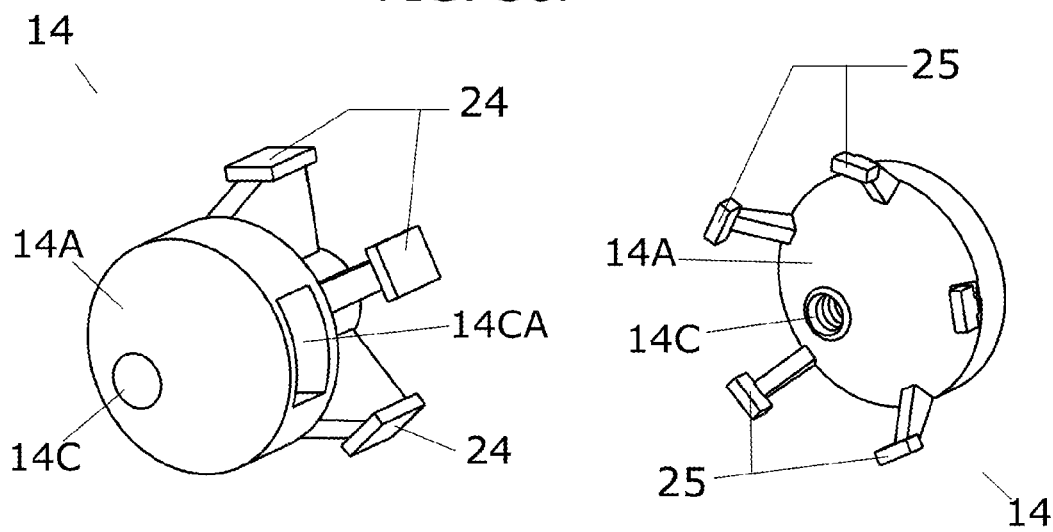
FIG. 30G illustrates a perspective view of a module 14 according to an embodiment.
Figure 30H:
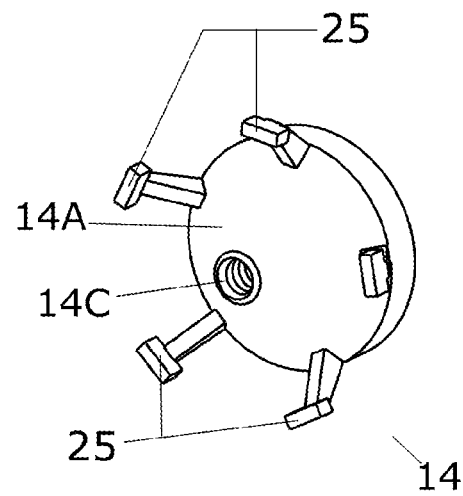
FIG. 30H illustrates a perspective view of a module 14 according to an embodiment.

As illustrated in from FIG. 30A to FIG. 30G, the anti-rotation connector of the module 14 is such as: a linear anti-rotation connector 14B (illustrated in FIG. 30A, FIG. 30B, FIG. 30D, FIG. 30E, and FIG. 30F), a capital letter T shape anti-rotation connector 24 (illustrated in FIG. 30C, and FIG. 30G), and an inclined capital letter T shape anti-rotation connector 25 (illustrated in FIG. 30D, and FIG. 30H). The function of the anti-rotation connector of the module 14 (when slidably connected to the module connector groove 15D of the shaft member 15), is to prevent the module 14 from rotating, and therefore the module 14 travels along the threaded shat 13, when the threaded shaft 13 rotates.

As illustrated in FIG. 30A, FIG. 30B, FIG. 30D, FIG. 30E, and FIG. 30F, the linear anti-rotation connector 14B is positioned approximately or precisely perpendicularly to the longitudinal axis of threaded shaft 13.

As illustrated in FIG. 30C, and FIG. 30G, the capital letter T shape anti-rotation connector 24 is configured in an approximately or precisely similar shape of the capital letter T positioned approximately or precisely perpendicularly to the longitudinal axis of threaded shaft 13. The shaft member 15 is configured to slidably receive via the module connector groove 15D (illustrated in FIG. 31) the capital letter T shape anti-rotation connector 24. FIG. 30C illustrates a perspective view of the module 14 in this embodiment. FIG. 30G illustrates a perspective view of the module 14 in this embodiment.

As illustrated in FIG. 30D, and FIG. 30H, the inclined capital letter T shape anti-rotation connector 25 is configured in an approximately or precisely similar shape of an inclined capital letter T. The inclined capital letter T shape anti-rotation connector 25 makes an angle greater than 0.1° with the longitudinal axis of the threaded shaft 13. The shaft member 15 is configured to slidably receive via the module connector groove 15D (illustrated in FIG. 31) the inclined capital letter T shape anti-rotation connector 25. FIG. 30D illustrates a perspective view of the module 14 in this embodiment. FIG. 30H illustrates a perspective view of the module 14 in this embodiment.

FIG. 30A illustrates a perspective view of the module 14 having one conical section with a slant height 14A, a plurality of linear anti-rotation connectors 14B, and a canal 14C in one embodiment. FIG. 30B illustrates a side view of the module 14 having one conical section with a slant height 14A, a plurality of linear anti-rotation connectors 14B, and a canal 14C in one embodiment. FIG. 30C illustrates a perspective view of the module 14 having two conical sections with a slant height 14A, a plurality of capital letter T shape anti-rotation connectors 24, and a canal 14C in one embodiment. FIG. 30D illustrates a perspective view of the module 14 having one conical section with a slant height 14A, a plurality of linear anti-rotation connectors 14B and a plurality of inclined capital letter T shape anti-rotation connectors 25, and a canal 14C in one embodiment. FIG. 30E illustrates a perspective view of the module 14 having one conical section with a slant height 14A, a plurality of linear anti-rotation connectors 14B, and a canal 14C in one embodiment. FIG. 30F illustrates a perspective view of the module 14 having two conical sections with a slant height 14A, a plurality of linear anti-rotation connectors 14B, and a canal 14C in one embodiment. FIG. 30G illustrates a perspective view of the module 14 having one conical section with a slant height 14A, a plurality of capital letter T shape anti-rotation connectors 24, and a canal 14C in one embodiment. FIG. 30H illustrates a perspective view of the module 14 having one conical section with a slant height 14A, a plurality of inclined capital letter T shape anti-rotation connectors 25, and a canal 14C in one embodiment.

In another embodiment, the module 14 (as illustrated in FIG. 30F) may comprise at least one anti-rotation protrusion cavity 14D. The housing anti-rotation cavity 14D is configured to receive the module anti-rotation protrusion 12F of the housing 12 having at least one module anti-rotation protrusion 12F, such that when the threaded shaft 13 is rotated clockwise, the module 14, prevented from rotating by the interaction between the housing anti-rotation cavity 14D and the module anti-rotation protrusion 12F, travels into the direction of the housing 12 and when the threaded shaft 13 is rotated counter-clockwise, the module 14, prevented from rotating by the interaction between the module anti-rotation protrusion 12F and the anti-rotation protrusion cavity 14D, travels in the opposite direction of the housing 12. This embodiment is, such that when the user performs the adjustment of the device 10, the interaction between the module anti-rotation protrusion 12F and the housing anti-rotation cavity 140 prevents the module 14 of undesired rotation and reinforces the global structure of the device 10.

Shaft Member

Figure 31A:
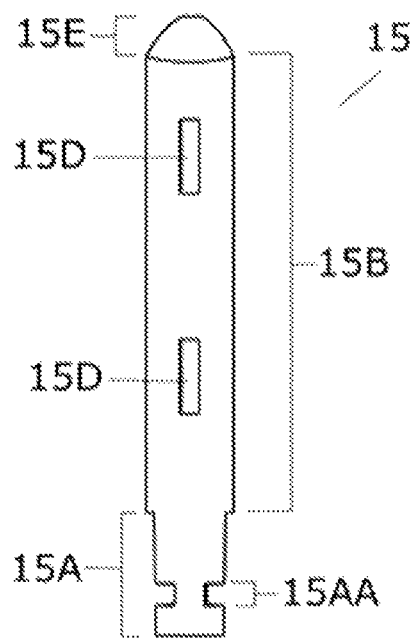
FIG. 31A illustrates a front view of a shaft member 15 according to an embodiment.
Figure 31B:
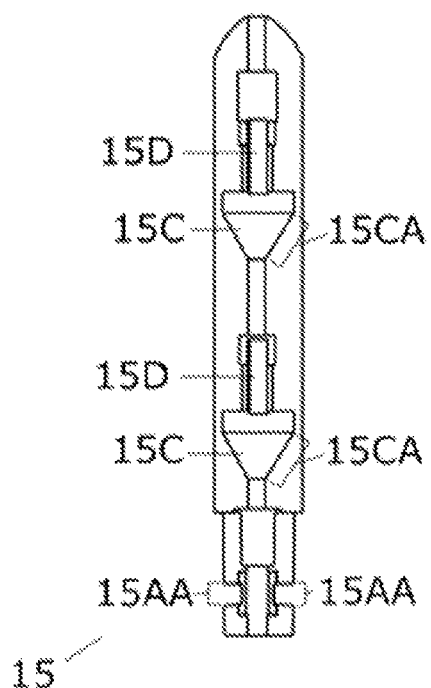
FIG. 31B illustrates a back view of a shaft member 15 according to an embodiment.
Figure 31C:
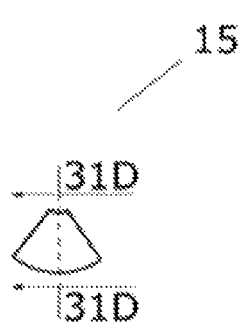
FIG. 31C illustrates a top view of a shaft member 15 according to an embodiment.
Figure 31D:
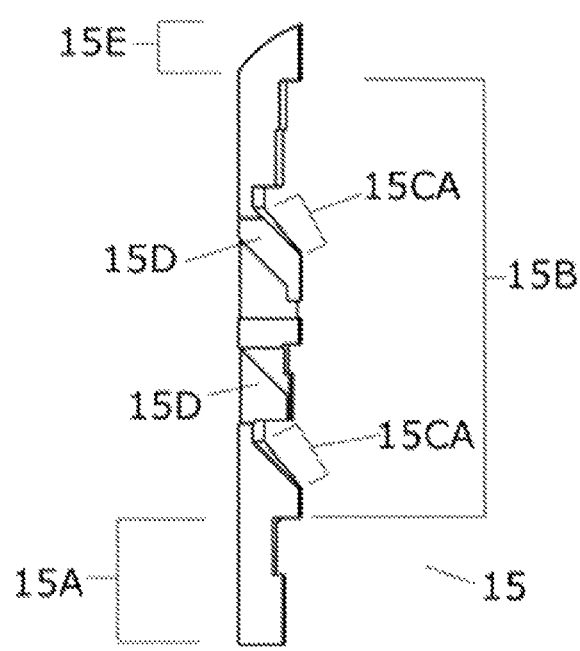
FIG. 31D illustrates a section view of FIG. 31C.
Figure 32A:
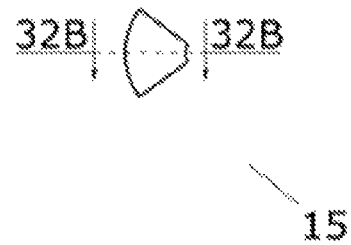
FIG. 32A illustrates a top view of a shaft member 15 according to an embodiment.

In a preferred embodiment the device 10 comprises a plurality of shaft members 15. A shaft member 15 has a first end 15A having at least one housing groove 15AA, a middle section 15B, at least one module cavity 15C with a sloped edge 15CA, at least one module connector groove 15D, and a tip end 15E (shaft member 15 illustrated in FIG. 31). The tip end 15E may be configured with a profiled shape as illustrated in FIG. 32C and FIG. 32D, to facilitate the insertion of shaft 17 into the body orifice.

Attention being called to the fact that the device 10 preferably comprises more than four shaft members 15 per threaded shaft 13 (five or six shaft members in a preferred embodiment) with the aim to generate during the adjustment, a substantially uniform pressure, from the center toward the lateral surface area of the body orifice, over the entire lateral surface area and over the entire length of the body orifice at the same time, or with the aim to reduce a substantially uniform pressure, from the entire lateral surface area of the body orifice and from the entire length of the body orifice at the same time. This specific repartition of the pressure has the aim to provide an optimum performance and comfort for the user for the dilation and stretch of body orifices, however, it is feasible to configure the device with only two (as illustrated in FIG. 33, sheath 16 not illustrated), three or four shaft members (device 10 not illustrated in this embodiment). Preferably, the shaft member 15 has as many module cavities 15C as the device 10 comprises conical sections with a slant height 14A of the module 14. Preferably, the conical section with a slant height 14A of the module 14 is configured on the middle section 13B and/or the second end 13C of the threaded shaft 13 to slidably fit inside the module cavity 15C. During the adjustment of the device 10, the sloped edge 15CA of the module cavity 15C slides against the slant height of the conical section with a slant height 14A of the module 14, defining partially the specific characteristics of the adjustment of the device 10. However, the sloped edge 15CA of the module cavity 15C can slide against any another edge of the module 14, in the case that the conical section with a slant height 14A of the module 14 is configured in a different geometric shape than an approximately or precisely conical shape.

Figure 32C:
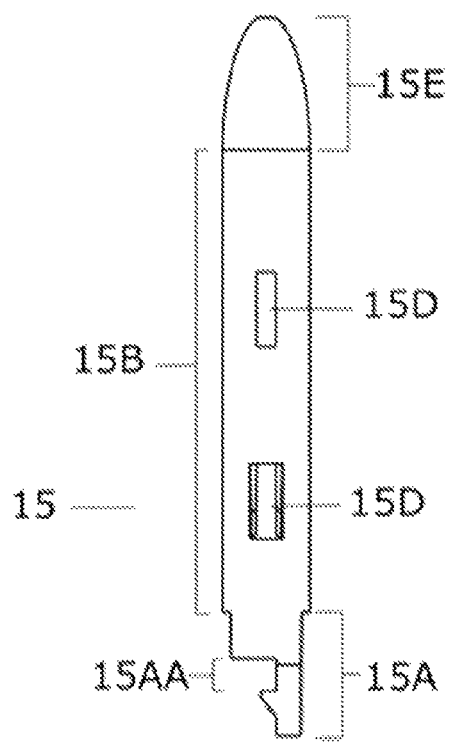
FIG. 32C illustrates a front view of a shaft member 15 according to an embodiment.
Figure 32D:
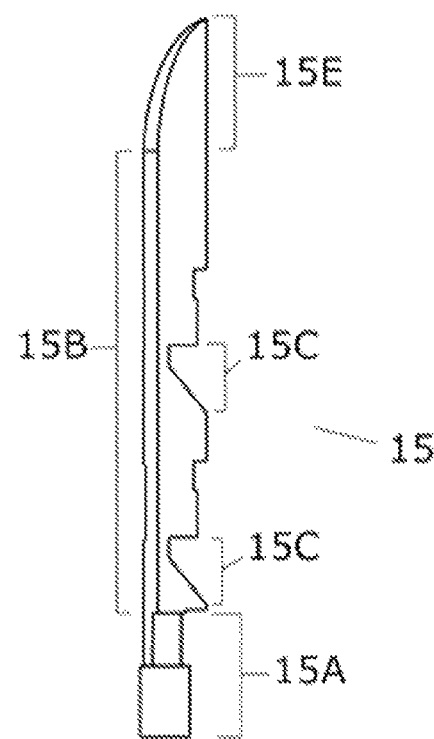
FIG. 32D illustrates a side view of a shaft member 15 according to an embodiment.
Figure 33A:
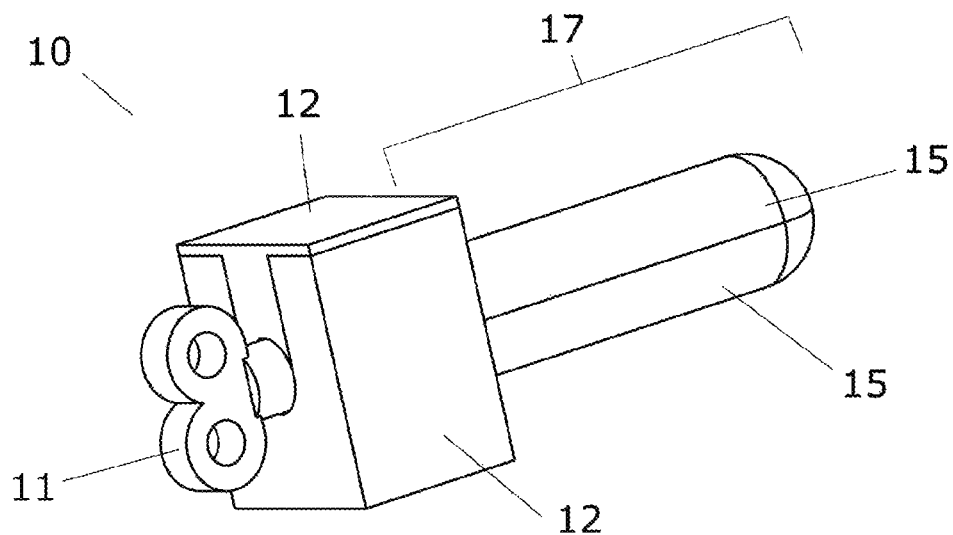
FIG. 33A illustrates a perspective view of the device 10 with the shaft 17 at its minimum girth according to an embodiment of the device 10 (sheath 16 not illustrated in FIG. 33A).
Figure 33B:
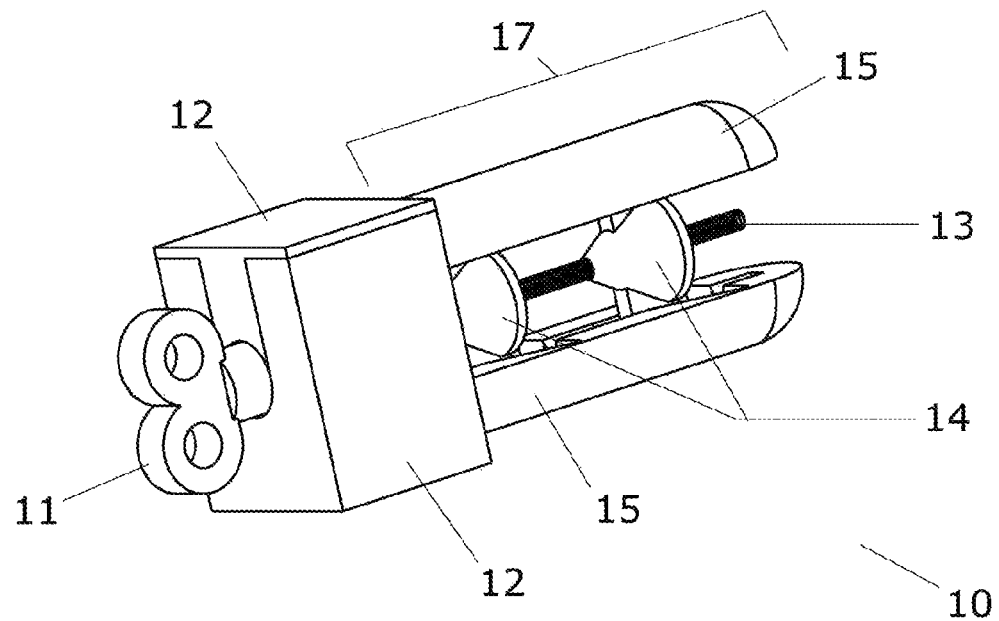
FIG. 33B illustrates a perspective view of the device 10 with the shaft 17 at its maximum girth according to an embodiment of the device 10 (sheath 16 not illustrated in FIG. 33B).
Figure 34A:
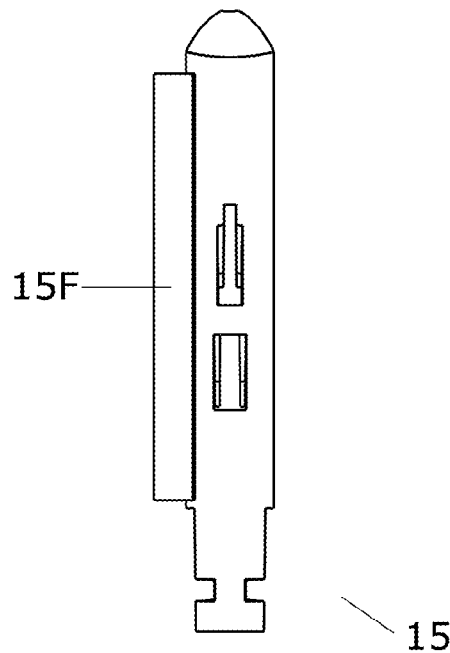
FIG. 34A illustrates a front view of a shaft member 15 according to an embodiment, and when the shaft 17 of the device 10 is at its minimum girth.
Figure 34B:
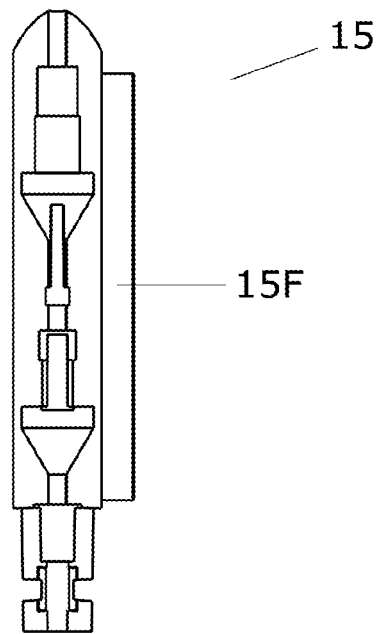
FIG. 34B illustrates a back view of a shaft member 15 according to an embodiment, and when the shaft 17 of the device 10 is at its minimum girth.
Figure 34C:
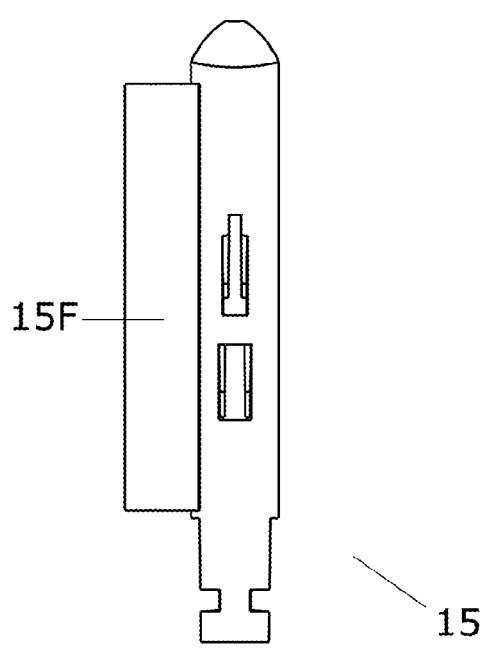
FIG. 34C illustrates a front view of a shaft member 15 according to an embodiment, and when the shaft 17 of the device 10 is at its maximum girth.
Figure 34D:
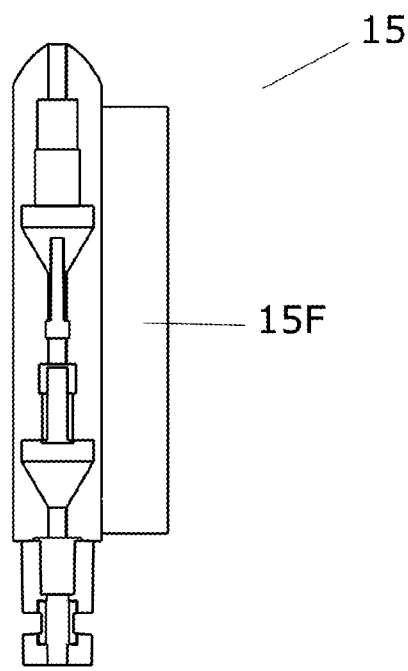
FIG. 34D illustrates a back view of a shaft member 15 according to an embodiment, and when the shaft 17 of the device 10 is at its maximum girth.

The plurality of shaft members 15 is configured to surround the threaded shaft 13, and the module 14. When the shaft 17 of the device 10 is at its minimum girth, the girth of the plurality of shaft members 15 is greater than 0.4 inches (girth calculated with the outside diameter of the cylindrical shape formed by the plurality of shaft members 15 when the shaft 17 of the device 10 is at its minimum girth, as illustrated in FIG. 2A). Preferably, the length of the shaft member 15, from the first end 15A to the tip end 15E is greater than 1 inch. To reduce friction and handling stress on the housing 12 and/or the module 14 during the utilization of the device 10, each shaft member 15 may be configured with at least one friction reducer 34. The friction reducer 34 is such as, but not limited to: a wheel and its axle held by a socket (as illustrated in FIG. 38B) and/or a ball held by a socket (not illustrated). To reduce friction and handling stress on the housing 12 and the module 14 during the utilization of the device 10, each shaft member 15 may be lubricated. Preferably, the shaft member 15 is made with a rigid material such as, but not limited to: plastic, plastic-based, hard silicone magnet 31, iron-based metal and/or metal material. FIG. 31A illustrates a front view of one shaft member 15 in one embodiment. FIG. 31B illustrates a back view of one shaft member 15 in one embodiment. FIG. 310 illustrates a top view of one shaft member 15 in one embodiment. FIG. 31D illustrates a section view of FIG. 31C. FIG. 32C illustrates a front view of one shaft member 15 in one embodiment. FIG. 32D illustrates a front view of one shaft member 15 in one embodiment. FIG. 33A illustrates a perspective view of the device 10 with the shaft 17 at its minimum girth according to an embodiment of the device 10 (sheath 16 not illustrated in FIG. 33A). FIG. 33B illustrates a perspective view of the device 10 with the shaft 17 at its maximum girth according to an embodiment of the device 10 (sheath 16 not illustrated in FIG. 33B).

Figure 32B:
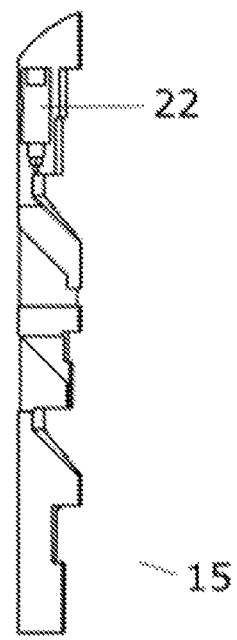
FIG. 32B illustrates a section view of FIG. 32A.

In another embodiment, at least one shaft member 15 may comprise at least one: a vibration motor 22 (as illustrated in FIG. 32B) connected to an electronic part 18 (not illustrated in FIG. 32B), a heating element connected to an electronic part 18 (not illustrated), an electric stimulation electrode connected to an electronic part 18 (not illustrated), and/or a heart rate monitor connected to an electronic part 18 (not illustrated). This embodiment provides others features to the user during the utilization of the device 10. FIG. 32A is a top view of one shaft member in one embodiment. FIG. 32B illustrates a section view of FIG. 32A.

Figures 35A, 35B:
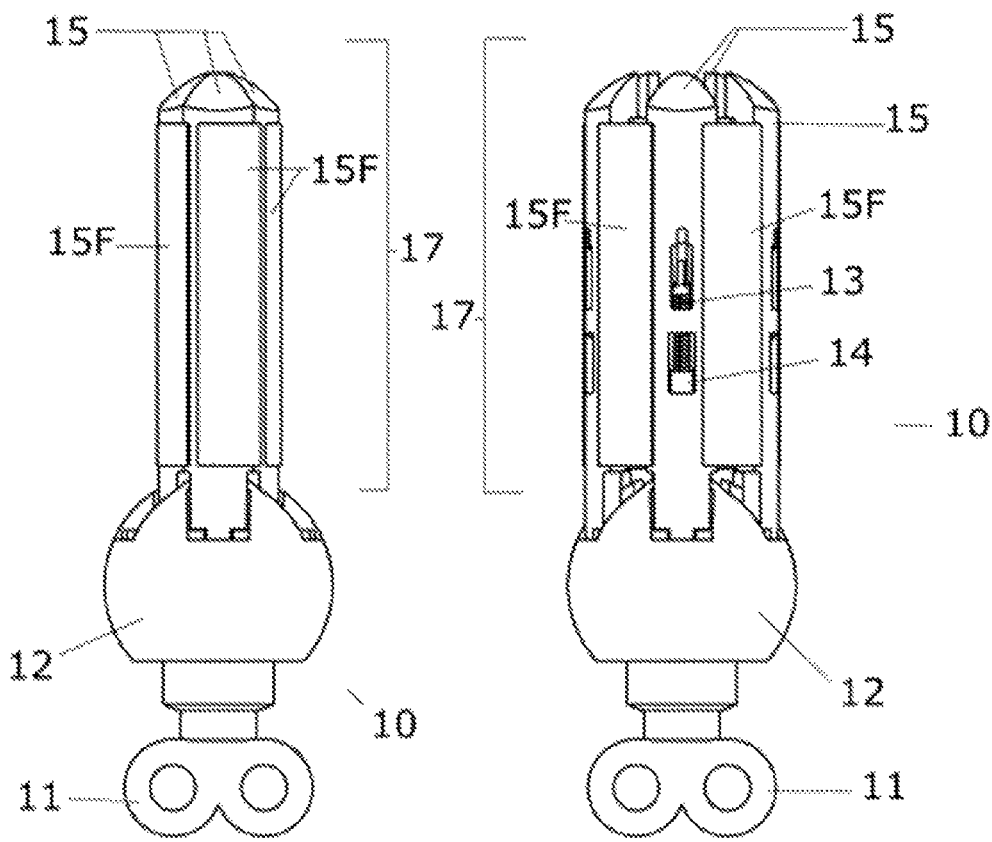
FIG. 35A illustrates a front view of the device 10 with the shaft 17 at its minimum girth according to an embodiment of the device 10 (sheath 16 not illustrated in FIG. 35A).
FIG. 35B illustrates a front view of the device 10 with the shaft 17 at its maximum girth according to an embodiment of the device 10 (sheath 16 not illustrated in FIG. 35B).
Figures 35C, 35D:
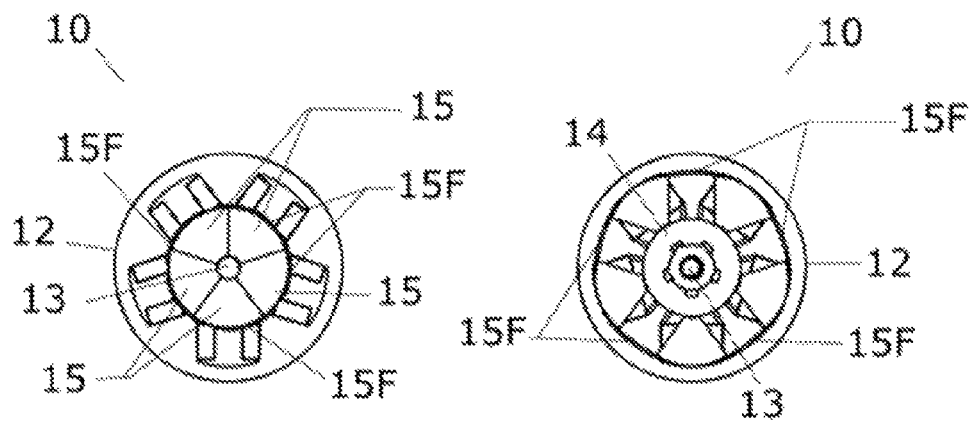
FIG. 35C illustrates a top view of the device 10 with the shaft 17 at its minimum girth according to an embodiment of the device 10 (sheath 16 not illustrated in FIG. 35C).
FIG. 35D illustrates a top view of the device 10 with the shaft 17 at its maximum girth according to an embodiment of the device 10 (sheath not illustrated in FIG. 35D).
Figure 36A:
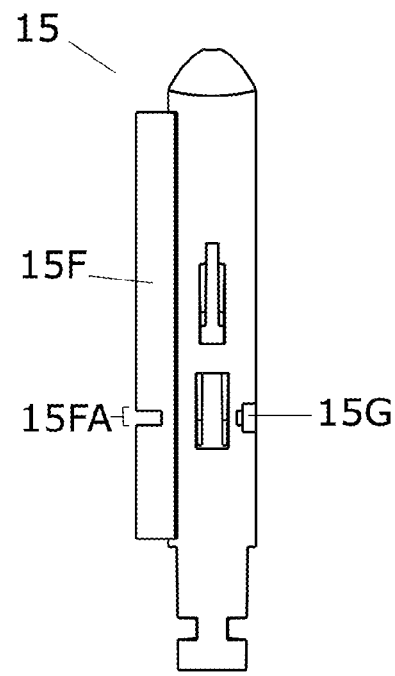
FIG. 36A illustrates a front view of a shaft member 15 according to an embodiment, and when the shaft 17 of the device 10 is at its minimum girth.
Figure 36B:
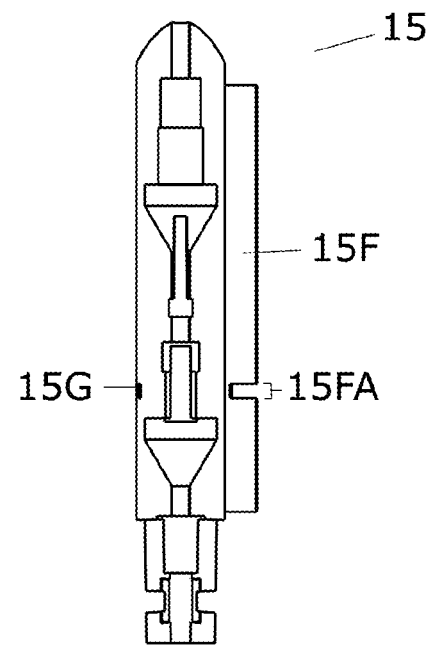
FIG. 36B illustrates a back view of a shaft member 15 according to an embodiment, and when the shaft 17 of the device 10 is at its minimum girth.
Figure 36C:
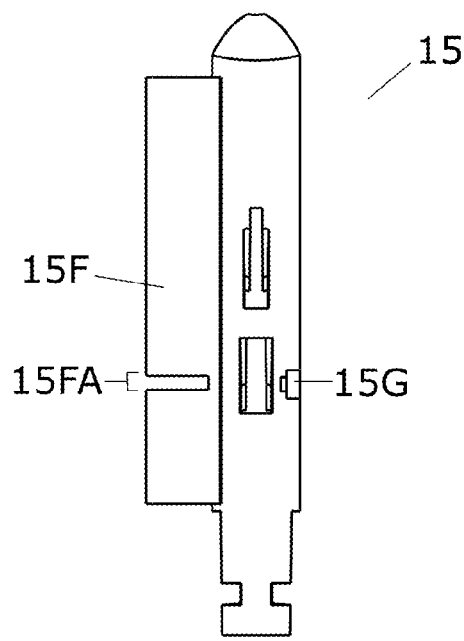
FIG. 36C illustrates a front view of a shaft member 15 according to an embodiment, and when the shaft 17 of the device 10 is at its maximum girth.
Figure 36D:
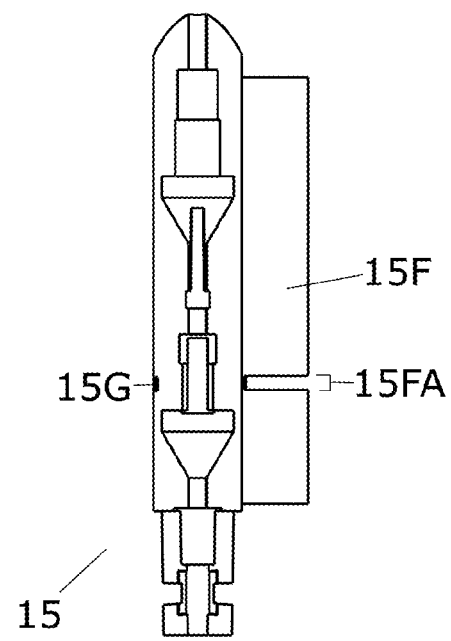
FIG. 36D illustrates a back view of a shaft member 15 according to an embodiment, and when the shaft 17 of the device 10 is at its maximum girth.

In another embodiment, as illustrated in FIG. 34 and FIG. 35, at least one shaft member 15 may comprise at least one side extension 15F. Preferably, the side extension 15F slidably connects the following shaft member 15 (as illustrated in FIG. 35). Attention being called to the fact that this embodiment enhances the repartition of the pressure generated over the entire lateral surface area and over the entire length of the body orifice when the girth of the shaft 17 is increased by the user. The side extension 15F is secured to the shaft member 15 and made with a resilient material, such as but not limited to: plastic and/or plastic-based material. FIG. 34A illustrates a front view of the shaft member 15 having at least one side extension 15F in its original shape, when the shaft 17 of the device 10 is at its minimum girth. FIG. 34B illustrates a back view of the shaft member 15 having at least one side extension 15F in its original shape, when the shaft 17 of the device 10 is at its minimum girth. FIG. 34C illustrates a front view of the shaft member 15 having at least one side extension 15F deformed elastically from its original shape, when the shaft 17 of the device 10 is at its maximum girth. FIG. 340 illustrates a back view of the shaft member 15 having at least one side extension 15F deformed elastically from its original shape, when the shaft 17 of the device 10 is at its maximum girth. FIG. 35A illustrates a front view of the device 10 with the shaft 17 at its minimum girth in this embodiment (sheath 16 not illustrated). FIG. 35B illustrates a front view of the device 10 with the shaft 17 at its maximum girth in this embodiment (sheath 16 not illustrated). FIG. 35C illustrates a top view of the device 10 with the shaft 17 at its minimum girth in this embodiment (sheath 16 not illustrated). FIG. 35D illustrates a top view of the device 10 with the shaft 17 at its maximum girth in this embodiment (sheath 16 not illustrated).

Figure 37A:
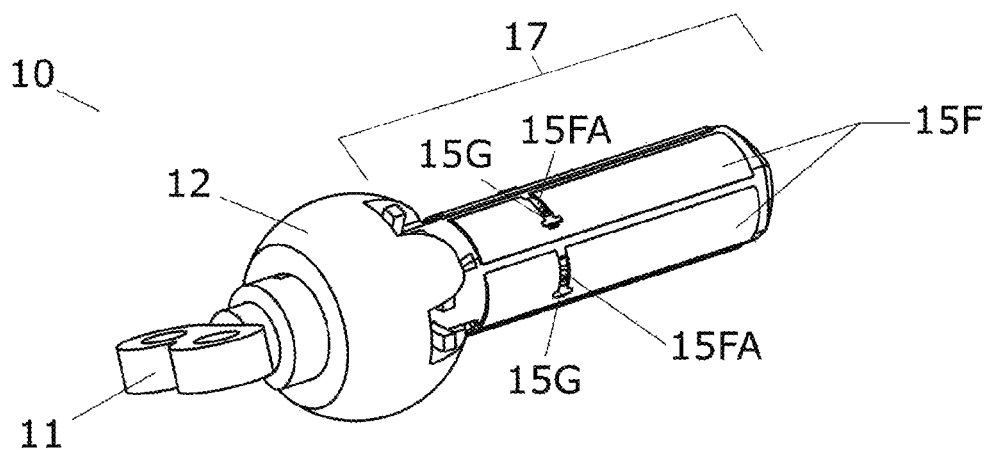
FIG. 37A is a perspective view of the device 10 with the shaft 17 at its minimum girth according to an embodiment of the device 10 (sheath 16 not illustrated in FIG. 37A).
Figure 37B:
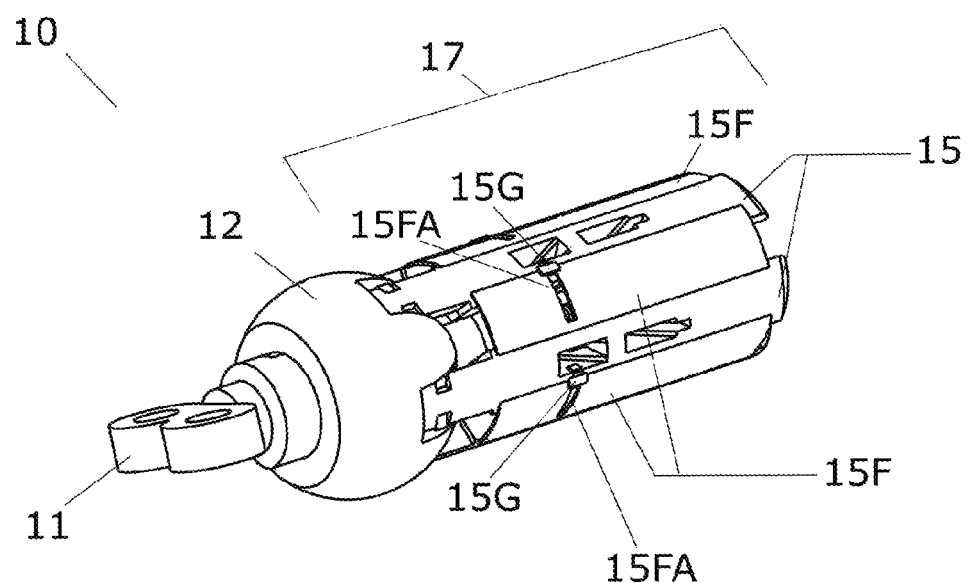
FIG. 37B is a perspective view of device 10 with the shaft 17 is at its maximum girth the according to an embodiment of the device 10 (sheath 16 not illustrated in FIG. 37B).

In another embodiment as illustrated in FIG. 36 and FIG. 37, a plurality of shaft members 15 may comprise at least one side extension 15F having at least one groove 15FA, and at least one side extension groove connector 15G. The side extension groove connector 15G of one shaft member 15 having at least one side extension 15F having at least one groove 15FA, and at least one side extension groove connector 15G is configured to slidably fit into the groove 15FA of the previous shaft member 15 having at least one side extension 15F having at least one groove 15FA, and at least one side extension Groove connector 15G. The interaction between a groove 15FA of one shaft member 15 and a side extension groove connector 15G of another shaft member 15, facilitates the travel of each shaft member of a plurality of shaft members 15 perpendicularly to the longitudinal axis of the threaded shaft 13, in the direction of the longitudinal axis of the threaded shaft 13 when the girth of the shaft 17 is decreased by the user. Preferably, the side extension groove connector 15G is made with the shaft member 15, however, the side extension groove connector 15G may be made separately and be secured to the shaft member 15. In that case, the side extension groove connector 15G is preferably made of such as, but limited to: plastic, plastic-based, magnet 31, iron-based metal and/or metal material. The side extension 15F having at least one groove 15FA is secured to the shaft member 15 and made with a resilient material such as, but not limited to: plastic and/or plastic-based material. FIG. 36A illustrates a front view of the shaft member 15 having at least one side extension 15F having at least one groove 15FA in its original shape, and at least one side extension groove connector 15G, when the shaft 17 of the device 10 is at its minimum girth. FIG. 36B illustrates a back view of the shaft member 15 having at least one side extension 15F having at least one side extension groove 15FA in its original shape, and at least one side extension groove connector 15G, when the shaft 17 of the device 10 is at its minimum girth. FIG. 36C illustrates a front view of the shaft member 15 having at least one side extension 15F having at least one groove 15FA deformed elastically from its original shape, and at least one side extension groove connector 15G, when the shaft 17 of the device 10 is at its maximum girth. FIG. 36D illustrates a back view of the shaft member 15 having at least one side extension 15F having at least one groove 15FA deformed elastically from its original shape, and at least one side extension groove connector 15G, when the shaft 17 of the device 10 is at its maximum girth. FIG. 37A illustrates a perspective view of the device 10 with the shaft 17 at its minimum girth in this embodiment (sheath 16 not illustrated). FIG. 37B illustrates a perspective view of the device 10 with the shaft 17 at its maximum girth in this embodiment (sheath 16 not illustrated).

Figure 38A:
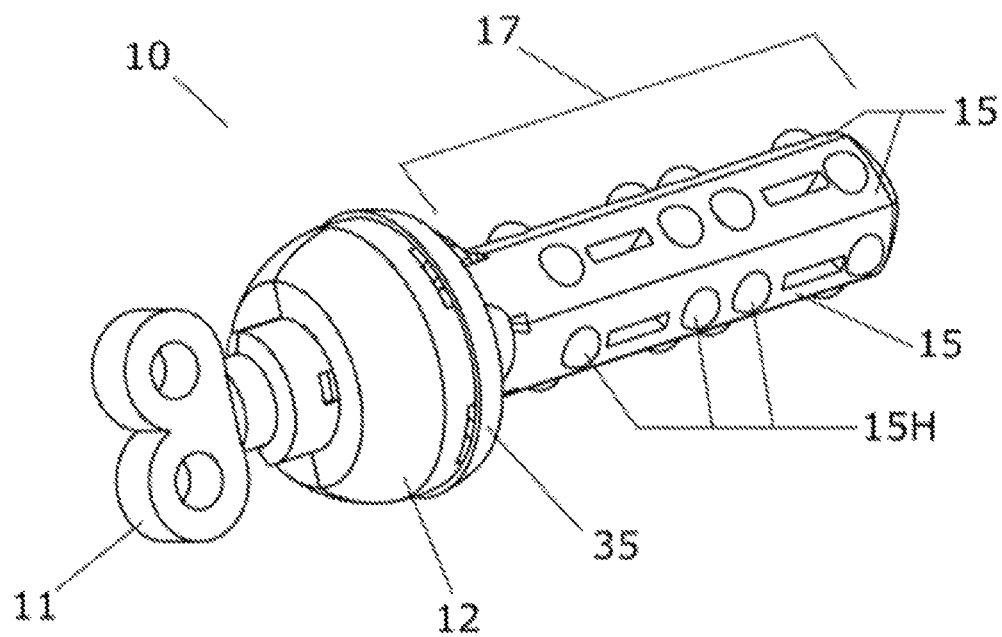
FIG. 38A illustrates a perspective view of the device 10 with the shaft 17 at its minimum girth according to an embodiment of the device 10 (sheath 16 not illustrated in FIG. 38A).
Figure 38B:
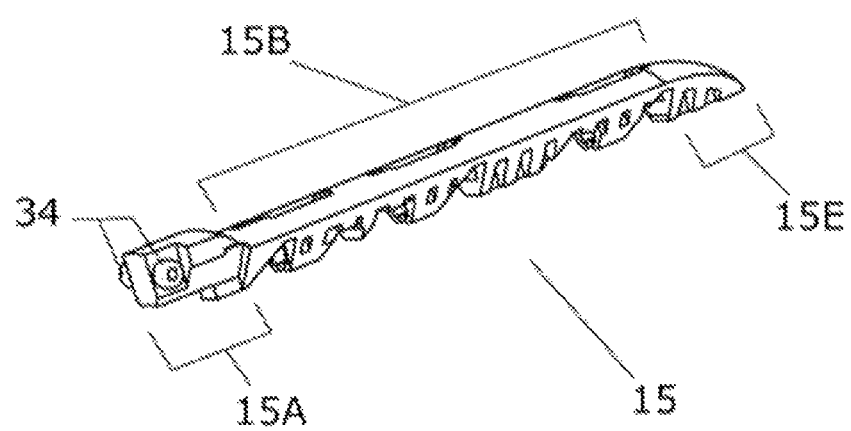
FIG. 38B illustrates a perspective view of a shaft member 15 according to an embodiment.

In another embodiment as illustrated in FIG. 38A, at least one shaft member 15 may comprise at least one shaft member orifice stimulation protrusion 15H. The shalt member orifice stimulation protrusion 15H stimulates the body orifice through the sheath 16, during the utilization of the device 10. FIG. 38A illustrates a perspective view of the device 10 with the shaft member 17 at its minimum girth in this embodiment (sheath 16 not illustrated).

In another embodiment (not illustrated), the shaft member 15 may comprise at least one spring. Preferably, the spring is such as, but not limited to: a tensile spring, a circular spring, a circular spring clamp and/or a circular spring clamp clip made of such as, but not limited to: iron-based, metal, plastic, and/or plastic-based material. Preferably, the spring connects a plurality of shaft members 15 together, at least one shaft member 15 to the housing 12, and/or at least one shaft member 15 to at least one module 14. The spring facilitates the travel of at least one shaft member 15, or of each shaft member 15 of a plurality of shaft members 15 perpendicularly to the longitudinal axis of the threaded shaft 13, in the direction of the longitudinal axis of the threaded shaft 13, when the girth of the shaft 17 is decreased by the user, and reinforces the global structure of the device 10.

Sheath

Figure 39A:
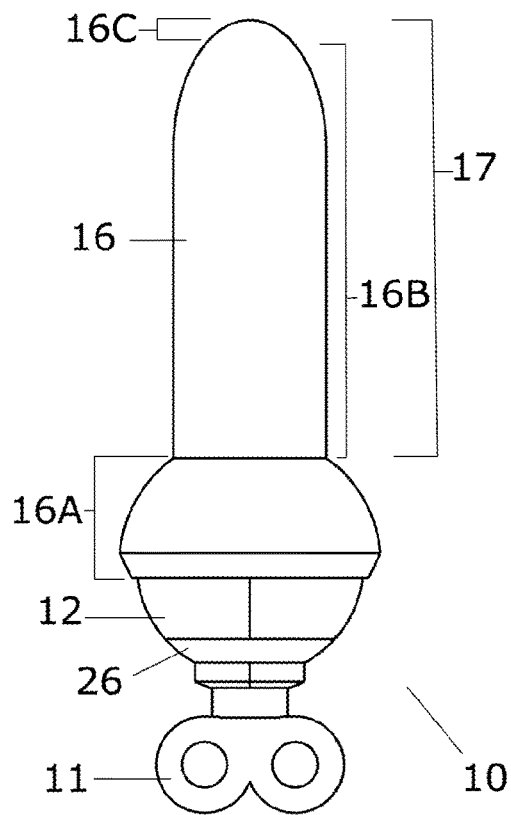
FIG. 39A is a front view of the device 10 with the shaft 17 at its minimum girth according to an embodiment of the device 10.
Figure 39B:
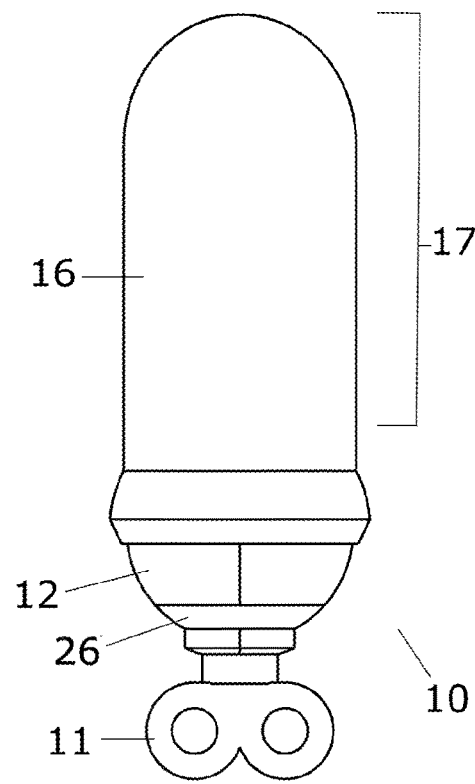
FIG. 39B is a front view of the device 10 with the shaft 17 at its maximum girth according to an embodiment of the device 10.
Figure 39C:
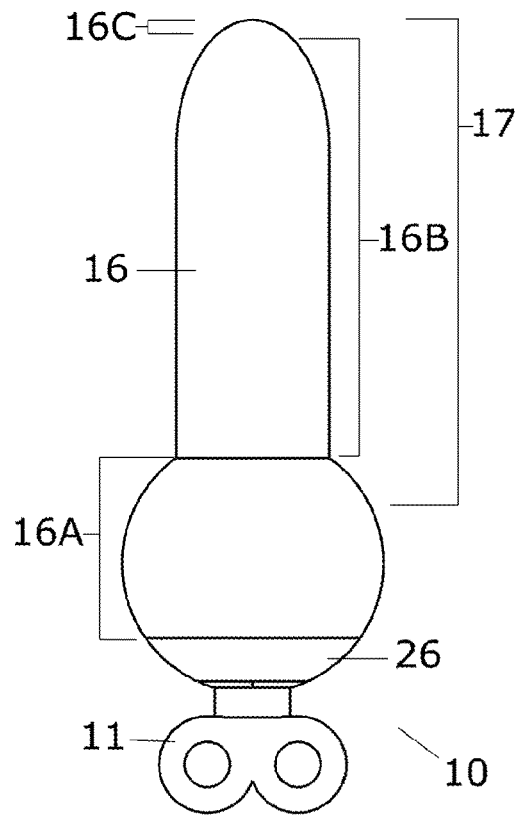
FIG. 39C is a front view of the device 10 with the shaft 17 at its minimum girth according to an embodiment of the device 10.
Figure 39D:
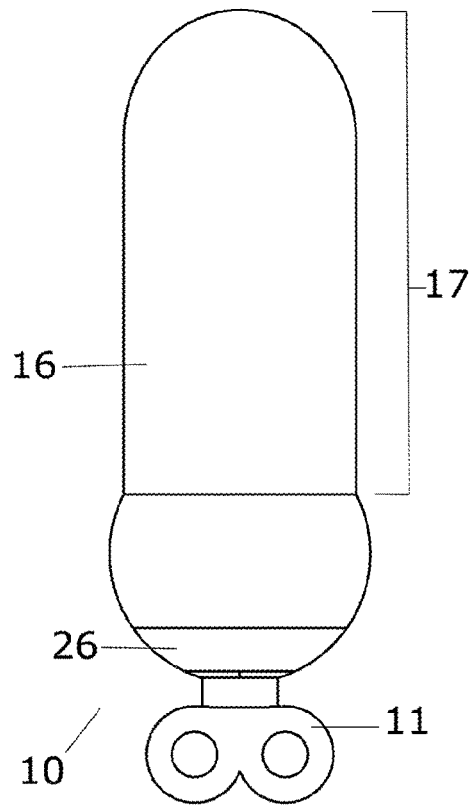
FIG. 39D is a front view of the device 10 with the shaft 17 at its maximum girth according to an embodiment of the device 10.

In a preferred embodiment, the device 10 comprises one sheath 16 having a first end 16A, a middle section 16B, a tip end 16C, and a sheath girth. In a preferred embodiment the sheath 16 is configured to surround the plurality of shaft members 15, however, the first end 16A of the sheath 16 may be configured to surround partially the housing 12 (as illustrated in FIG. 1A, FIG. 1B, FIG. 39A, and FIG. 39B) or the entire housing 12 (as illustrated in FIG. 39C and FIG. 39D). FIG. 1A is a front view of the device 10 with the shaft 17 at its minimum girth according to a preferred embodiment of the device 10. FIG. 1B is a front view of the device 10 with the shaft 17 at its maximum girth according to a preferred embodiment of the device 10. FIG. 39A is a front view of the device 10 with the shaft 17 at its minimum girth according to a preferred embodiment of the device 10. FIG. 39B is a front view of the device 10 with the shaft 17 at its maximum girth according to a preferred embodiment of the device 10. FIG. 39C is a front view of the device 10 with the shaft 17 at its minimum girth to a preferred embodiment of the device 10. FIG. 39D is a front view of the device 10 with the shaft 17 at its maximum girth to a preferred embodiment of the device 10.

Preferably, the sheath 16 is made with a soft and resilient material such as, but not limited to: silicone, silicone-based and/or rubber material. Preferably, the sheath 16 is made with at least one coloration additive, however, the sheath 16 may be made with no coloration additive. The sheath 16 may comprise at least one additive such as, but not limited to: a perfume additive, a fluorescent additive, a glowing additive or a conductive additive. The sheath 16 may be configured with a color code and/or a serial number to distinguish a device 10 with one configuration, one girth adjustment performance and/or one size from another device 10 having another configuration, girth adjustment performance and/or size, to facilitate the utilization for the user of several devices 10. The sheath 16 may be configured with at least one visual and/or tactile indication to indicate to the user how to use the device 10. Preferably, the sheath 16 is secured to the plurality of shaft members 15 and/or the housing 12, however, the sheath 16 may be configured to be removably secured to the plurality of shaft members 15 and/or the housing 12, which means that the sheath 16 may be repeatedly secured to the plurality of shaft members 15 and/or the housing 12, then removed from the plurality of shaft members 15 and/or the housing 12, and then secured again to the plurality of shaft members 15 and/or the housing 12. Preferably, the length of the sheath 16, from the first end 16A to the tip end 16C is greater than 1 inch. Preferably, the sheath girth of the sheath 16, when the shaft 17 of the device 10 is at its minimum girth, is greater than 0.41 inches. The sheath girth is the girth calculated with the outside diameter of the cylindrical shape formed by the middle section 16B of the sheath 16. When the user rotates the controller 11 in one direction, clockwise or counter-clockwise, to increase the girth of the shaft 17, this direction of rotation of the controller 11 is referred to as the "the direction of increase of the sheath girth". When the user rotates the controller 11 rotates the controller 11 in one direction clockwise or counter-clockwise to decrease the girth of the shaft 17, this direction of rotation of the controller 11 is referred to as the "the direction of decrease of said sheath girth". Preferably, the tip end 16C closes the device 10 as illustrated in FIG. 1C and FIG. 1D. FIG. 1C is a top view of the device 10 with the shaft 17 at its minimum girth according to a preferred embodiment of the device 10. FIG. 1D is a top view of the device 10 with the shaft 17 at its maximum girth according to a preferred embodiment of the device 10.

Figure 40A:
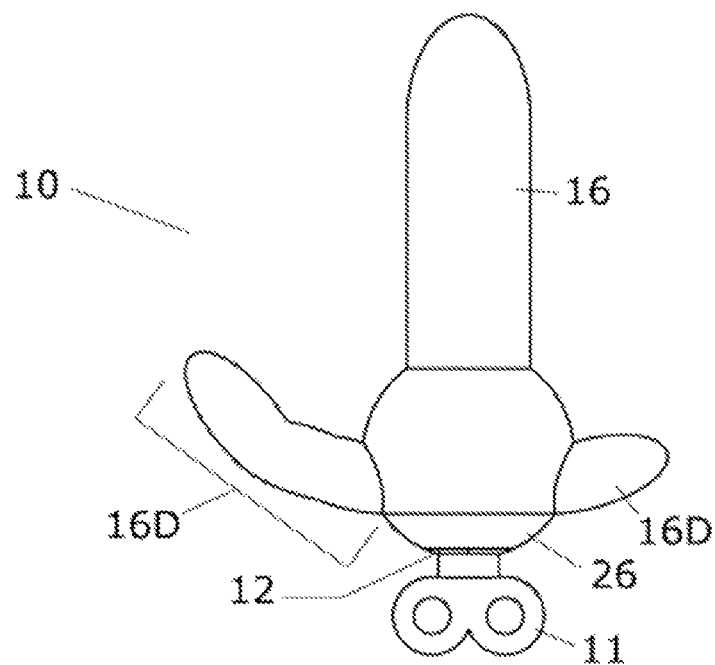
FIG. 40A illustrates a front view of the device 10 with the shaft at its minimum girth according to an embodiment of the device 10.
Figure 40B:
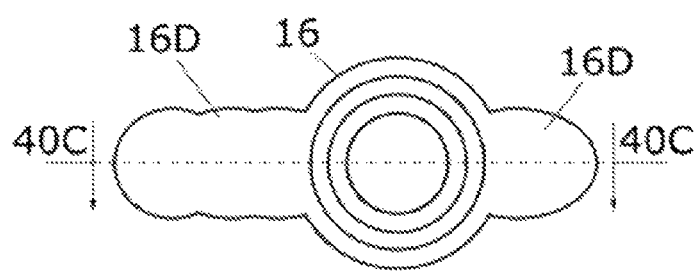
FIG. 40B illustrates a bottom view of the sheath 16 according to an embodiment.
Figure 40C:
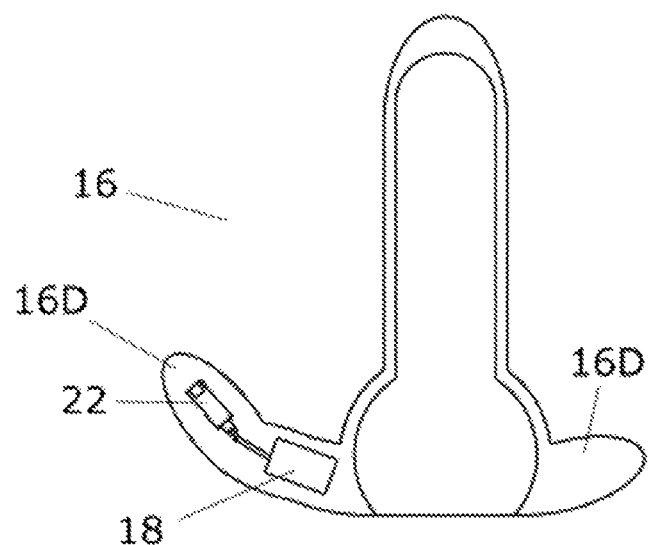
FIG. 40C illustrates a section view of FIG. 40B.

In another embodiment, as illustrated in FIG. 40 and FIG. 41, the sheath 16 may comprise at least one sheath multi-purpose protrusion 16D. The sheath multi-purpose protrusion 16D prevents the device 10 to rotate inside the body orifice when the user performs the adjustment of the device 10, by pressing against the nearest body part of the body orifice where the shaft 17 of the device 10 is inserted. The sheath multi-purpose protrusion 16D is also a handle to enhance the utilization of the device 10. The sheath multi-purpose protrusion 16D may comprise: an electronic part 18 (illustrated in FIG. 40C), a vibration motor 22 connected to an electronic part 18 (illustrated in FIG. 40C), a heating element connected to an electronic part 18 (not illustrated), a heart rate monitor connected to an electronic part 18 (not illustrated), an electrical stimulation electrode connected to an electronic part 18 (not illustrated), a penis ring (not illustrated), a weight 32 (not illustrated in this embodiment), and/or a girth adjustment indicator 23 (not illustrated in this embodiment). The sheath multi-purpose protrusion 16D also prevents over-insertion of the device 10 inside the body orifice. The sheath multi-purpose protrusion 16D may also be configured to stimulate another body part (such as a vagina when the device 10 is inserted into an anus) during the utilization of the device 10. The sheath multi-purpose protrusion 16D may also be configured to be inserted into another body orifice (such as a vagina when the device 10 is inserted into an anus) during the utilization of the device 10. The sheath multi-purpose protrusion 16D is preferably made with the sheath 16, however, the sheath multi-purpose protrusion 16D may be made separately and configured to be removably secured to the sheath 16, which means that sheath multi-purpose protrusion 16D may be repeatedly secured to the sheath 16, then removed from the sheath 16, and then secured again to the sheath 16. In that case, the sheath multi-purpose protrusion 16D is preferably made of such as, but not limited to: plastic, plastic-based, silicone, silicone-based and/or rubber material. FIG. 40A illustrates a front view of the device 10 with the shaft 17 at its minimum girth in this embodiment. FIG. 40B illustrates a bottom view of the sheath 16 in this embodiment. FIG. 40C illustrates a section view of FIG. 40B, FIG. 41 illustrates a perspective view of the device 10 with the shaft 17 at its minimum girth in this embodiment. This embodiment provides others features to the user during the utilization of the device 10.

Figure 42:
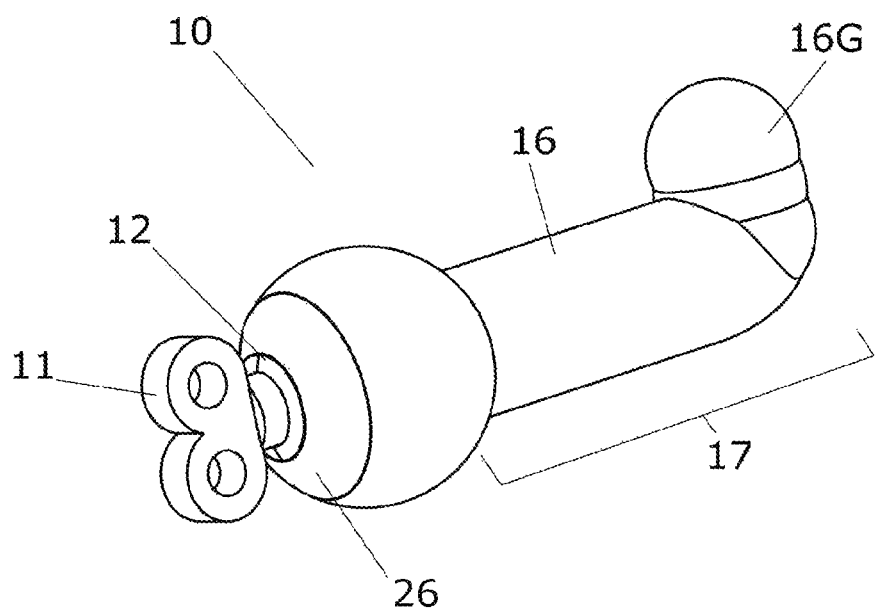
FIG. 42 illustrates a perspective view of the device 10 with the shaft 17 at its minimum girth according to an embodiment of the device 10.

In another embodiment, as illustrated in FIG. 42, the sheath 16 may comprise at least one prostate stimulation protrusion 16G. The prostate stimulation protrusion 16G stimulates the prostate via the anal body orifice, during the utilization of the device 10 (for example in a male anus body orifice). FIG. 42 illustrates a perspective view of the device 10 with the shaft 17 at its minimum girth in this embodiment.

In another embodiment, the sheath 16 may comprise at least one: an electronic part 18 as illustrated in FIG. 50, a vibration motor 22 connected to an electronic part 18 as illustrated in FIG. 40C, a girth adjustment indicator 23 (not illustrated in this embodiment), a heating element connected to an electronic part 18 (not illustrated), a heart rate monitor unit connected to an electronic part 18 (not illustrated), an electrical stimulation electrode connected to an electronic part 18 (not illustrated), a penis ring (not illustrated), and/or a weight 32 (not illustrated in this embodiment). This embodiment provides others features to the user during the utilization of the device 10.

Figure 48:
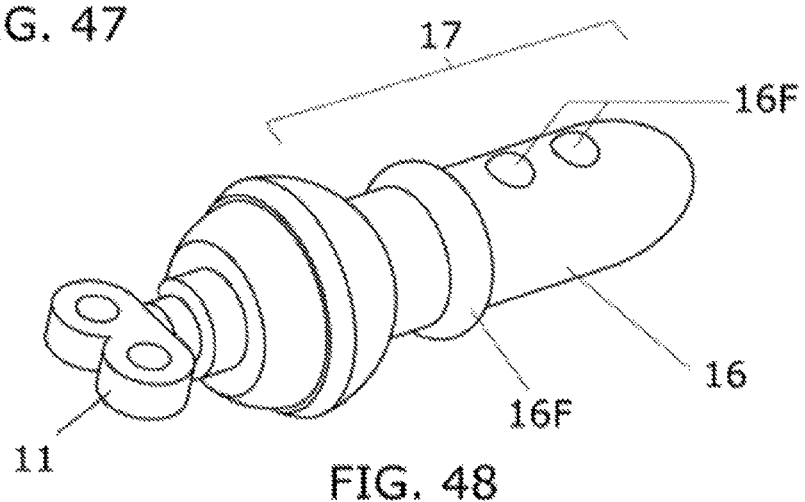
FIG. 48 illustrates a perspective view of the device 10 with the shaft 17 at its minimum girth according to an embodiment of the device 10.

In another embodiment; as illustrated in FIG. 48, the sheath 16 may comprise at least one sheath orifice stimulation protrusion 16F. The sheath orifice stimulation protrusion 16F stimulates the body orifice, during the utilization of the device 10 by the user. As illustrated in FIG. 48, the sheath orifice stimulation protrusion 16F may also be configured to prevent undesired expulsion of the device 10 from the body orifice during the utilization. FIG. 48 illustrates a perspective view of the device 10 with the shaft 17 at its minimum girth in this embodiment.

Electronic Part

In another embodiment, the device 10 may comprise at least one electronic part 18 having at least one electric battery and at least one component such as, but not limited to: an electronic circuit, a microprocessor, an encoder, a rotation sensor, a transmitter, a receiver, a light-emitting diode (LED), a timer, an electric speaker, an electrical wire and an electronic controller such as, but not limited to: a knob, a push-button, a switch and/or a tactile switch. The electric battery of the electronic part 18 may be single-use or rechargeable multiple times by wire and/or wireless charging. The electronic part 18 may be configured to indicate to the user (by sound and/or visually) the state of charge of the electric battery and/or indicate other information (such as information from a heart rate monitor). The electronic circuit may be configured with predetermined operative functions. The electronic part 18 may be configured to operate with such as, but not limited to: an enclosed electric motor 19, a vibrator 22, a girth adjustment indicator 23, a heating element (not illustrated), a heart rate monitor unit (not illustrated) and/or an electrical stimulation electrode (not illustrated). The electronic part 18 is preferably secured on the device 10, however, the electronic part 18 (or at least one of its components) may be configured to be removably secured the device 10, which means that the electronic part 18 (or at least one of its components) may be repeatedly secured to the device 10, then removed from the device 10, and then secured again on the device 10. The electronic part 18 is operated by the user via the electronic controller of the electronic part 18 and/or via a computer program designed to run on a desktop computer and/or mobile device (not illustrated).

Enclosed Electric Motor

In another embodiment, the device 10 may comprise an enclosed electric motor 19 having at least one motor having a motor shaft 19A, a motor housing 19B and an electronic part 18. The motor having a motor shaft 19A is powered by direct current or by alternating current. The enclosed electric motor 19 may comprise a planetary gear system 19C (as illustrated in FIG. 15) to reduce the speed rotation of the motor shaft of the motor having a motor shaft 19A, or increase the torque of the motor having a motor shaft 19A.

The user operates the enclosed electric motor 19 via the electronic part 18 of the enclosed electric motor 19. The motor housing 19B may be secured to the housing 12, or removably secured to the housing 12, which means that the motor housing 19B may be repeatedly secured to the housing 12, then removed from the housing 12, and then secured again on the housing 12. The motor shaft of the motor having a motor shaft 19A of the enclosed electric motor 19 is preferably secured to the first end 11A of the controller 11, however, the motor shaft of the motor having a motor shaft 19A may be removably secured to the first end 11A of the controller 11, which means that the motor shaft of the motor having a motor shaft 19A may be repeatedly secured to the first end 11A of the controller 11, then removed from the first end 11A of the controller 11, and then secured again to the first end 11A of the controller 11. The motor housing 19B is preferably made of a rigid material such as, but not limited to: plastic, plastic-based, hard silicone, metal, iron-based metal, glass, and/or wood material, however, the motor housing 19B may be made in combination with a soft material such as, but not limited: silicone, silicone-based, rubber, and/or leather material.

Vibration Motor

In another embodiment, the device 10 may comprise at least one vibration motor 22. The vibration motor 22 preferably is such as, but not limited to: an eccentric rotating mass vibration (ERM) type and/or a linear resonant actuator (LRA) type. Preferably, the vibration motor 22 is configured to be connected to the electronic part 18 via electrical wire (not illustrated). The vibration motor 22 is preferably operated via the electronic part 18. The vibration motor 22 may be configured to perform such as but not limited to: low, medium and/or high amplitude and low, medium and/or high frequency and may be configured to perform substantially noiselessly. The vibrations made by the vibration motor 22 while operated stimulate muscles and ligaments of the body orifice region and therefore enhance the dilation and stretch of the body orifice during the utilization of the device 10.

Girth Adjustment Indicator

In another embodiment, the device 10 may comprise at least one girth adjustment indicator 23. The girth adjustment indicator 23 indicates by sound, in a tactile manner, and/or visually to the user, the level and/or limits of the adjustment of the device 10. The girth adjustment indicator 23 is such as, but not limited to: a sound girth adjustment indicator, in a tactile manner girth adjustment indicator and/or a visual girth adjustment indicator. Preferably, the girth adjustment indicator 23 is such as, a mechanical type, meaning that it does not require electronic component and power supply to be functional, however, the girth adjustment indicator 23 may be electronical type, meaning that it does require at least one electronic component and power supply to be functional. In the case that the girth adjustment indicator 23 is electronical type, the girth adjustment indicator 23 may comprise an electronic part 18.

Heating Element

In another embodiment the device 10 may comprise at least one heating element (not illustrated). The heating element converts energy received from the electronic part 18 into heat. The heating element transfers heat to the skin of the body orifice where the device 10 is inserted (directly or via the sheath 16, when preferably the sheath 16 comprises a conductive additive). The heating element is preferably such as, but not limited to: an electrical heating element and/or a polymer PTC heating element. The heating element is configured to be connected to the electronic part 18 via electrical wire (not illustrated). The heating element is preferably operated via the electronic part 18. The heat made by the heating element while operated stimulates muscles and ligaments of the body orifice region and therefore enhances the dilation and stretch of the body orifice during the utilization of the device 10.

Heart Rate Monitor

In another embodiment the device 10 (not illustrated) may comprise at least one heart rate monitor. The heart rate monitor may comprise at least one component such as, but not limited to: a transmitter, and/or a receiver, such that when a heartbeat and/or changes in blood flow is detected by the transmitter, a signal is transmitted (by electrical wire, by wireless technology, and/or by low-power radio link) to the receiver to determine the current heart rate. The heart rate monitor may be configured with a light-emitting diode (LED) to measure changes in blood flow through the skin. The heart rate monitor may be configured to measures in real time such as, but not limited to: heart rate, pulse, and/or oxygen saturation, of the body of the body orifice where the device 10 is inserted during the utilization. The heart rate monitor is connected to the electronic part 18 via electrical wire (not illustrated). This embodiment provides others features to the user. The heart rate monitor is preferably operated via the electronic part 18.

Electrical Stimulation Electrode

In another embodiment the device 10 may comprise at least one electrical stimulation electrode. The electrical stimulation electrode delivers electric impulses generated by the electronic part 18 in the skin of the body orifice where the device 10 is inserted (directly or via the sheath 16, when preferably the sheath 16 comprises a conductive additive). The electrical stimulation electrode is configured to be connected to the electronic part 18 via electrical wire (not illustrated). The electrical stimulation electrode is preferably operated via the electronic part 18. This embodiment provides others features to the user, such as but not limited to: pelvic floor physical therapy.

Weight

In another embodiment, the device 10 may comprise at least one weight 32 (as illustrated in FIG. 29B). The weight 32 has preferably a weight greater than or equal to 0.07 ounces. This embodiment provides others features to the user, such as but not limited to: pelvic floor physical therapy. FIG. 29B illustrates a part of the housing 12 in this embodiment.

Penis Ring

In another embodiment the device 10 may comprise at least one penis ring (not illustrated). The penis ring is preferably secured to the device 10, however, the penis ring may be configured to be removably secured to the device 10, which means that the penis ring may be repeatedly secured to the device 10, then removed from the device 10, and then secured again to the device 10. The penis ring is preferably made of such as, but not limited to: plastic, plastic-based, hard silicone, silicone, silicone-based, rubber, glass, leather, iron-based metal, metal and/or wood material. Preferably, the penis ring is made with at least one coloration additive, however, the penis ring may be made with no coloration additive. The penis ring may be configured with a color code and/or a serial number to distinguish a device 10 with one configuration, one girth adjustment performance and/or one size from another device 10 having another configuration, girth adjustment performance and/or size, to facilitate the utilization for the user of several devices 10. The penis ring provides others features to the user such as, but not limited to: a restriction of the flow of blood from the erect penis in order to produce a stronger erection or to maintain an erection for a longer period of time, and/or a ring to hold via the penis, the device 10 inside a body orifice to prevent undesired movement of the device 10 during the utilization. The penis ring may be considerate as a handle to facilitate the utilization of the device 10 and the removal from a body orifice of the device 10, and therefore useful for male and female. The penis ring may comprise: an electronic part 18 (not illustrated in this embodiment), a vibration motor 22 connected to an electronic part 18 (not illustrated in this embodiment), a heating element connected to an electronic part 18 (not illustrated), a heart rate monitor connected to an electronic part 18 (not illustrated), an electrical stimulation electrode connected to an electronic part 18 (not illustrated), a weight 32 (not illustrated in this embodiment), and/or a girth adjustment indicator 23 (not illustrated in this embodiment).

Closure Element

In another preferred embodiment, as illustrated from FIG. 39 to FIG. 43, the device 10 comprises a closure element 26. Preferably, the closure element 26 is made of such as, but not limited to: plastic, plastic-based, hard silicone, silicone, silicone-based, rubber, glass, iron-based metal, metal and/or wood material. Preferably, the closure element 26 is configured to receive the controller 11 and be connected to the sheath 16 and/or the housing 12. As illustrated in FIG. 43A, the closure element 26 may comprise at least one connector 26A such as, but not limited to: a cantilever snap-fit. In that case, the housing 12 and/or the sheath 16 are configured to receive the connector 26A. Preferably, the closure element 26 is made with at least one coloration additive, however, the closure element 26 may be made with no coloration additive. The closure element 26 may be configured with a color code and/or a serial number to distinguish a device 10 with one configuration, one girth adjustment performance and/or one size from another device 10 having another configuration, girth adjustment performance and/or size, to facilitate the utilization for the user of several devices 10. The closure element 26 prevents contamination such as, but not limited to: dust, from entering inside the device 10. The closure element 26 may also be an alternative to fix the sheath 16 to the housing 12 by pressing the sheath 16 against the housing 12. FIG. 43A illustrates a perspective view of the closure element 26 in one embodiment. FIG. 43B illustrates a perspective view of the closure element 26 in one embodiment.

Resilient Band

Figure 44A:
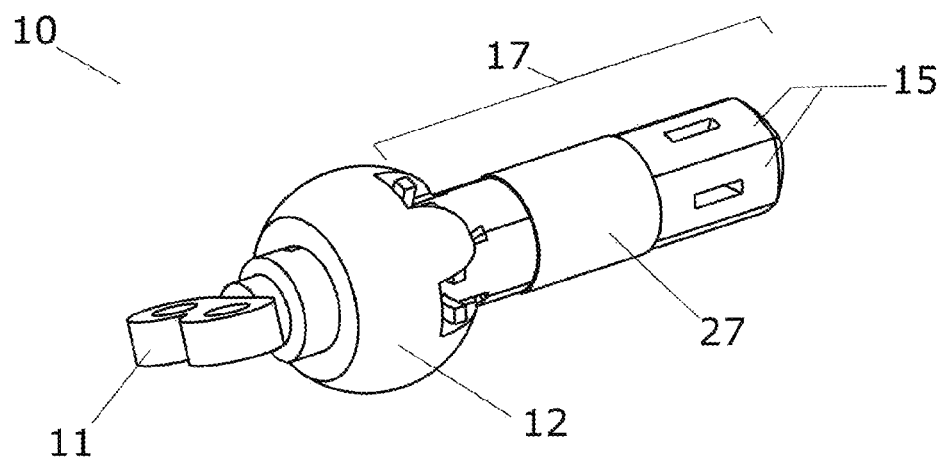
FIG. 44A illustrates a perspective view of the device 10 with the shaft 17 at its minimum girth according to an embodiment of the device 10 (sheath 16 not illustrated in FIG. 44A).
Figure 44B:
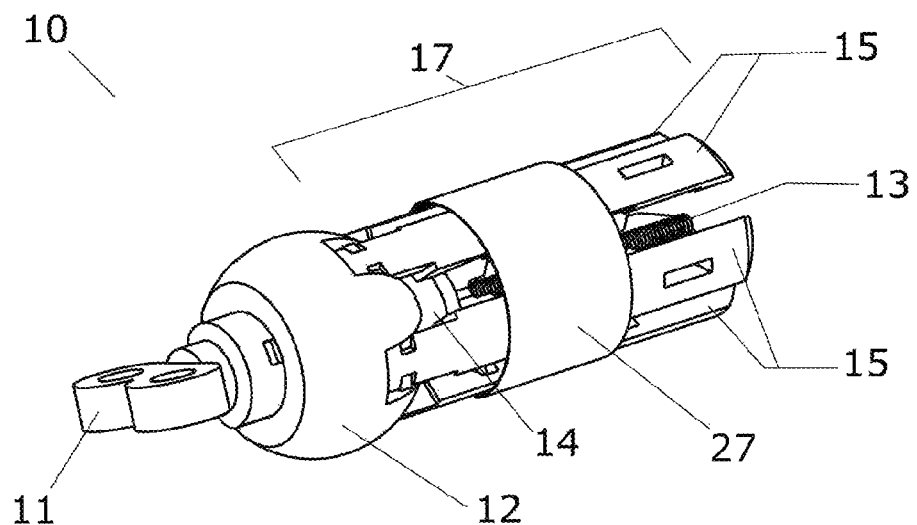
FIG. 44B illustrates a perspective view of the device 10 with the shaft 17 at its maximum girth according to an embodiment of the device 10 (sheath not illustrated in FIG. 44B).

In another embodiment, as illustrated in FIG. 44, the device 10 may comprise at least one resilient band 27. Preferably, the resilient band 27 is made of a resilient material such as, but not limited to: rubber, silicone and/or silicone based material. Preferably, the width of the resilient band 27 is greater than 0.05 inches. Preferably, the resilient band 27 surrounds the plurality of shaft members 15. The resilient band 27 facilitates the travel of each shaft member 15 of the plurality of shaft members 15 perpendicularly to the longitudinal axis of the threaded shaft 13, in the direction of the longitudinal axis of the threaded shaft 13, when the girth of the shaft 17 is decreased by the user, and reinforces the global structure of the device 10. FIG. 44A illustrates a perspective view of the device 10 with the shaft 17 at its minimum girth in this embodiment. FIG. 44B illustrates a perspective view of the device 10 with the shaft 17 at its maximum girth in this embodiment.

Strap

Figure 46:
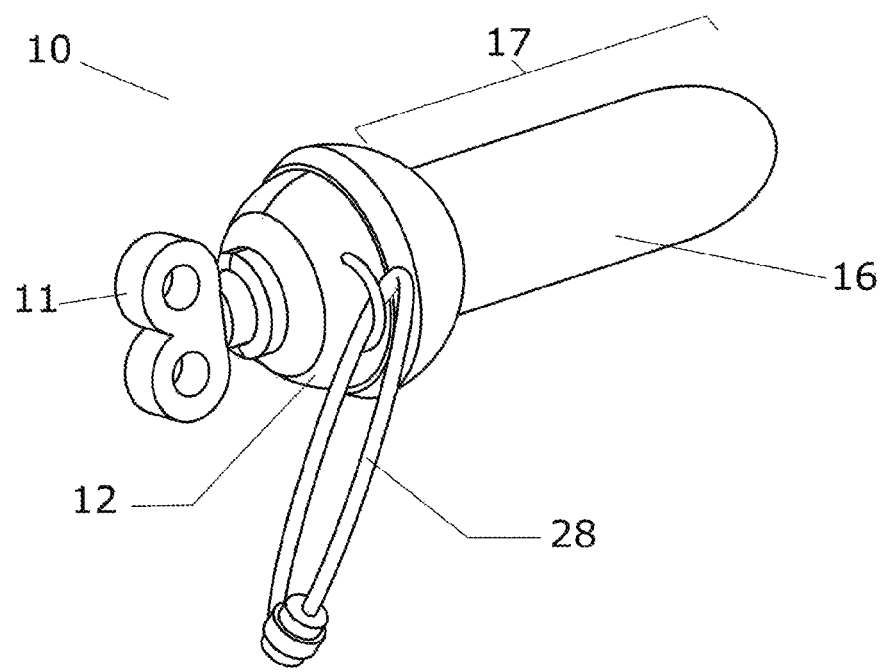
FIG. 46 illustrates a perspective view of the device 10 with the shaft 17 at its minimum girth according to an embodiment of the device 10.
Figure 47:
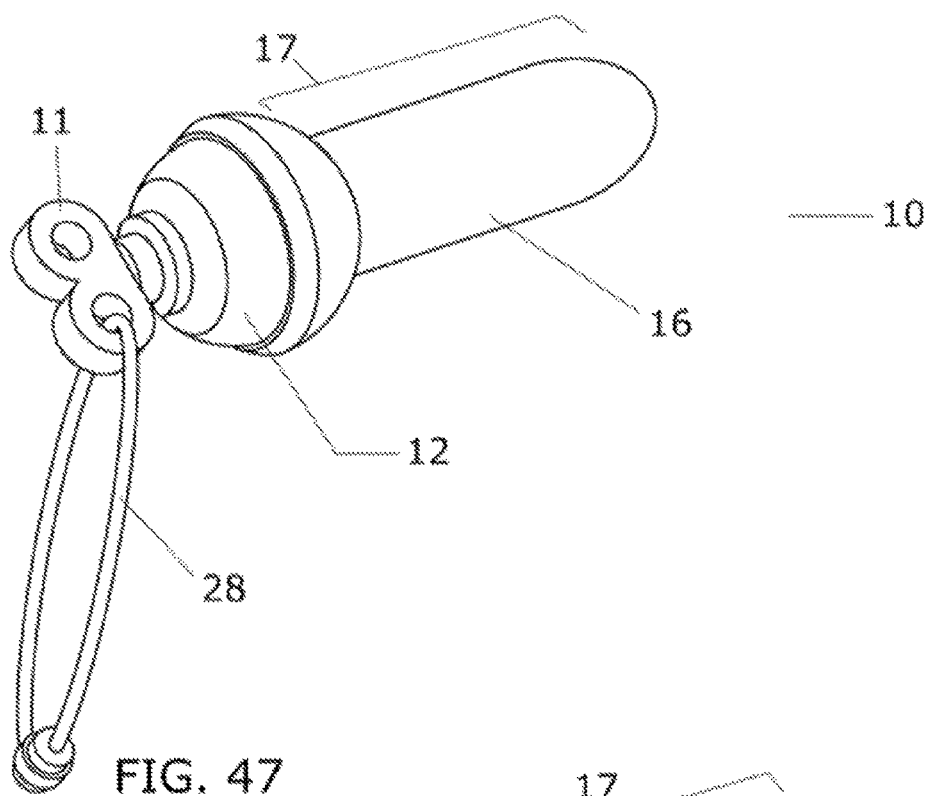
FIG. 47 illustrates a perspective view of the device 10 with the shaft 17 at its minimum girth according to an embodiment of the device 10.

In another embodiment, the device 10 may comprise at least one strap 28, as illustrated in FIG. 46 and FIG. 47. Preferably, the strap 28 is made of such as, but not limited to: plastic, plastic-based, silicone, rubber, leather, fabric, iron-based metal, metal and/or wood material. Preferably, the strap 28 is made with at least one coloration additive, however, the strap 28 may be made with no coloration additive. The strap 28 may be configured with a color code and/or a serial number to distinguish a device 10 with one configuration, one girth adjustment performance and/or one size from another device 10 having another configuration, girth adjustment performance and/or size, to facilitate the utilization for the user of several devices 10. The strap 28 is preferably secured on the device 10, however, the strap 28 may be configured to be removably secured to the device 10, which means that the strap 28 may be repeatedly secured to the device 10, then removed from the device 10, and then secured again to the device 10. The strap 28 may be configured as a handle to facilitate the utilization of the device 10 and the removal from a body orifice of the device 10 and/or configured as a belt that the user may wear around its waist to maintain the device 10 inside a body orifice during the utilization of the device 10. FIG. 46 illustrates a perspective view of the device 10 with the shaft 17 at its minimum girth in this embodiment. FIG. 47 illustrates a perspective view of the device 10 with the shaft 17 at its minimum girth in this embodiment.

Body Skin Protection Element

Figure 49:
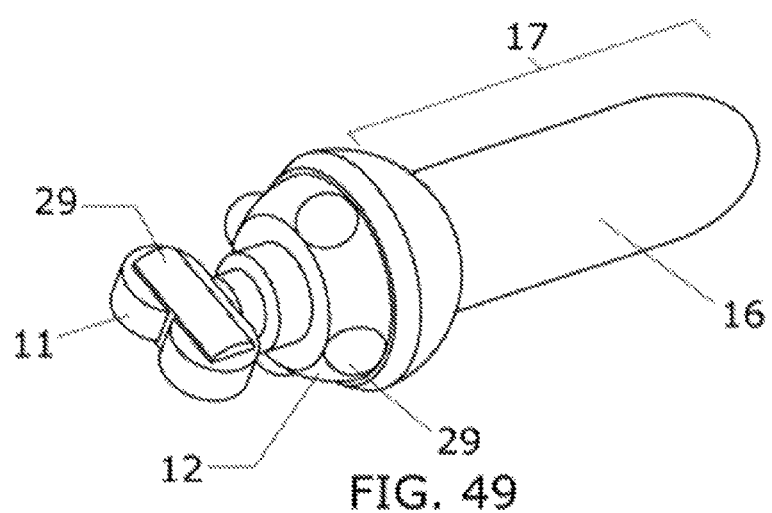
FIG. 49 illustrates a perspective view of the device 10 with the shaft 17 at its minimum girth according to an embodiment of the device 10.

In another embodiment, the device 10 may comprise at least one body skin protection element 29, as illustrated in FIG. 49. The body skin protection element 29 is made of such as, but not limited to: rubber, plastic, plastic-based and/or silicone material. Preferably, the body skin protection element 29 is made with at least one coloration additive, however, the body skin protection element 29 may be made with no coloration additive. The body skin protection element 29 may be configured with a color code and/or a serial number to distinguish a device 10 with one configuration, one girth adjustment performance and/or one size from another device 10 having another configuration, girth adjustment performance and/or size, to facilitate the utilization for the user of several devices 10. The body skin protection element 29 prevents the discomfort of skin friction against the device 10 during the utilization of the device 10. FIG. 49 illustrates a perspective view of the device 10 with the shaft 17 at its minimum girth in this embodiment.

Grip

Figure 52:
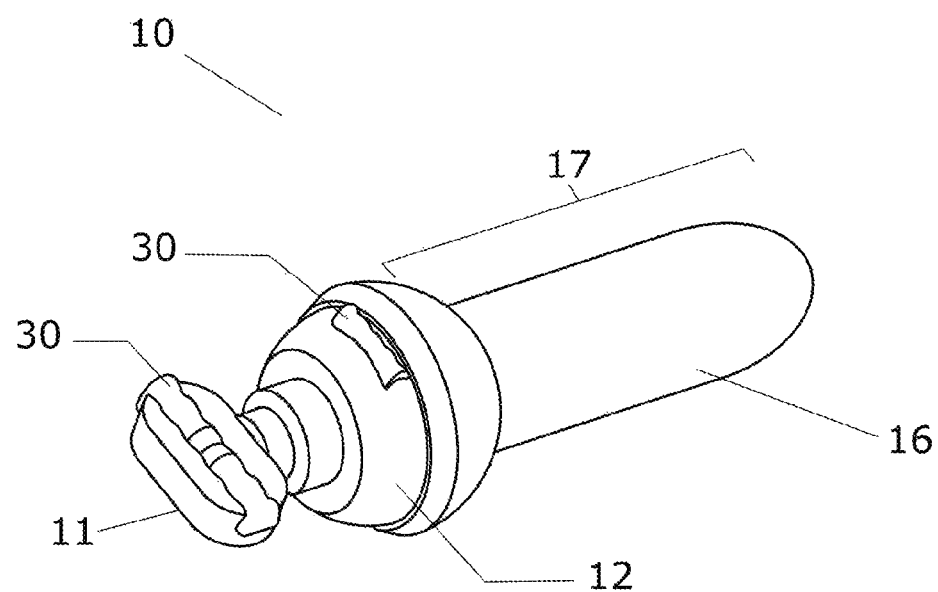
FIG. 52 illustrates a perspective view of the device 10 with the shaft 17 at its minimum girth according to an embodiment of the device 10.

In another embodiment, the device 10 may comprise at least one grip 30, as illustrated in FIG. 52. The grip 30 is preferably made of such as, but not limited to: plastic, plastic-based, hard silicone, silicone, rubber, leather, iron-based metal, metal and/or wood material. Preferably, the grip 30 is made with at least one coloration additive, however, the grip 30 may be made with no coloration additive. The grip 30 may be configured with a color code and/or a serial number to distinguish a device 10 with one configuration, one girth adjustment performance and/or one size from another device 10 having another configuration, girth adjustment performance and/or size, to facilitate the utilization for the user of several devices 10. The grip 30 facilitates the utilization of the device 10 by the user. FIG. 52 illustrates a perspective view of the device 10 with the shaft member 17 at its minimum girth in this embodiment.

Magnet

Figure 53:
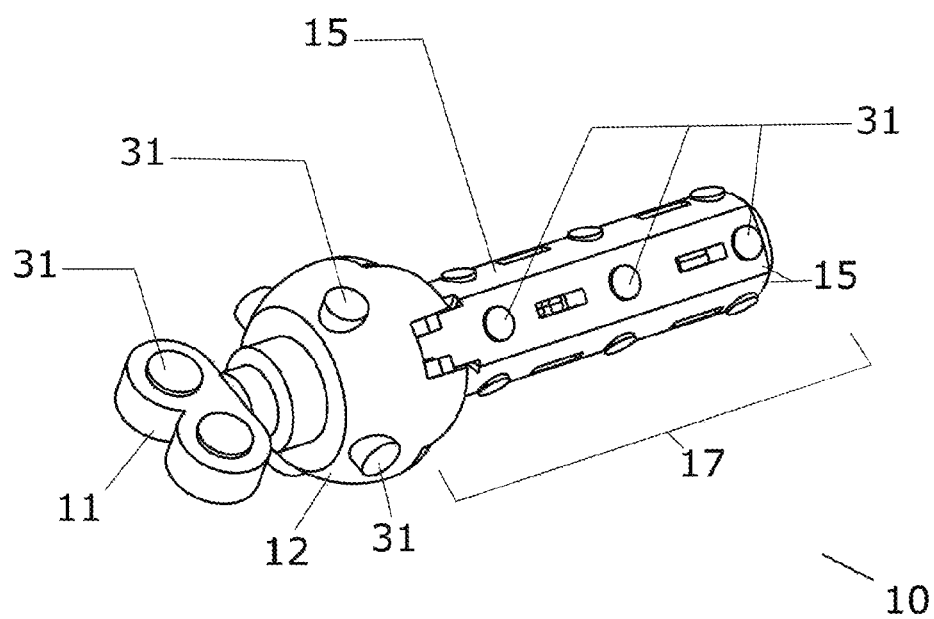
FIG. 53 illustrates a perspective view of the device 10 with the shaft 17 at its minimum girth according to an embodiment of the device 10 (sheath 16 not illustrated in FIG. 53).

In another embodiment, the device 10 may comprise at least one magnet 31, illustrated in FIG. 51 (in one embodiment of the sheath 16), and illustrated in FIG. 53 (sheath 16 not illustrated in FIG. 53). Preferably, the magnet 31 is a material such as, but not limited to: neodymium magnet. The magnet 31 increases the blood flow, relaxes muscles and ligaments of the body orifice region and therefore enhances the dilation and stretch of the body orifice during the utilization of the device 10. FIG. 51A illustrates a bottom view of the sheath 16 in one embodiment. FIG. 51B illustrates a section view of FIG. 51A. FIG. 53 illustrates a perspective view of the device 10 with the shaft member 17 at its minimum girth in this embodiment (sheath 16 not illustrated).

Multiple Shaft

Figure 54A:
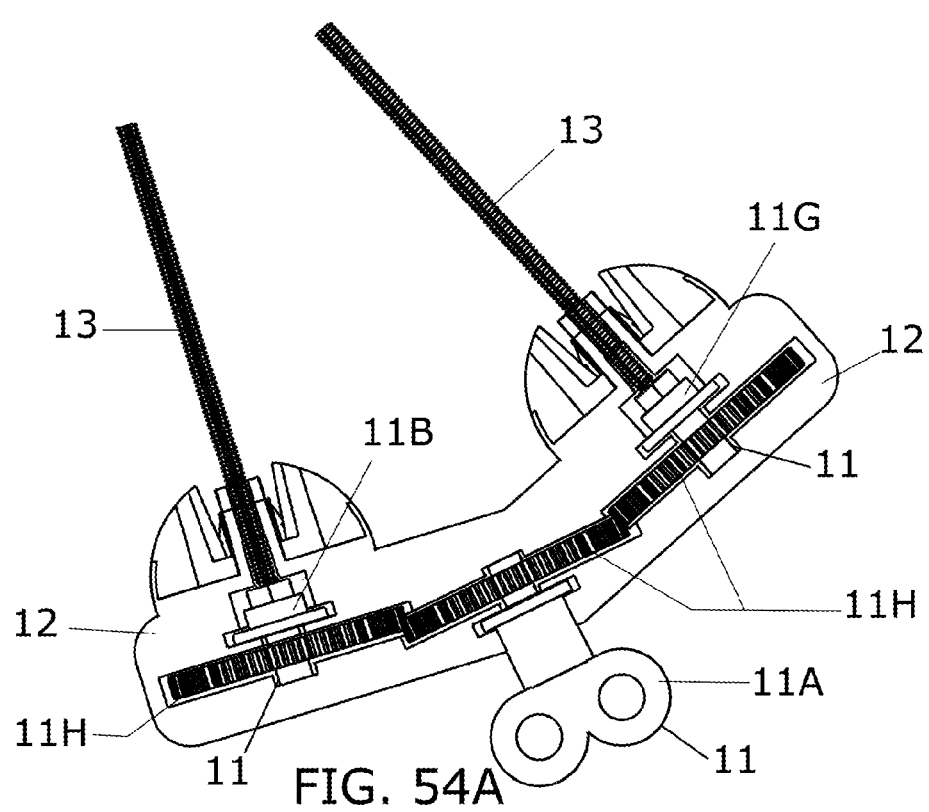
FIG. 54A illustrates a front view of the connection between a controller 11, two threaded shafts 13 and a part of the housing 12 according to an embodiment of the device 10.
Figure 54B:
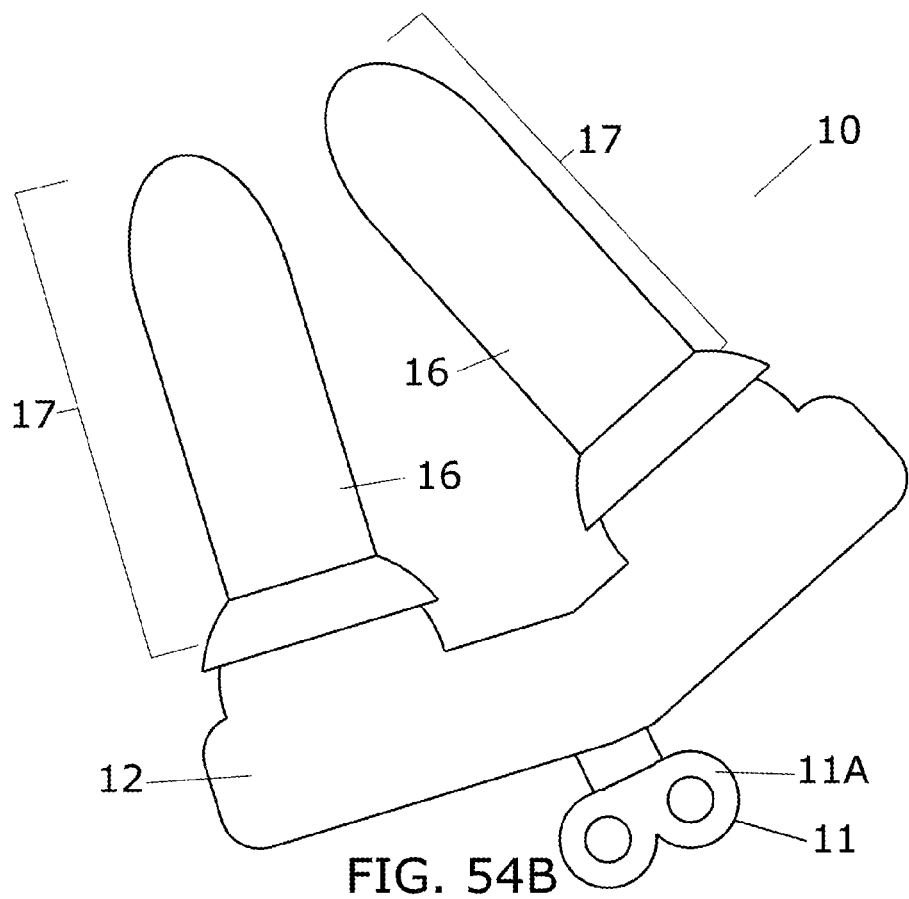
FIG. 54B illustrates a front view of the device 10 with two shafts 17 at their minimum girth according to an embodiment of the device 10.

In another embodiment as illustrated in FIG. 54, the device 10 may comprise a controller 11 having a third end 11G and a plurality of gears 11H, two threaded shafts 13 and two sheaths. In this embodiment, the housing 12 is configured to receive the controller 11 having a third end 11G and a plurality of gears 11H, two threaded shafts 13, and two sheaths 16. This embodiment allows the user to perform the adjustment of the device 10 in two body orifices at the same time, such as, a vagina and an anus. FIG. 54A illustrates the connection between a part of the housing 12, two threaded shafts 13 and the controller 11 having a third end 11G and a plurality of gears 11H, in this embodiment. FIG. 54B illustrates the device 10 with two shafts 17 at their minimum girth in this embodiment.

Figure 55A:
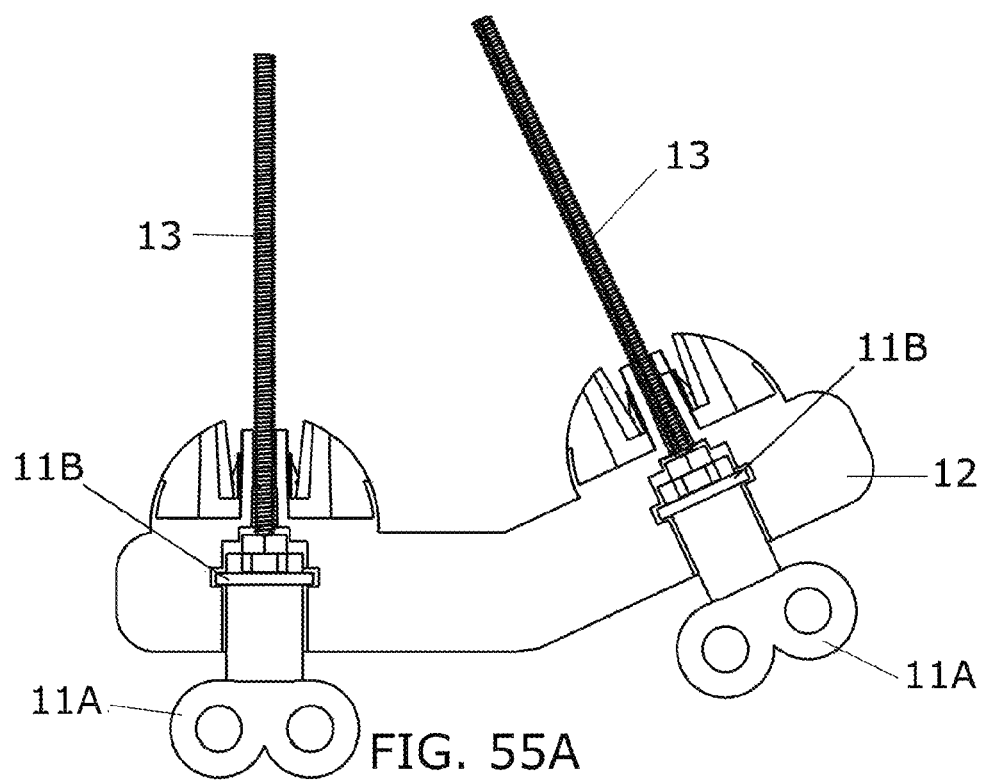
FIG. 55A illustrates a front view of the connection between two controllers 11, two threaded shafts 13 and a part of the housing 12 according to an embodiment of the device 10.
Figure 55B:
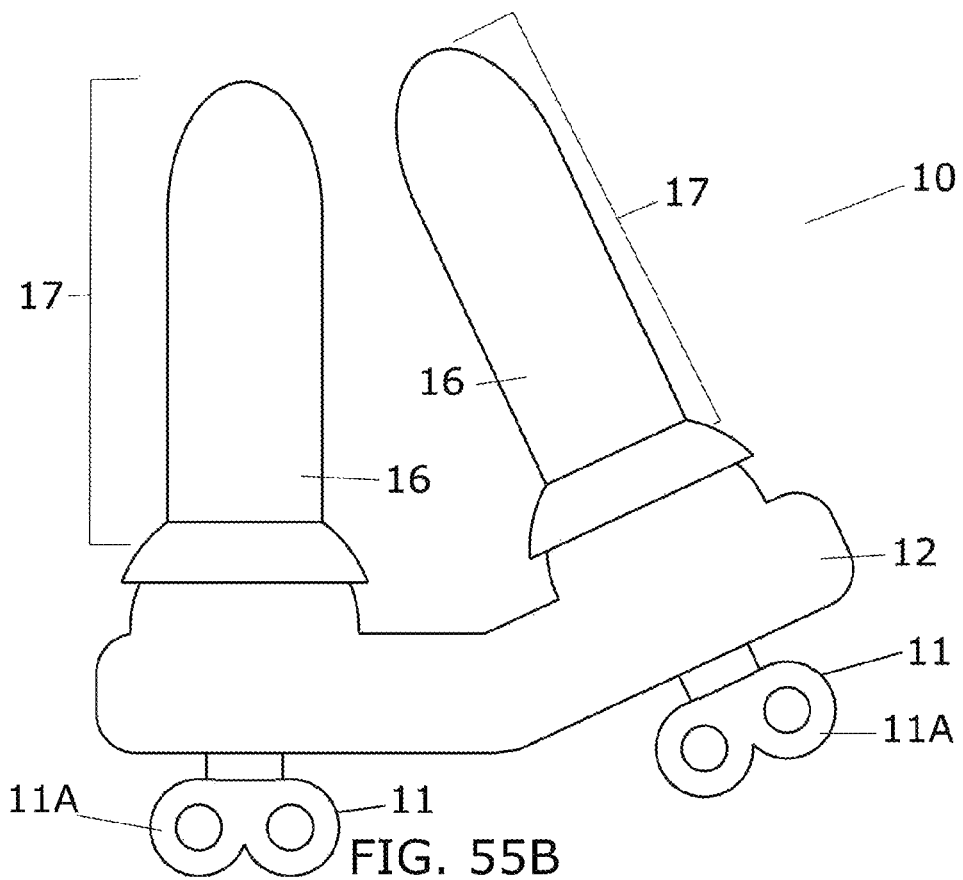
FIG. 55B illustrates a front view of the device 10 with two shafts 17 at their minimum girth according to an embodiment of the device 10.

In another embodiment as illustrated in FIG. 55, the device 10 may comprise two controllers 11, two threaded shafts 13, and two sheaths 16. In this embodiment the housing 12 is configured to receive two controllers 11, two threaded shafts 13, a plurality of shaft members 15 and two sheaths. This embodiment allows the user to perform the adjustment of the device 10 in two body orifices at the same time, such as, a vagina and an anus. FIG. 55A illustrates the connection between two controllers 11, two threaded shafts 13 and a part of the housing 12, in this embodiment. FIG. 55B illustrates the device 10 with two shafts 17 at their minimum girth in this embodiment.

I claim:

1. A girth adjustable device comprising:
a. at least one controller having a first end, and a second end, wherein said first end is connected to said second end, wherein when said first end of said controller rotates clockwise or counter-clockwise, said second end of said controller rotates following the rotation of said first end of said controller;
b. at least one threaded shaft having a first end, a middle section, a second end, and a longitudinal axis, wherein said first end of said threaded shaft is connected to said second end of said controller, wherein when said second end of said controller rotates clockwise or counter-clockwise, said threaded shaft rotates following the rotation of said second end of said controller;
c. a housing having a controller first end, a shaft member second end having a plurality of shaft member grooves and a plurality of shaft member protrusions, and a non-threaded canal, wherein said non-threaded canal receives said threaded shaft, wherein said housing encloses said second end of said controller connected to said first end of said threaded shaft, wherein inside said housing, said second end of said controller connected to said first end of said threaded shaft only rotates clockwise or counter-clockwise around said longitudinal axis of said threaded shaft;
d. at least one module having at least one conical section with a slant height, at least one anti rotation connector selected from a group consisting of: a linear anti-rotation connector, a capital letter T shape anti-rotation connector, and an inclined capital letter T shape anti-rotation connector, and one canal selected from a group consisting of: a threaded canal, a threaded canal having at least one fastener cavity, and a non-threaded canal having at least one fastener cavity, wherein said canal receives said threaded shaft;
e. a plurality of shaft members having a first end having at least one housing groove, a middle section, at least one module cavity with a sloped edge, at least one module connector groove, and a tip end, wherein said plurality of shaft members surrounds said threaded shaft and said module, wherein said shaft member second end having a plurality of shaft member grooves and a plurality of shaft member protrusions of said housing slidably receives said first end of said shaft member, wherein said module cavity with a sloped edge of said shaft member slidably receives said conical section with a slant height of said module, wherein said module connector groove of said shaft member slidably receives said anti-rotation connector of said module; and
f. at least one sheath having a first end, a middle section, a tip end, and a sheath girth, wherein said sheath surrounds said plurality of shaft members or said plurality of shaft members and said housing, wherein said sheath is made with a resilient material, wherein said sheath is secured or removably secured to said plurality of shaft members or to said plurality of shaft members and said housing, wherein when said threaded shaft rotates in the direction of increase of said sheath girth, said module, prevented from rotating by said anti rotation connector of said module slidably connected to said module connector groove of said shaft member, travels along said threaded shaft, said conical section with a slant height of said module slides against said sloped edge of said module cavity with a sloped edge of said shaft member outside of said module cavity with a sloped edge of said shaft member, each said shaft member of said plurality of shaft members travels perpendicularly to said longitudinal axis of said threaded shaft in the opposite direction of said longitudinal axis of said threaded shaft, said sheath deforms elastically from its original shape, said sheath girth increases, wherein when said sheath girth has increased, wherein when said threaded shaft rotates in the direction of decrease of said sheath girth, said module, prevented from rotating by said anti rotation connector of said module slidably connected to said module connector groove of said shaft member, travels back along said threaded shaft, said conical section with a slant height of said module slides back against said sloped edge of said module cavity with a sloped edge of said shaft member inside of said module cavity with a sloped edge of said shaft member, said sheath retrieving its original shape, each said shaft member of said plurality of shaft members travels perpendicularly to said longitudinal axis of said threaded shaft in the direction of said longitudinal axis of said threaded shaft, said sheath girth decreases, wherein said sheath girth increase and said sheath girth decrease are repeatable.

2. A girth adjustable device as recited in claim 1, wherein said threaded shaft further comprises at least one selected from a group consisting of: a controller-connector, a clockwise translation stopper, and a counter-clockwise translation stopper.

3. A girth adjustable device as recited in claim 1, further comprising at least one selected from a group consisting of: a module anti-rotation protrusion, and a housing anti-rotation cavity.

4. A girth adjustable device as recited in claim 1, further comprising at least one selected from a group consisting of: a bearing, and a friction reducer.

5. A girth adjustable device as recited in claim 1, wherein said plurality of shaft members further comprises at least one selected from a group consisting of: a side extension, a side extension having at least one groove and a side extension groove connector.

6. A girth adjustable device as recited in claim 1, wherein said controller further comprises at least one handle having a bearing.

7. A girth adjustable device as recited in claim 1, further comprising at least one selected from a group consisting of: a shaft member orifice stimulation protrusion, a sheath orifice stimulation protrusion, and a prostate stimulation protrusion.

8. A girth adjustable device as recited in claim 1, further comprising at least one selected from a group consisting of: a housing multi-purpose protrusion, and a sheath multi-purpose protrusion.

9. A girth adjustable device as recited in claim 1, further comprising at least one girth adjustment indicator.

10. A girth adjustable device as recited in claim 1, further comprising at least one strap.

11. A girth adjustable device as recited in claim 1, further comprising at least one grip body.

12. A girth adjustable device as recited in claim 1, further comprising at least one magnet.

13. A girth adjustable device as recited in claim 1, further comprising at least one selected from a group consisting of: a resilient band, and a spring.

14. A girth adjustable device as recited in claim 1, further comprising at least one weight.

15. A girth adjustable device as recited in claim 1, further comprising at least one penis ring.

16. A girth adjustable device as recited in claim 1, further comprising at least one closure element.

17. A girth adjustable device as recited in claim 1, further comprising at least one selected from a group consisting of: a controller angular transmission, and a threaded shaft angular transmission.

18. A girth adjustable device as recited in claim 1, wherein said controller further comprises a third end and a plurality of gears, wherein said plurality of gears connects said first end of said controller to said second end of said controller, wherein said plurality of gears connects said first end of said controller to said third end of said controller, wherein said second end of said controller is connected to said threaded shaft and said third end of said controller is connected to a second said threaded shaft, wherein when said first end of said controller rotates, said plurality of gears of said controller rotates, said second end of said controller, said third end of said controller, and said threaded shafts rotate following the rotation of said first end of said controller.

19. A girth adjustable device as recited in claim 1, further comprising an enclosed electric motor having at least one motor having a motor shaft, a motor housing and an electronic part, wherein said motor shaft of said motor having a motor shaft of said enclosed electric motor is connected to said first end of said controller, wherein said motor housing of said enclosed electric motor is secured or removably secured to said housing, wherein when said motor shaft of said motor having a motor shaft of said enclosed electric motor is rotated clockwise or counter-clockwise via said electronic part of said enclosed electric motor, said first end of said controller and said second end of said controller rotate following the rotation of said motor shaft of said motor having a motor shaft of said enclosed electric motor.

20. A girth adjustable device as recited in claim 1, wherein said first end of said controller further comprises at least one male connection and at least one female connection, wherein said male connection removably fits into said female connection, wherein when said male connection is connected to said female connection and when said first end of said controller rotates clockwise or counter-clockwise, said second end of said controller rotates following the rotation of said first end of said controller.

21. A girth adjustable device as recited in claim 19, wherein said first end of said controller further comprises at least one male connection and at least one female connection, wherein said male connection removably fits into said female connection, wherein when said male connection is connected to said female connection and when said first end of said controller rotates clockwise or counter-clockwise, said second end of said controller rotates following the rotation of said first end of said controller.

22. A girth adjustable device as recited in claim 1, further comprising at least one electronic part.

23. A girth adjustable device as recited in claim 22, further comprising at least one vibration motor.

24. A girth adjustable device as recited in claim 22, further comprising at least one heating element.

25. A girth adjustable device as recited in claim 22, further comprising at least one heart rate monitor.

26. A girth adjustable device as recited in claim 22, further comprising at least one electrical stimulation electrode.

27. A girth adjustable device as recited in claim 22, further comprising an enclosed electric motor having at least one motor having a motor shaft, a motor housing and an electronic part, wherein said motor shaft of said motor having a motor shaft of said enclosed electric motor is connected to said first end of said controller, wherein said motor housing of said enclosed electric motor is secured or removably secured to said housing, wherein when said motor shaft of said motor having a motor shaft of said enclosed electric motor is rotated clockwise or counter-clockwise via said electronic part of said enclosed electric motor, said first end of said controller and said second end of said controller rotate following the rotation of said motor shaft of said motor having a motor shaft of said enclosed electric motor.

28. A girth adjustable device as recited in claim 27, wherein said first end of said controller further comprises at least one male connection and at least one female connection, wherein said male connection removably fits into said female connection, wherein when said male connection is connected to said female connection and when said first end of said controller rotates clockwise or counter-clockwise, said second end of said controller rotates following the rotation of said first end of said controller.

29. A girth adjustable device as recited in claim 20, wherein said controller further comprises at least one locking system.

30. A girth adjustable device as recited in claim 21, wherein said controller further comprises at least one locking system.

31. A girth adjustable device as recited in claim 28, wherein said controller further comprises at least one locking system.

32. A girth adjustable device as recited in claim 1, wherein said controller or said second end of said controller is manufactured with said threaded shaft.

33. A girth adjustable device as recited in claim 1, further comprising at least one body skin protection element.

* * * * *